US009156938B2

(12) United States Patent
Swager et al.

(10) Patent No.: US 9,156,938 B2
(45) Date of Patent: Oct. 13, 2015

(54) COMPOSITIONS, METHODS, AND SYSTEMS COMPRISING FLUOROUS-SOLUBLE POLYMERS

(75) Inventors: Timothy M. Swager, Newton, MA (US); Jeewoo Lim, Cambridge, MA (US); Yohei Takeda, Minoo (JP)

(73) Assignee: Massachusetts Institute of Technology, Cambridge, MA (US)

( * ) Notice: Subject to any disclaimer, the term of this patent is extended or adjusted under 35 U.S.C. 154(b) by 932 days.

(21) Appl. No.: 13/213,647

(22) Filed: Aug. 19, 2011

(65) Prior Publication Data
US 2012/0177578 A1 Jul. 12, 2012

Related U.S. Application Data

(60) Provisional application No. 61/375,121, filed on Aug. 19, 2010.

(51) Int. Cl.
| | |
|---|---|
| *A61K 49/00* | (2006.01) |
| *C08G 61/02* | (2006.01) |
| *A61K 31/74* | (2006.01) |
| *A61B 5/1468* | (2006.01) |
| *A61B 5/1486* | (2006.01) |
| *A61K 49/12* | (2006.01) |

(Continued)

(52) U.S. Cl.
CPC ............ *C08G 61/02* (2013.01); *A61B 5/1468* (2013.01); *A61B 5/1486* (2013.01); *A61K 31/74* (2013.01); *A61K 49/0019* (2013.01); *A61K 49/126* (2013.01); *H01L 51/0035* (2013.01); *H01L 51/0036* (2013.01); *C08G 2261/124* (2013.01); *C08G 2261/146* (2013.01); *C08G 2261/148* (2013.01); *C08G 2261/312* (2013.01); *C08G 2261/3422* (2013.01); *H01L 51/0043* (2013.01); *H01L 51/0558* (2013.01); *H01L 51/424* (2013.01); *Y02E 10/549* (2013.01)

(58) Field of Classification Search
CPC ..................................................... A61K 31/74
See application file for complete search history.

(56) References Cited

U.S. PATENT DOCUMENTS

5,463,082 A * 10/1995 Horvath et al. ................. 549/46
2007/0215864 A1 9/2007 Luebben et al.

FOREIGN PATENT DOCUMENTS

WO WO 02/16463 A3 2/2002
WO WO 2008/021123 A1 2/2008

OTHER PUBLICATIONS

Invitation to Pay Additional Fees for PCT/US2011/048430 mailed Dec. 7, 2011.

(Continued)

*Primary Examiner* — Paul Dickinson
(74) *Attorney, Agent, or Firm* — Wolf, Greenfield & Sacks, P.C.

(57) ABSTRACT

The present invention generally relates to compositions, methods, and systems comprising polymers that are fluorous-soluble and/or organize at interfaces between a fluorous phase and a non-fluorous phase. In some embodiments, emulsions or films are provided comprising a polymer. The polymers, emulsions, and films can be used in many applications, including for determining, treating, and/or imaging a condition and/or disease in a subject. The polymer may also be incorporated into various optoelectronic device such as photovoltaic cells, organic light-emitting diodes, organic field effect transistors, or the like. In some embodiments, the polymers comprise pi-conjugated backbones, and in some cases, are highly emissive.

29 Claims, 24 Drawing Sheets

(51) Int. Cl.
  *H01L 51/00* (2006.01)
  *H01L 51/05* (2006.01)
  *H01L 51/42* (2006.01)

(56) References Cited

OTHER PUBLICATIONS

International Search Report and Written Opinion for PCT/US2011/048430 mailed Jun. 13, 2012.
Ahrens et al., In vivo imaging platform for tracking immunotherapeutic cells. Nat Biotechnol. Aug. 2005;23(8):983-7. Epub Jul. 24, 2005.
Babel et al., High electron mobility in ladder polymer field-effect transistors. J Am Chem Soc. Nov. 12, 2003;125(45):13656-7.
Bajaj et al., Array-based sensing of normal, cancerous, and metastatic cells using conjugated fluorescent polymers. J Am Chem Soc. Jan. 27, 2010;132(3):1018-22.
Bartusik et al., Application of 19F magnetic resonance to study the efficacy of fluorine labeled drugs in the three-dimensional cultured breast cancer cells. Arch Biochem Biophys. Jan. 15, 2010;493(2):234-41. Epub Nov. 10, 2009.
Becker et al., Receptor-targeted optical imaging of tumors with near-infrared fluorescent ligands. Nat Biotechnol. Apr. 2001;19(4):327-31.
Bouffard et al., A highly selective fluorescent probe for thiol bioimaging. Org Lett. Jan. 3, 2008;10(1):37-40. Epub Dec. 7, 2007.
Bouffard et al., Fluorescent Conjugated Polymers That Incorporate Substituted 2,1,3-Benzooxadiazole and 2,1,3-Benzothiadiazole Units. Macromolecules. 2008; 41(15):5559-5562.
Bulte, Hot spot MRI emerges from the background. Nat Biotechnol. Aug. 2005;23(8):945-6.
Chen et al., Highly Emissive Iptycene-Fluorene Conjugated Copolymers: Synthesis and Photophysical Properties. Macromolecules. 2008;41(18):6672-6676.
Fassina et al., Tissue inhibitors of metalloproteases: regulation and biological activities. Clin Exp Metastasis. 2000;18(2):111-20.
Frerrari, Cancer nanotechnology: opportunities and challenges. Nat Rev Cancer. Mar. 2005;5(3):161-71.
Guillemard et al., HER2-mediated internalization of a targeted prodrug cytotoxic conjugate is dependent on the valency of the targeting ligand. DNA Cell Biol. Jun. 2005;24(6):350-8.
Hilgenbrink et al., Folate receptor-mediated drug targeting: from therapeutics to diagnostics. J Pharm Sci. Oct. 2005;94(10):2135-46.
Holtze et al., Biocompatible surfactants for water-in-fluorocarbon emulsions. Lab Chip. Oct. 2008;8(10):1632-9. Epub Sep. 2, 2008.
Horváth et al., Facile catalyst separation without water: fluorous biphase hydroformylation of olefins. Science. Oct. 7, 1994;266(5182):72-5.
Horvath, Fluorous Biphase Chemistry. Acc Chem Res. 1998;31:641-50.
Izuhara et al., Poly(pyridinium phenylene)s: water-soluble N-type polymers. J Am Chem Soc. Dec. 16, 2009;131(49):17724-5.
Kamunhabwa et al., Enhancing the photodynamic effect of hypericin in human bladder transitional cell carcinoma spheroids by the use of the oxygen carrier, perfluorodecalin. Int J Oncol. Mar. 2006;28(3):775-80.
Kim et al., High ionization potential conjugated polymers. J Am Chem Soc. Aug. 31, 2005;127(34):12122-30.
King et al., Perfluorochemicals and Cell Culture. Nat Biotech. 1989;7:1037-42.
Kitamura et al., Design of Narrow-Bandgap Polymers. Syntheses and Properties of Monomers and Polymers Containing Aromatic-Donor and o-Quinoid-Acceptor Units. Chem. Mater. 1996;8(2):570-578.
Lee et al., Semiperfluoroalkyl Polyfluorenes for Orthogonal Processing in Fluorous Solvents. Macromolecules. 2010; 43(3):1195-1198.
Lim et al., Fluorous biphase synthesis of a poly(p-phenyleneethynylene) and its fluorescent aqueous fluorous-phase emulsion. Angew Chem Int Ed Engl. Oct. 4, 2010;49(41):7486-8.
Lim et al., Fluorous biphase synthesis of a poly(p-phenyleneethynylene) and its fluorescent aqueous fluorous-phase emulsion. Angew Chem Int Ed Engl. Oct. 4, 2010;49(41):7486-8. Supporting Information.
Mammen et al., Polyvalent Interactions in Biological Systems: Implications for Design and use of Multivalent Ligands and Inhibitors. Angew Chem Int Ed. 1998;37:2754-94.
McQuade et al., Conjugated polymer-based chemical sensors. Chem Rev. Jul. 12, 2000;100(7):2537-74.
McQuade et al., Signal Amplification of a "Turn-On" Sensor: Harvesting the Light Captured by a Conjugated Polymer. J. Am. Chem. Soc. 2000;122(49):12389-12390.
Meek et al, Near-infrared fluorophores containing benzo[c]heterocycle subunits. Org Lett. Jul. 17, 2008;10(14):2991-3. Epub Jun. 19, 2008.
Narayanan et al., Multiphoton Fluorescence Quenching of Conjugated Polymers for TNT Detection. J Phys Chem C. 2008;112(4):881-884.
Nesterov et al., In vivo optical imaging of amyloid aggregates in brain: design of fluorescent markers. Angew Chem Int Ed Engl. Aug. 26, 2005;44(34):5452-6.
Newman et al., Introduction to Organic Thin Film Transistors and Design of n-Channel Organic Semiconductors. Chem. Mater. 2004;16(23):4436-4451.
Parker et al., Folate receptor expression in carcinomas and normal tissues determined by a quantitative radioligand binding assay. Anal Biochem. Mar. 15, 2005;338(2):284-93.
Pawlicki et al., Two-photon absorption and the design of two-photon dyes. Angew Chem Int Ed Engl. 2009;48(18):3244-66.
Pond et al., Metal-ion sensing fluorophores with large two-photon absorption cross sections: aza-crown ether substituted donor-acceptor-donor distyrylbenzenes. J Am Chem Soc. Aug. 4, 2004;126(30):9291-306.
Quintana et al., Design and function of a dendrimer-based therapeutic nanodevice targeted to tumor cells through the folate receptor. Pharm Res. Sep. 2002;19(9):1310-6.
Raymond et al., Smart optical probes for near-infrared fluorescence imaging of Alzheimer's disease pathology. Eur J Nucl Med Mol Imaging. Mar. 2008;35 Suppl 1:S93-8. Eur J Nucl Med Mol Imaging. May 2008;35(5):1032.
Rose et al., Energy migration in conjugated polymers: the role of molecular structure. Philos Transact A Math Phys Eng Sci. Jun. 15, 2007;365(1855):1589-606.
Rose et al., Excited-state lifetime modulation in triphenylene-based conjugated polymers. J Am Chem Soc. Nov. 14, 2001;123(45):11298-9.
Satrijo et al., Anthryl-doped conjugated polyelectrolytes as aggregation-based sensors for nonquenching multicationic analytes. J Am Chem Soc. Dec. 26, 2007;129(51):16020-8. Epub Nov. 30, 2007.
Swager et al., Fluorescence Studies of Poly(p-phenyleneethynylene)s: The Effect of Anthracene Substitution. J. Phys. Chem. 1995;99(14): 4886-4893.
Swager et al., Self-amplifying Semiconducting Polymers for Chemical Sensors. Mater Res Soc Bull. 2002;27(6):446-50.
Takeda et al., Synthesis and Properties of Perfluoroalkyl-substituted Poly(theinopyrazine)s: Toward Creation of Electron-accepting Fluorous Conjugated Polymers. 91st Annual Spring Meeting of the Chemical Society of Japan. Conference scheduled for Mar. 28, 2011. Japanese Abstract published Mar. 11, 2011.
Terpetschnig et al., Luminescent Probes for NIR Sensing Applications. Near-Infrared Dyes for High Technology Applications. In: Nato ASI Ser. Ser 3. 1998;52:161-82.
Thomas et al., Chemical sensors based on amplifying fluorescent conjugated polymers. Chem Rev. Apr. 2007;107(4):1339-86. Epub Mar. 27, 2007.
Troyan et al., The FLARE intraoperative near-infrared fluorescence imaging system: a first-in-human clinical trial in breast cancer sentinel lymph node mapping. Ann Surg Oncol. Oct. 2009;16(10):2943-52. Epub Jul. 7, 2009.
Umeda et al., Surface-energy-dependent field-effect mobilities up to 1 cm2/V s for polymer thin-film transistor. J Appl Phys. 2009;105:24516-1-__.

(56) References Cited

OTHER PUBLICATIONS

Uno et al., Boron Trifluoride-Assisted Ziegler-Zeiser Reaction of Perfluoroalkyllithiums, An Efficient Synthesis of Perfluoroalkylated Heterocycles. Chem Lett. 1988;17:1165-68.

Usta et al., Air-stable, solution-processable n-channel and ambipolar semiconductors for thin-film transistors based on the indenofluorenebis(dicyanovinylene) core. J Am Chem Soc. Jul. 9, 2008;130(27):8580-1. Epub Jun. 11, 2008.

Wen et al., Poly(2,3-dihexylthieno[3,4-b]pyrazine) via GRIM Polymerization: Simple Preparation of a Solution Processable, Low-Band-Gap Conjugated Polymer. Macromolecules. 2008;41(13):4576-4578.

Wosnick et al., Molecular photonic and electronic circuitry for ultrasensitive chemical sensors. Curr Opin Chem Biol. Dec. 2000;4(6):715-20.

Wosnick et al., Synthesis and application of poly(phenylene ethynylene)s for bioconjugation: a conjugated polymer-based fluorogenic probe for proteases. J Am Chem Soc. Mar. 16, 2005;127(10):3400-5.

Xiang et al., Detection of myelination using a novel histological probe. J Histochem Cytochem. Dec. 2005;53(12):1511-6. Epub Jul. 26, 2005.

Yamamoto et al., π-Conjugated Donor-Acceptor Copolymers Constituted of π-Excessive and π-Deficient Arylene Units. Optical and Electrochemical Properties in Relation to CT Structure of the Polymer. J. Am. Chem. Soc. 1996;118(43):10389-10399.

Yan et al., A high-mobility electron-transporting polymer for printed transistors. Nature. Feb. 5, 2009;457(7230):679-86. Epub Jan. 21, 2009.

Yasuda et al., New Coplanar (ABA)n-Type Donor-Acceptor π-Conjugated Copolymers Constituted of Alkylthiophene (Unit A) and Pyridazine (Unit B): Synthesis Using Hexamethylditin, Self-Organized Solid Structure, and Optical and Electrochemical Properties of the Copolymers. Chem. Mater. 2005;17(24):6060-6068.

Yu et al., Increasing fluorous partition coefficients by solvent tuning. Org Lett. Aug. 18, 2005;7(17):3677-80.

Zhan et al., A high-mobility electron-transport polymer with broad absorption and its use in field-effect transistors and all-polymer solar cells. J Am Chem Soc. Jun. 13, 2007;129(23):7246-7. Epub May 18, 2007.

Zheng et al., Biotinylated poly(p-phenylene ethynylene): unexpected energy transfer results in the detection of biological analytes. Chem Commun (Camb). Dec. 21, 2004;(24):2798-9. Epub Nov. 4, 2004.

Zheng et al., Poly(arylene ethynylene)s in Chemosensing and Biosensing. Adv Polym Sci. 2005;177:151-79.

* cited by examiner

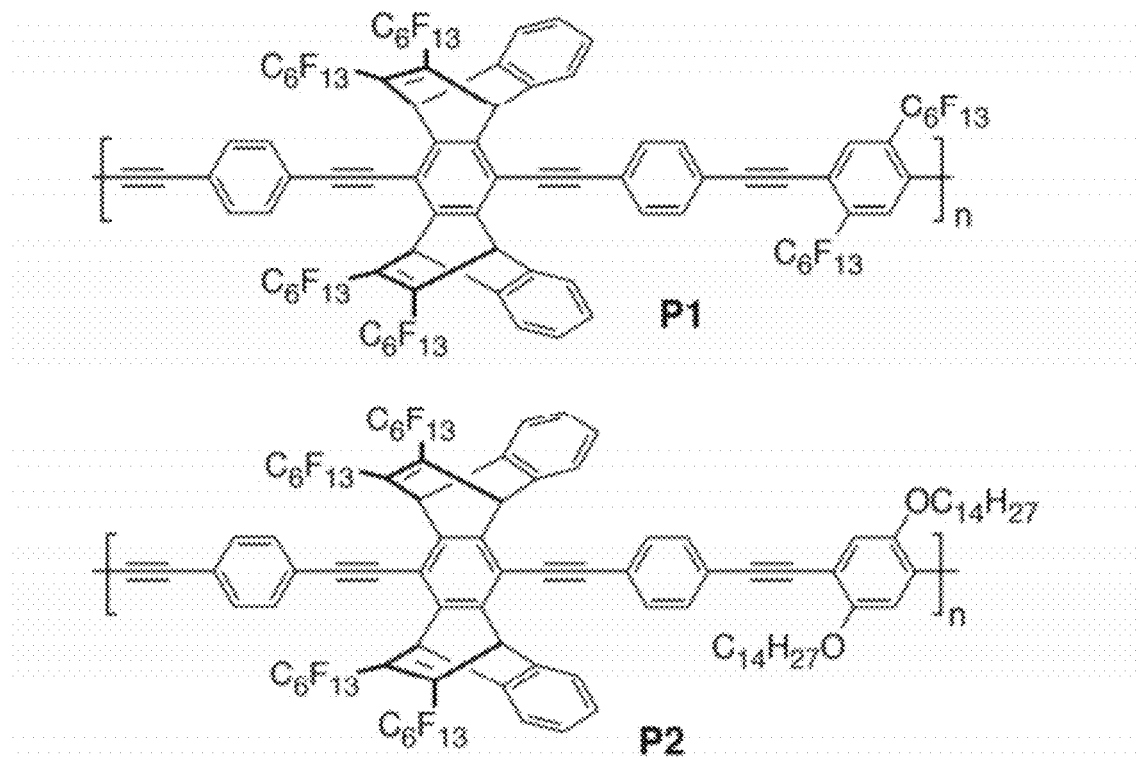
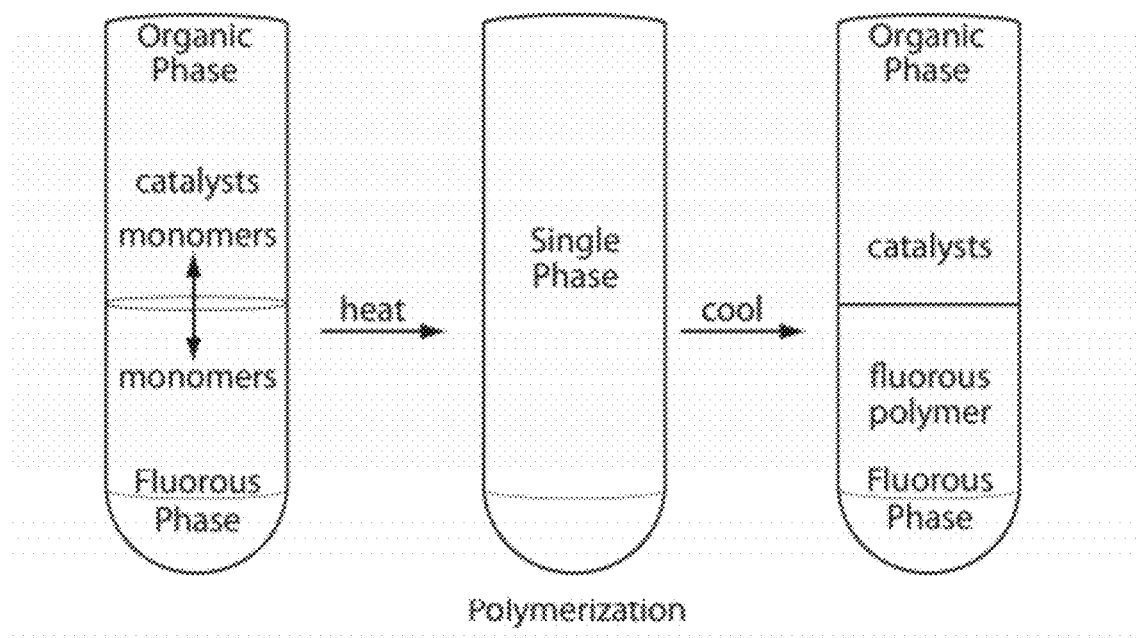
Fig. 5
Fig. 6

COMPOSITIONS, METHODS, AND SYSTEMS COMPRISING FLUOROUS-SOLUBLE POLYMERS

RELATED APPLICATIONS

This application claims priority under 35 U.S.C. §119(e) to U.S. Provisional Patent Application No. 61/375,121, filed Aug. 19, 2010, and entitled "Compositions, Methods, and Systems Comprising Fluorous-Soluble Polymers" which is incorporated herein by reference in its entirety for all purposes.

GOVERNMENT SPONSORSHIP

This invention was made with government support under Grant No. DE-SC0001088 awarded by the Department of Energy and Contract No. W911NF-07-D-0004 awarded by the Army Research Office. The government has certain rights in the invention.

FIELD OF THE INVENTION

The present invention generally relates to compositions, methods, devices, and systems comprising polymers that are fluorous-soluble and/or organize at an interface between a fluorous phase and non-fluorous phase.

BACKGROUND OF THE INVENTION

Heavily fluorinated materials display an array of interesting properties such as thermal and chemical stability, low surface energy, and high resistance to oxidation. These materials can display orthogonal solubility, dissolving in fluorous solvents with limited solubility in organic solvents, allowing for facile purification via liquid-to-liquid extraction and/or fluorous solid phase extraction. Fluorous small molecules, materials, and solvents have been utilized in areas such as fluorous biphase chemistry, liquid crystals, electronics, and arrays for biosample screening.

SUMMARY OF THE INVENTION

According to some aspects, the present invention provides polymers. In some embodiments, the polymer comprises a conjugated pi-backbone, the pi-backbone comprising a plane of atoms, and a first group and a second group attached to the pi-backbone, the first group having a first fixed height above the plane and the second group having a second fixed height below the plane wherein a sum of the first and second heights is at least about 4.5 Å, wherein the polymer has a fluorine content of greater than about 50% by mass.

In other embodiments, the polymer comprises a conjugated pi-backbone, the pi-backbone comprising a plane of atoms, and a first group and a second group attached to the pi-backbone, the first group having a first fixed height above the plane and the second group having a second fixed height below the plane wherein a sum of the first and second heights is at least about 4.5 Å, wherein the polymer has a solubility in non-fluorous solvents of less than about 0.01 mg/mL.

In some embodiments, the polymer comprises a conjugated pi-backbone comprising a thienopyrazine group, wherein the polymer has a fluorine content of greater than about 50% by mass.

In some embodiments, the polymer comprises a conjugated pi-backbone comprising a thienopyrazine group, wherein the polymer has a solubility in non-fluorous solvents of less than about 0.01 mg/mL.

According to some aspects, the present invention provides methods for forming a luminescent polymer. In some embodiments, a method of forming a luminescent polymer comprises providing a first solution comprising an organic solvent, a catalyst, and at least a first type of monomer, providing a second solution comprising a fluorous solvent and at least a second type of monomer, mixing the first and second solutions under conditions and for a period of time sufficient to allow for a luminescent polymer to form, the luminescent polymer comprising at least a portion of the first type of monomer and at least a portion of the second type of monomer, allowing the first and second solutions to phase separate, and isolating the polymer from the fluorous solvent.

According to some aspects, the present invention provides emulsions. In some embodiments, an emulsion comprises a non-fluorous continuous phase, a fluorous non-continuous phase, and a luminescent polymer contained within the fluorous phase, wherein the quantum yield of the luminescent polymer is greater than about 60%.

In other embodiments, an emulsion comprises a non-fluorous continuous phase, a fluorous non-continuous phase, and a polymer of the present invention substantially contained within the fluorous non-continuous phase.

In yet other embodiments, an emulsion comprises a non-fluorous continuous phase and a fluorous non-continuous phase, wherein a fluorous/non-fluorous interface is present between the fluorous and the non-fluorous phase, and a luminescent polymer arranged at the interface, wherein the quantum yield of the luminescent polymer is greater than about 60%.

In still yet other embodiments, an emulsion comprises a non-fluorous continuous phase and a fluorous non-continuous phase, wherein a fluorous/non-fluorous interface is present between the fluorous and the non-fluorous phase, and a polymer of the invention of arranged at the interface.

According to other aspects of the present invention, methods of determining, treating, or imaging a condition and/or disease in a subject are provided. In some embodiments, a methods of determining, treating, or imaging a condition and/or disease in a subject comprises providing an emulsion comprising a fluorous non-continuous phase, a non-fluorous continuous phase, at least one surfactant, at least one surface-altering moiety, and a polymer of the present invention, wherein the polymer and the at least one surfactant is contained with the fluorous phase; administering the emulsion to the subject, and imaging at least a portion of the subject.

According to still yet other aspects of the present invention, composition for determination, treating, or imaging a condition and/or disease in a subject are provided. In some embodiments, a composition for determination, treating, or imaging a condition and/or disease in a subject comprises an emulsion comprising a fluorous discontinuous phase, a fluorescent entity associated with the fluorous discontinuous phase, and at least one targeting moiety, associated with the emulsion, for targeting a species in or on the tissue or subject.

BRIEF DESCRIPTION OF THE DRAWINGS

FIG. 5 shows chemical structures of non-limiting polymers P1 and P2 of the present invention.

FIG. 6 illustrates a non-limiting example of a fluorous biphase synthesis of fluorous-soluble polymers.

Figure 1:
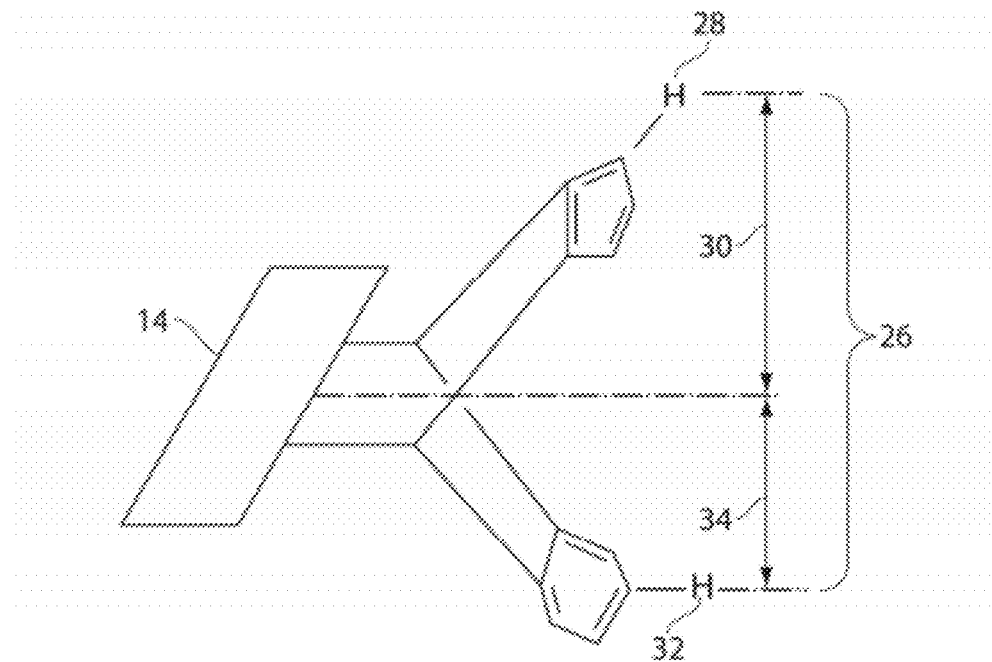
FIG. 1 shows a schematic of a rigid side group having fixed heights above and below a pi-backbone plane.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

The present invention generally relates to compositions, methods, and polymer systems that are fluorous-soluble or organize at interfaces between another solvent and a fluorous phase. The subject matter of the present invention involves, in some cases, interrelated products, alternative solutions to a particular problem, and/or a plurality of different uses of one or more systems and/or articles.

Some embodiments described herein provide materials having enhanced properties, including solubility, quantum yield, electron affinity, stability in air, semiconducting properties, in solution or in solid state. In some cases, the materials may include various fluorine-containing groups (e.g., perfluoroalkyl chains) and can also be readily purified and processed as solutions, emulsions, solid state materials (e.g., films), and the like. The materials may be useful in a wide variety of applications, including luminescence-based imaging (e.g., bio-imaging) and detection. For example, the materials may be useful in the determination, treatment, and/or imaging of a condition or disease in a subject. In some cases, the materials may be incorporated into an optoelectronic device such as a photovoltaic cell, organic light-emitting diode, organic field effect transistor, or the like.

In some embodiments of the present invention, fluorous-soluble, i.e., polymers which are substantially soluble in fluorous solvents and substantially insoluble in non-fluorous solvents, are provided. In some embodiments, as described herein, a polymer of the present invention is substantially soluble in fluorous solvents and is substantially insoluble in non-fluorous solvents. That is, the polymer has selective solubility in fluorous-soluble solvents. In some cases, the polymer has a solubility in non-fluorous solvents of less than about 0.2 mg/mL, less than about 0.15 mg/mL, less than about 0.10 mg/mL, less than about 0.05 mg/mL, less than about 0.04 mg/mL, less than about 0.03 mg/mL, less than about 0.02 mg/mL, less than about 0.01 mg/mL, less than about 0.005 mg/mL, less than about 0.001 mg/mL, or less. In some cases, the polymer has solubility in fluorous-solvents of greater than about 0.1 mg/mL, greater than about 0.2 mg/mL, greater than about 0.3 mg/mL, greater than about 0.4 mg/mL, greater than about 0.5 mg/mL, greater than about 0.6 mg/mL, greater than about 0.75 mg/mL, greater than about 1.0 mg/mL, or greater. In some embodiments, the polymer has a solubility in a fluorous-solvent between about 0.1 mg/mL and about 5 mg/mL, between about 0.2 mg/mL and about 4 mg/mL, between about 0.3 mg/mL and about 3 mg/mL, between about 0.4 mg/mL and about 2 mg/mL, between about 0.5 mg/ml and about 1.5 mg/mL, between about 0.5 mg/mL and about 1 mg/mL, etc.

Those of ordinary in the art will be aware of methods for determining the solubility of a polymer in a selected solvent. For example, a polymer may be agitated (e.g., stirred) with a known volume (e.g., about 1 mL, about 2 mL, about 3 mL, about 5 mL, about 10 mL, about 25 mL, about 50 mL, about 100 mL, etc.) of a selected solvent for a period of time (e.g., about 10 minutes, about 20 minutes, about 30 minutes, about 60 minutes, etc.). Following agitation, the solution may be filtered (e.g., to remove any undissolved polymer). The volatile components (e.g., solvent) of the filtered solution may be removed and the weight of the solid material may be determined (e.g., by subtracting the weight of the container from the total weight of the container and the solid). The solubility of the polymer can then be calculated (e.g., weight of solid material divided by known volume of solvent). In embodiments where the polymer is luminescent, following filtration of the solvent, an emission spectra of the solution may be used to determine the solubility of the polymer. In cases where the luminescent polymer is essentially insoluble in non-fluorous solvent, the solution following filtration may have essentially no emission. In some cases, the solvent(s) used to determine the solubility of a polymer in non-fluorous solvents is water, acetone, toluene, benzene, tetrahydrofuran, dimethylformamide, hexanes, dimethylsulfoxide, ethyl acetate, acetonitrile, or the like.

In some embodiments, the polymers of the present invention are modestly soluble in a fluorous solvent and/or also have an affinity for a second solvent, such as a non-fluorous solvent. Mixed solvent dispersions of these materials may be used to create systems where the polymer is, in part, immobilized with respect to the interface of the fluorous solvent and the second, non-fluorous solvent. In a particular embodiment, the second solvent is water. In these embodiments, the polymer may be attached to a water-soluble biological recognition element and/or targeting moiety, as described herein.

In some embodiments, the polymer comprises a conjugated polymer backbone, and in some cases, is emissive. That is, the polymer may emit a luminescence emission (e.g., fluorescence, phosphorescence, etc.) upon exposure to an external source of energy such as electromagnetic radiation, a chemical reagent, or the like. In some cases, the polymer may be contained in an emulsion and/or formed as a film. Emulsions and films comprising the materials described herein may find use in numerous applications, including the detection, treatment, and/or imaging of a condition or disease in a subject, in light emitting diodes, and in photovoltaic devices, for example.

In some embodiments, a polymer of the present invention has a fluorine content of greater than about 50% by mass. That is, based on the total weight of the polymer, greater than about 50% mass of the polymer may be attributed to fluorine atoms. In some cases, the polymer has a fluorine content of greater than about 55%, greater than about 60%, greater than about 65%, greater than about 70%, greater than about 80%, greater than about 85%, or more. Those of ordinary skill in the art would be able to select the appropriate method for determining the fluorine content of the polymer. In some cases, the fluorine content may be estimated by determining the fluorine content of a repeating set of monomers. That is, in some cases, a polymer contains a set of two, three, four, etc., repeating monomers. Although the polymer generally comprises end-capping groups (e.g., the groups present at the end of the polymer chains), the weight of the end-capping groups is usually minimal as compared to the weight of the repeating units in the chain. Accordingly, in some cases, the fluorine content of a polymer may be determined by determining the fluorine content of the repeating units (e.g., by dividing the total mass of the fluorine atoms in the repeating units by the total mass of the repeating units).

Non-fluorous solvents will be readily known to those of ordinary skill in the art. Generally, non-fluorous solvents are substantially immiscible with fluorous solvents. In some cases, the fluorous solvent and the non-fluorous solvent can be selected to be substantially immiscible within the time frame of formation of an emulsion, within the time frame of reaction or interaction, etc. Those of ordinary skill in the art can select suitable substantially miscible or substantially immiscible fluids, using contact angle measurements or the like, to carry out the techniques of the invention. Non-limiting examples of non-fluorous solvents include water, acetone, toluene, benzene, tetrahydrofuran, dimethylformamide, hexanes, dimethylsulfoxide, ethyl acetate, acetonitrile, etc., and combinations thereof. In some cases, the non-fluorous solvent comprises water.

Non-limiting examples of fluorous solvents include perfluorocarbons (PFCs) and hydrofluoroethers (HFEs). Non-limiting examples of PFCs include perfluorohexane, perfluoromethylcyclohexane, and perfluorodecalin. A non-limiting example of n HFE is nonafluorobutyl methyl ether (e.g., sold under the trade name HFE-7100). Other non-limiting examples of fluorous solvents include perfluorobutyltetrahydrofuran, perfluoroalkyl halides (e.g., perfluorooctyl bromide), perfluorotoluene, perfluoro-2-methyl pentane, perfluorobenzene, perfluoro(1,3-dimethylcyclohexane), and 2H,3H-perfluororpentane, and combinations thereof.

In some embodiments, a polymer may be appended with various pendant groups (e.g., side chains) attached to the backbone of the polymer to tune properties such as solubility and cell permeability, for example, of the conjugated polymer. In some cases, the fluorine content of a polymer may be increased or decreased by altering the size and/or number of pendant fluorinated groups associated with the polymer backbone. In some embodiments, a polymer comprises a plurality of fluorinated pendant groups (e.g., at least two, at least three, at least four, at least five, at least six, at least seven, at least eight, etc.). For example, the plurality of fluorinated pendant groups may be the same or different and may be partially fluorinated and/or perfluorinated hydrocarbon chains and/or branched hydrocarbons. In some cases, the polymer comprises a plurality of partially fluorinated hydrocarbons and/or perfluorohydrocarbons, e.g., having 1 to 30 carbon atoms, 3 to 20 carbon atoms, etc. The hydrocarbons can be fluorinated at any locations where a hydrogen atom is generally present. There may be any combination of carbon-fluorine and/or carbon-hydrogen bonds. Any branching of the hydrocarbon which is present can occur anywhere along a hydrocarbon chain and the branches can vary in length.

The pendant groups may be attached to the backbone of the polymer via various covalent or non-covalent bonds. In some embodiments, the pendant group may be covalently attached to the polymer via a carbon-carbon bond. In some embodiments, the pendant group may be covalently attached to the polymer via an alkoxy linkage, an amide linkage, a thioether linkage, an acyl linkage, or the like. In some embodiments, a polymer of the present invention may comprise at least one pendant group having the formula $(CH_2CH_2O)_kR^{23}$, wherein k is an integer between 1-100, or between 1-50, or between 1-20, or between 1-10, or between 1-5, and $R^{23}$ is hydrogen, alkyl, heteroalkyl (e.g., alkoxy), aryl, or heteroaryl, each optionally substituted. Other polyether chains may be contemplated for use as a pendant group.

Non-limiting examples of hydrocarbons which can be partially fluorinated and/or perfluorinated are branched or straight chain propyl, butyl, pentyl, hexyl, heptyl, octyl, nonyl, decyl, undecyl, dodecyl, etc., groups. Non-limiting examples of fluorinated pendant groups include —$C_2F_5$, —$CH_2CF_3$, —$C_3F_7$, —$(CH_2)_2CF_3$, —$C_4F_9$, —$(CH_2)_2(CF_2)CF_3$, —$(CH_2)_3CF_3$, —$(CH_2)_2(CHF)CF_3$, —$C_5F_{11}$, —$(CH_2)_2(CF_2)_2CF_3$, —$C_6F_{13}$, —$(CH_2)_2(CF_2)_3CF_3$, —$(CH_2)_2(CF_2)_4CF_3$, —$C_7F_{15}$, —$(CH_2)_2(CF_2)_5CF_3$, —$(CH_2)_2(CF_2)_9CF_3$, —$(CH_2)_3(CF_2)_4CF_3$, —$(CH_2)_2(CF_2)_2(CF_3CF_2CF_2)CF(CF_2)_2CF_3$, —$C_8F_{17}$, —$C_9F_{19}$, —$C_{10}F_{21}$, —$C_{11}F_{23}$, and —$C_{12}F_{25}$.

The incorporation of fluorine-containing groups may provide many advantageous properties. As noted herein, the polymers may exhibit orthogonal solubility, i.e., may be substantially soluble in fluorous solvents but may be substantially insoluble in non-fluorous solvents, allowing for orthogonal processing of devices (e.g., optoelectronic devices) that require multi-layered configurations with underlying polymer layers remaining intact. The fluorine-containing groups may also provide the ability to position the polymers at a particular interface (e.g., between fluorous solvents and non-fluorous solvents) or on a particular surface. In some cases, the electron-withdrawing nature of fluorine atoms can increase electron affinity of the polymers, which can improve the ability of the polymers to accept electrons and accommodate negatively charged carriers. Air-stability may also enhanced by fluorine incorporation by increasing the barrier against oxygen and/or water diffusion into the polymer materials. The term "polymer," as used herein, refers to extended molecular structures comprising a backbone (e.g., non-conjugated backbone, conjugated backbone) which optionally contain pendant side groups, where "backbone" refers to the longest continuous bond pathway of the polymer. In one embodiment, at least a portion of the polymer is conjugated, i.e. the polymer has at least one conjugated portion. By this arrangement, electron density or electronic charge can be conducted along the portion where the electronic charge is referred to as being "delocalized." In some embodiments, the polymer comprises a pi-conjugated portion, where p-orbitals participating in conjugation can have sufficient overlap with adjacent conjugated p-orbitals. In some embodiments, the polymer comprises a sigma-conjugated portion. In one embodiment, the conjugated portion is at least about 30 Å in length. In some embodiments, the entire backbone is conjugated and the polymer is referred to as a "conjugated polymer."

Polymers having a conjugated pi-backbone capable of conducting electronic charge are typically referred to as "conducting polymers." In some cases, the conjugated pi-backbone may be defined by a plane of atoms directly participating in the conjugation, wherein the plane arises from a preferred arrangement of the p-orbitals to maximize p-orbital overlap, thus maximizing conjugation and electronic conduction. In some cases, the pi-backbone may preferably have a non-planar or twisted ground state conformation, leading to decreased conjugation and a higher energy conduction band. An example of a conjugated pi-backbone defining essentially a plane of atoms are the carbon atoms of a polyacetylene chain.

In some cases, a polymer of the present invention is a luminescent polymer. As used herein, a "luminescent polymer" refers to a polymer that can absorb a quantum of electromagnetic radiation to cause the polymer to achieve an excited state structure. Luminescent polymers may also be capable of emitting radiation. Radiation can be emitted from the polymer or from a chromophore associated with (e.g., covalently bound to, non-covalently bound to, etc.) the polymer. Typically, the extent of delocalized bonding allows the existence of a number of accessible electronic excited states. If the conjugation is so extensive so as to produce a near continuum of excited states, electronic excitations can involve a valence band, the highest fully occupied band, and a conduction band, often referred to as a band gap, as described herein.

In some embodiments, exposure of the polymer of the present invention to a source of energy may cause an emission (e.g., fluorescence, phosphorescence, or chemiluminescence). The source of energy may comprise electromagnetic radiation, electrical energy, sound energy, thermal energy, or chemical energy. In a particular embodiment, exposure of the conjugated polymer to electromagnetic radiation causes a fluorescence emission. As used herein, an emitted radiation or "emission" may be luminescence emission, in which "luminescence" is defined as an emission of ultraviolet or visible radiation. Specific types of luminescence include fluorescence, for example, in which a time interval between absorption and emission of visible radiation ranges from about $10^{-10}$ to about $10^{-8}$ s, phosphorescence, other types of luminescence, and the like. For example, the emission may be "chemiluminescence," which refers to emission of radiation due to a chemical reaction, or "electrochemiluminescence," which refers to emission of radiation due to electrochemical reactions. In some cases, the emission may be fluorescence emission.

In some embodiments, a polymer of the present invention is luminescent, and the polymer has a quantum yield greater than about 60%, greater than about 65%, greater than about 70%, greater than about 75%, greater than about 80%, greater than about 85%, greater than about 90%, or greater than about 95%. The term "quantum yield," as used herein, is given its ordinary meaning in the art and refers to the number of photons emitted per adsorbed photon. Those of ordinary skill in the art will be aware of methods and systems for determining the quantum yield of a polymer.

In some embodiments, the polymer is selected from the group consisting of polyarylenes, polyarylene vinylenes, polyarylene ethynylenes and ladder polymers, i.e. polymers having a backbone that can only be severed by breaking two bonds. Examples of such polymers include polythiophene, polypyrrole, polyacetylene, polyphenylene and substituted derivatives thereof. In some embodiments, the polymer may include one or more metal atoms, positioned within the polymer backbone and/or on a pendant side group.

In some embodiments, a polymer of the present invention comprises a conjugated pi-backbone, the pi-backbone comprising essentially a plane of atoms. A first group and a second group may be attached to the pi-backbone of the polymer. Both the first and second groups have at least some atoms that are not planar with the plane of atoms such that the atoms can be positioned either below or above the conjugated plane of atoms. It is a feature of the invention that these heights are fixed, the term "fixed height" defined as a height of an atom that is not planar with the plane of atoms where the atom is free of substantial rotational motion. In one embodiment, a sum of the fixed heights is at least about 4.5 Å. In some cases, a sum of the fixed heights is at least about 5.0 Å, is at least about 5.5 Å, is at least about 6.0 Å, is at least about 6.5 Å, or greater. In another embodiment, the pi-backbone is free from pi-stacking.

FIG. 1 shows an example of a "fixed height" where side group 26 is bonded to the backbone in a manner that restricts rotational motion. In this example, hydrogen atoms 26 and 28 define a fixed height relative to plane 14. The fixed height of sidegroup 26 is defined by hydrogen atom 28, having a fixed height above the plane 30 and hydrogen 32 having a fixed height below the plane 34. In one embodiment, a sum of the fixed heights is at least about 4.5 Å and more preferably at least about 5.0 Å.

In some embodiments, the polymer of the present invention comprises at least one monomer having an iptycene structure. Iptycenes are a class of compounds based off a triptycene structure, where the prefix indicates the number of separated arene planes. Examples of iptycenes include triptycenes (3 planes) and pentiptycenes (5 planes). The arene planes are fused together at the [2.2.2]bicyclooctane junctions. The arene planes are not limited to benzene rings; they may be any polycyclic aromatic structure. Various embodiments of the invention involve use of molecules comprising an iptycene, such as a pentiptycene. One structural feature of one set of embodiments of the invention, the iptycenes, is that the [2.2.2]bicyclic ring system forms the intersections of planes defined by aromatic rings. Another class of molecules of the invention are those molecules that include a [2.2.2]bicyclic ring system, with each branch of the system connecting to cyclic aromatics. Each of the bridgeheads in these molecules may be connected to three cyclic aromatics, and at least one of the cyclic aromatics may be connected to another [2.2.2] bridgehead-pair of center, or may be fused to another aromatic system (shares at least one bond in common with another aromatic system).

In some embodiments, at least two of the cyclic aromatics emanating from the central [2.2.2]system may be fused to another aromatic system or connected to another [2.2.2]center, and in other embodiments, all three cyclic aromatics may be fused to other aromatic systems or connected to a bridgehead center. For example, alkenes, may emanate from bridgehead centers of various molecules of the invention. Those of ordinary skill in the art will recognize that a wide variety of shape-persistent with high free volume molecules are possible.

In some embodiments of the present invention, a polymer of the present invention comprising at least one iptycene monomer. In some cases, the iptycene monomer may include primarily carbon ring atoms. In some cases, the iptycene monomer may include both carbon ring atoms and heteroatom ring atoms. In some cases, the iptycene monomer has the structure:

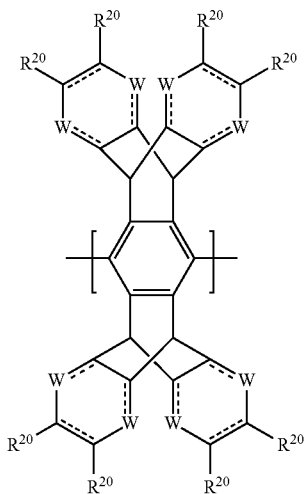

wherein each $R^{20}$ can be the same or different and is hydrogen, alkyl, heteroalkyl (e.g., alkoxy), aryl, or heteroaryl, any of which is optionally substituted with one or more fluorine atoms; each W is CH or $CH_2$, and each ═══ is a single or double bond.

In some embodiments of the present invention, an iptycene monomer incorporated into a polymer of the present invention has the structure:

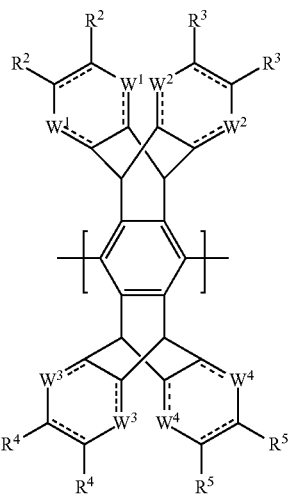

wherein each $R^2$-$R^5$ may be the same or different and is hydrogen, alkyl, heteroalkyl (e.g., alkoxy), heteroalkoxy, aryl, or heteroaryl, any of which is optionally substituted with one or more fluorine atoms, each $W^1$-$W^4$ can be the same or different and is CH or $CH_2$, and each ═══ is a single or double bond. In some embodiments, each $W^2$ and each $W^4$ is CH; or each $W^1$ and each $W^3$ is CH; or each $W^1$-$W^4$ is CH. In some cases, each $W^4$ is CH, and each $R^2$ and each $R^4$ is alkyl, heteroalkyl (e.g., alkoxy), heteroalkoxy, aryl, or heteroaryl, any of which is optionally substituted with one or more fluorine atoms; and each $R^3$ and $R^5$ is hydrogen. In some embodiments, each $R^2$ and each $R^4$ is alkyl, optionally fluorinated.

In some embodiments of the present invention, a polymer of the present invention includes at least one repeating unit comprising a bicyclic unit, for example, a [2.2.2] or a [2.2.1] bicyclic unit. In a particular embodiment of the present invention, a repeating unit incorporated into a polymer of the present invention has the structure:

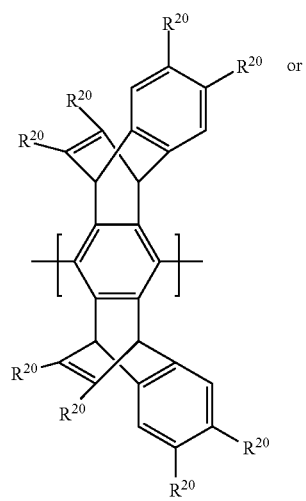

-continued

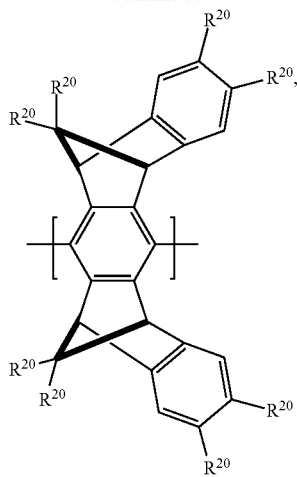

wherein each $R^{20}$ can be the same or different and is hydrogen, alkyl, heteroalkyl (e.g., alkoxy), aryl, or heteroaryl, any of which is optionally substituted with one or more fluorine atoms In some embodiments, the polymer comprises a pi-backbone comprising the structure:

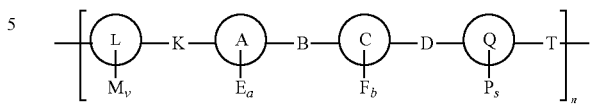

wherein A, C, L, and Q are aromatic groups; B, D, K, and T are selected from the group consisting of a carbon-carbon double bond and a carbon-carbon triple bond; a, b, s, and v are integers which can be the same or different and are 0-4, provided not all of a, b, s, and v are zero; and n is less than about 10,000, wherein at least one of E, F, M, and P comprises the first and second group; wherein at least one of E, F, M, and P includes a bicyclic ring system having aromatic or non-aromatic groups; and wherein each E, F, M, and P group is or is optionally substituted by one or more $R^{22}$ wherein each $R^{22}$ is selected from the group consisting hydrogen, alkyl, heteroalkyl (e.g., alkoxy), heteroalkoxy, aryl, and heteroaryl, any of which is optionally substituted with one or more fluorine atoms.

In some embodiments, the polymer of the present invention has the formula:

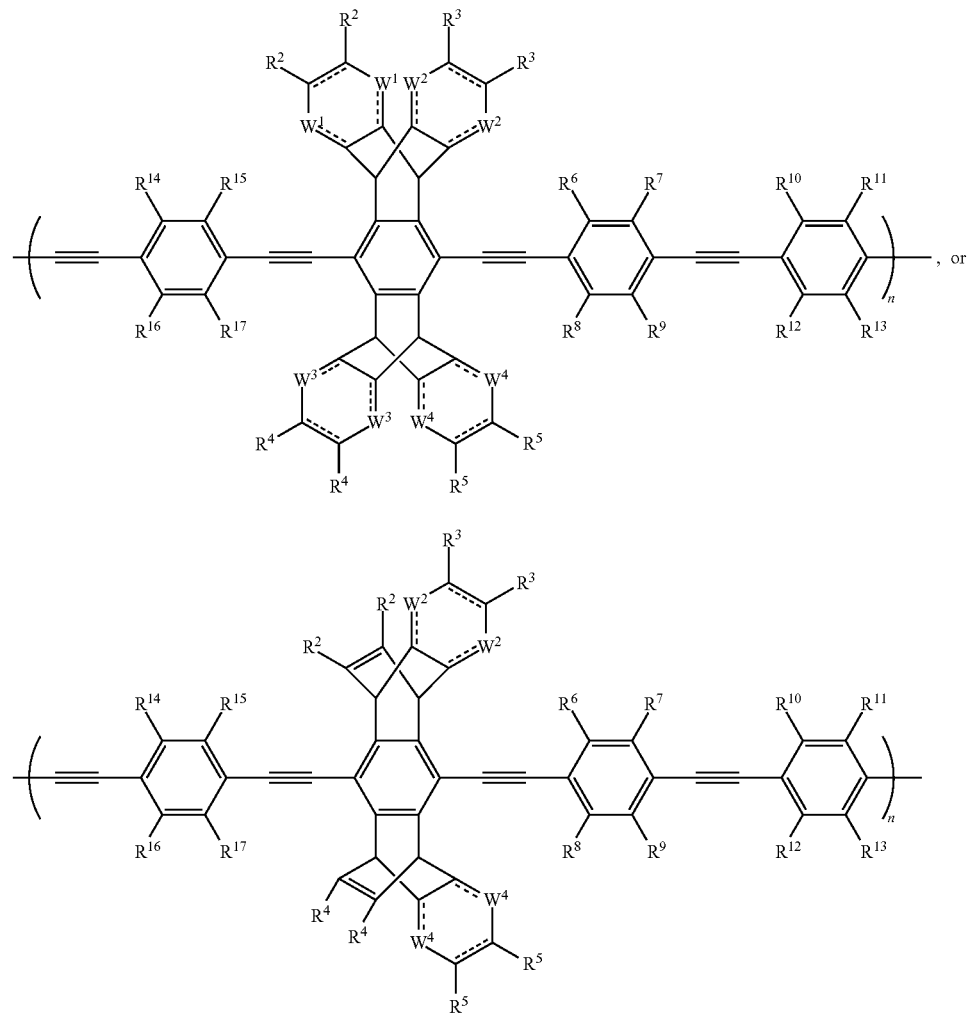

wherein each $R^2$-$R^{17}$ may be the same or different and is hydrogen, alkyl, heteroalkyl (e.g., alkoxy), heteroalkoxy, aryl, or heteroaryl, any of which is optionally substituted with one or more fluorine atoms, each $W^1$-$W^4$ can be the same or different and is CH, or $CH_2$, and n is less than about 10,000. In some embodiments, each $W^2$ and each $W^4$ is CH; or each $W^2$ and each $W^3$ is CH; or each $W^1$-$W^4$ is CH. In some cases each $W^2$ and each $W^4$ are CH, and each $R^2$ and each $R^4$ is an alkyl group, optionally fluorinated; and each $R^3$ and $R^5$ is hydrogen. In some cases, each of $R^6$-$R^9$ is hydrogen and/or each of $R^{14}$-$R^{17}$ is hydrogen. In some cases, $R^{19}$ and $R^{13}$ or $R^{11}$ and $R^{12}$ are each alkyl, heteroalkyl (e.g., alkoxy), heteroalkoxy, aryl, or heteroaryl, any of which is optionally substituted with one or more fluorine atoms, and $R^{11}$ and $R^{12}$ or $R^{10}$ and $R^{13}$, respectively, are hydrogen.

In some embodiments of the present invention, the polymer has the structure:

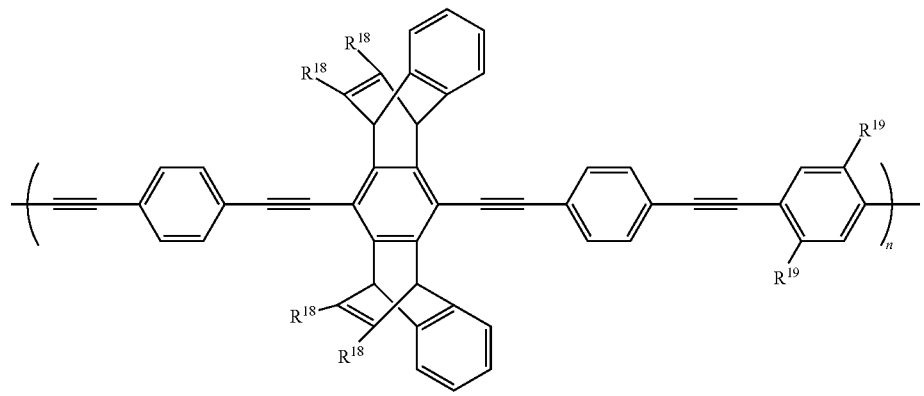

wherein each $R^{18}$ and each $R^{19}$ is alkyl, heteroalkyl (e.g., alkoxy), heteroalkoxy, aryl, and heteroaryl, any of which is optionally substituted with one or more fluorine atoms; and wherein n is less than about 10,000.

In a particular embodiment, a polymer of the present invention has a structure as shown in FIG. 5, wherein n is less than about 10,000. In another embodiment, a polymer of the present invention has the structure:

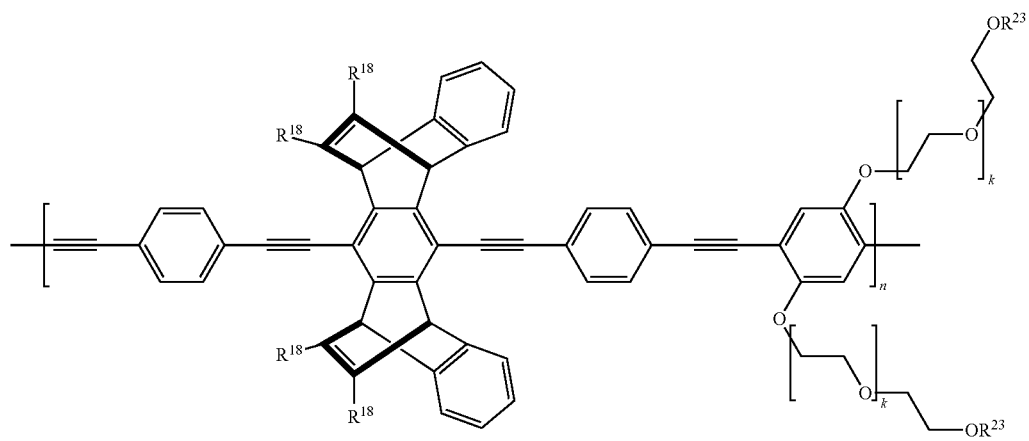

wherein each $R^{18}$ and $R^{23}$ is alkyl, heteroalkyl, (e.g., alkoxy), heteroalkoxy, aryl, and heteroaryl, any of which is optionally substituted with one or more fluorine atoms, n is less than about 10,000, and k is an integer between 1 and 10.

In one set of embodiments, the polymer of the present invention comprises a monomer having the structure:

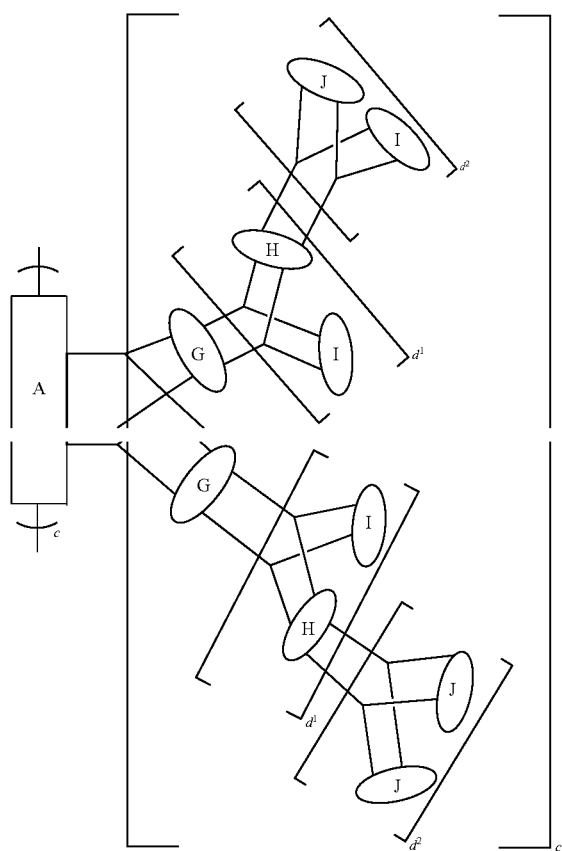

wherein each G, H, I and J may be the same or different and are aromatic or cycloalkyl groups, optionally substituted; d is 1 or 2; each d' is 0 or 1, such that when $d^1=0$, $d^2=0$, and when $d^1=1$, $d^2=0$ or 1; and c is any number between 1 and 10,000.

In some embodiments, G and H may be the same or different, and each may be selected from the aromatic group consisting:

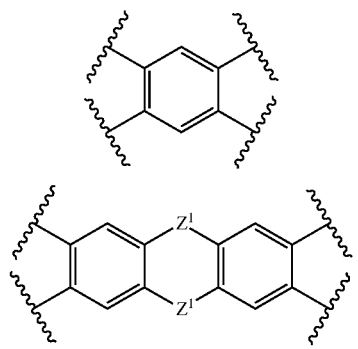

-continued

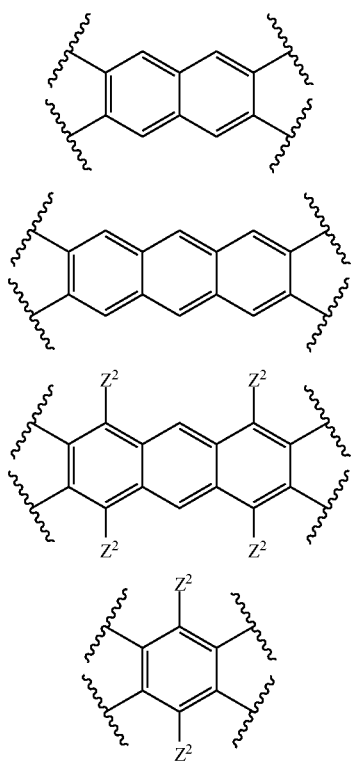

In some embodiments, I and J may be the same or different and each can be selected from the group consisting of:

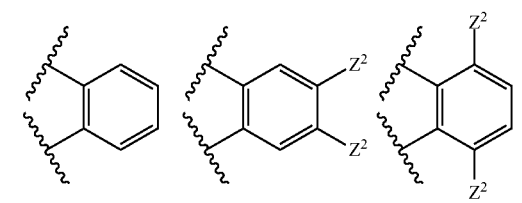

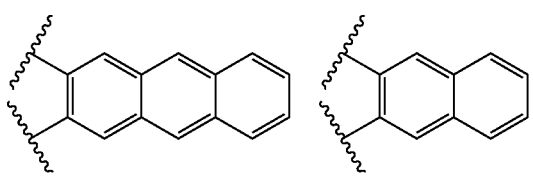

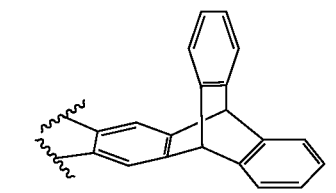

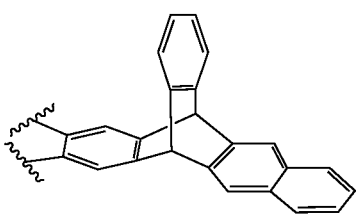

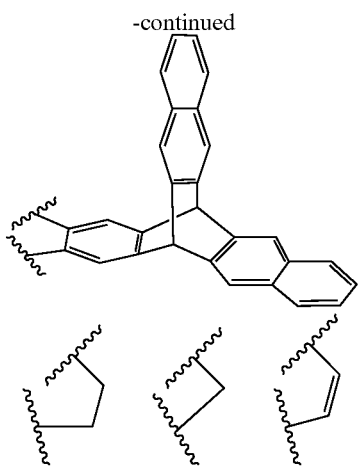

Any hydrogen in G, H, I and J may be substituted by one or more $R^{21}$, wherein $R^{21}$ can be the same or different and is alkyl, heteroalkyl, (e.g., alkoxy), aryl, and heteroaryl, any of which is optionally substituted with one or more fluorine atoms.

In one embodiment of the invention, molecules for use in the formation of rigid shape-persistent polymers with high degrees of internal free volume may involve substitution about the bicyclic ring system, which may provide the needed geometry to provide internal free volume in the structure. In some embodiments of the invention, rigid shape persistent polymers with high degrees of internal free volume may be provided in which the distance from the bridgehead atom to the van der Waals contact of the most distant atom of the smallest substituent directly attached to the bridgehead carbon is more than 4 Å, preferably 5 Å, 6 Å, or 7 Å, or even greater. The significance of this group is that it serves to define additional free volume and internal surfaces, from which important organizational properties in conjunction with polymers and liquid crystals may be optimized. The larger groups further provide structures with greater shape persistence, since the polymers may not be easily collapsed and prevent the interpenetration of one polymer into another.

Some embodiments described herein provide polymers comprising a heteroaryl moiety within the polymer backbone. The heteroaryl moiety may include at least one heteroatom ring atom in the aromatic ring(s) with the remainder of the ring atoms being carbon atoms. Suitable heteroatoms include oxygen, sulfur, and nitrogen. The heteroaryl ring may be monocyclic or polycyclic. In some embodiments, the heteroaryl group may be substituted with one or more non-hydrogen substituents. Suitable heteroaryl groups include, but are not limited to, furanyl, thienyl, pyridyl, pyrrolyl, N-lower alkyl pyrrolyl, pyridyl N-oxide, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl and the like, any of which may be optionally substituted. In some cases, the heteroaryl group may be thiophene. In some cases, the thiophene group may be substituted, or may be fused to another ring. For example, the polymer may include a thienopyrazine group.

In some cases, the polymer comprises a monomer having the following structure,

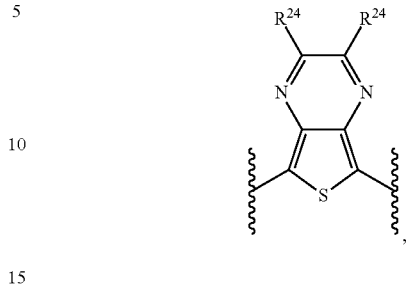

wherein each $R^{24}$ can be the same or different and is hydrogen, alkyl, heteroalkyl (e.g., alkoxy), aryl, or heteroaryl, any of which is optionally substituted with one or more fluorine atoms. In some cases, $R^{24}$ is a group comprising at least one fluorine atom. In some cases, $R^{24}$ is a fluoroalkyl group. For example, at least one $R^{24}$ can be selected from the group consisting of $-C_2F_5$, $-CH_2CF_3$, $-C_3F_7$, $-(CH_2)_2CF_3$, $-C_4F_9$, $-(CH_2)_2(CF_2)CF_3$, $-(CH_2)_3CF_3$, $-(CH_2)_2(CHF)CF_3$, $-C_5F_{11}$, $-(CH_2)_2(CF_2)_2CF_3$, $-C_6F_{13}$, $-(CH_2)_2(CF_2)_3CF_3$, $-(CH_2)_2(CF_2)_4CF_3$, $-C_7F_{15}$, $-(CH_2)_2(CF_2)_5CF_3$, $-(CH_2)_2(CF_2)_9CF_3$, $-(CH_2)_3(CF_2)_4CF_3$, $-(CH_2)_2(CF_2)_2(CF_3CF_2CF_2)CF(CF_2)_2CF_3$, $-C_8F_{17}$, $-C_9F_{19}$, $-C_{10}F_{21}$, $-C_{11}F_{23}$, and $-C_{12}F_{25}$. The thienopyrazine group may be incorporated into a homopolymer, or a copolymer comprising additional monomeric units. In some cases, the thienopyrazine group may be incorporated into a polymer comprising aryl or other heteroaryl groups within the polymer backbone. In some cases, the thienopyrazine group may be incorporated into a polymer comprising alkenyl or alkynyl groups within the polymer backbone.

In some cases, the polymer comprises the structure,

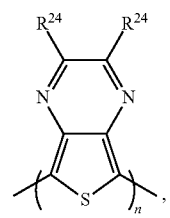

wherein:

each $R^{24}$ can be the same or different and is hydrogen, alkyl, heteroalkyl, aryl, or heteroaryl, any of which is optionally substituted with one or more fluorine atoms; and n is greater than 1.

The polymer may include any arrangement of thienopyrazine groups and aryl and/or heteroaryl groups. In some cases, the polymer may include at least one, at least, two, at least 3, at least 4, at least 5, or greater, groups positioned in between thienopyrazine groups along the polymer backbone. For example, heteroaryl groups such as thiophene groups may be positioned in between the thienopyrazine groups along the polymer backbone. In some embodiments, aryl groups such as fluorine groups (e.g., dialkylfluorene groups) may be positioned in between the thienopyrazine groups along the polymer backbone.

In some cases, the polymer comprises the structure,

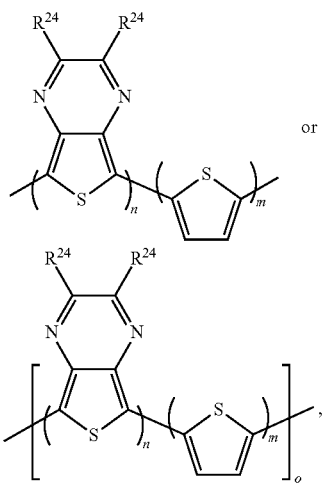

or wherein:
each $R^{24}$ can be the same or different and is hydrogen, alkyl, heteroalkyl, aryl, or heteroaryl, any of which is optionally substituted with one or more fluorine atoms; and
n, m, and o are independently 1 or greater.

In some cases, the polymer comprises the structure,

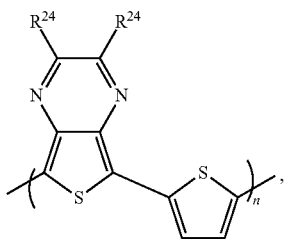

wherein:
each $R^{24}$ can be the same or different and is hydrogen, alkyl, heteroalkyl, aryl, or heteroaryl, any of which is optionally substituted with one or more fluorine atoms; and
n is greater than 1.

In some cases, the polymer comprises the structure,

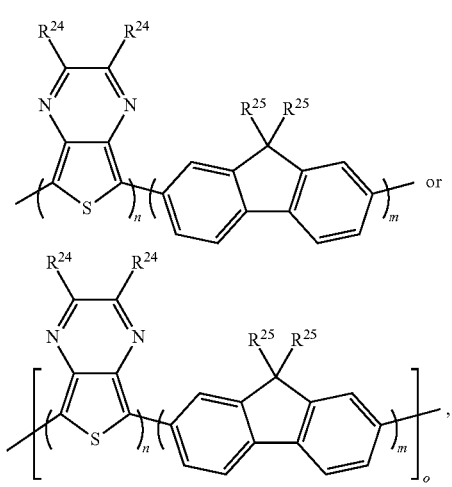

wherein:
each $R^{24}$ or $R^{25}$ can be the same or different and is hydrogen, alkyl, heteroalkyl, aryl, or heteroaryl, any of which is optionally substituted with one or more fluorine atoms; and
n, m and o are independently 1 or greater.

In some cases, the polymer comprises the structure.

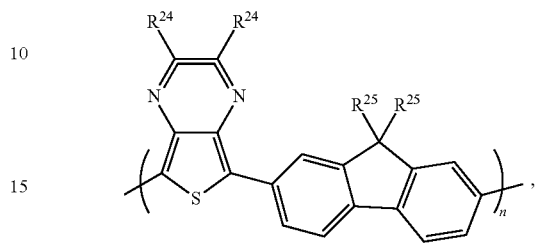

wherein:
each $R^{24}$ or $R^{25}$ can be the same or different and is hydrogen, alkyl, heteroalkyl, aryl, or heteroaryl, any of which is optionally substituted with one or more fluorine atoms; and
n is greater than 1.

In some embodiments, the polymer has the structure,

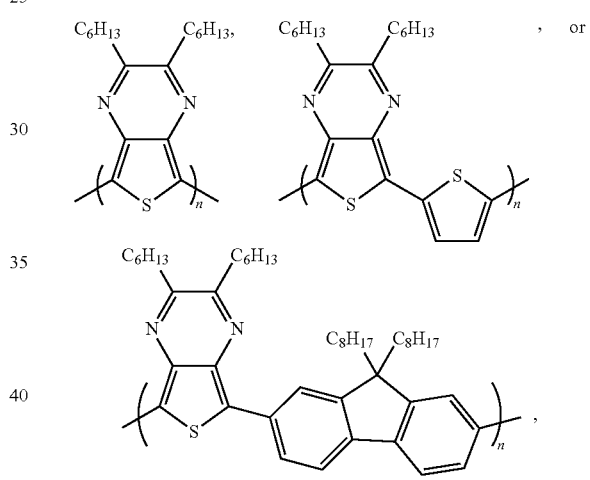

wherein n is greater than 1.

For any of the polymer structures described herein, n, m, or o may be less than about 10,000, or between 2 and about 10,000, between about 10 and about 5000, between about 50 and about 3000, or between about 100 and about 1000.

In some embodiments, the polymer may comprise one monomer (e.g., a "homopolymer"). In some embodiments, the polymer may comprise a plurality of monomers. In some embodiments, the polymer may comprise more than one monomer (e.g., a "copolymer") with the monomers forming the copolymer arranged in an arranged or random fashion. In one embodiment, the polymer may comprise more than one type of monomer block (e.g., a "block co-polymer").

In some embodiments, polymers of the present invention comprise at least one end-capping group. The term "end-cap" or "end-capping group" is known in the art and refers to a monomeric group which is placed at the terminal end of a polymer chain. In some embodiments, the end-capping group may be used to tune the electronic and/or optical properties of the polymer. Also, the end-capping group may be used to tune the solubility of the polymer (e.g., PEG groups, charged groups). Furthermore, end-capping may provide an efficient way to obtain a polymer having a particular desired length, such as a low molecular weight polymer. In some cases, the end-capping group may be alkyl, cycloalkyl, heteroalkyl, aryl, heteroaryl, substituted derivates thereof, or combinations thereof. In some embodiments, a polymer of the invention comprises a conjugated backbone, pendant side chains, and at least one end-capping group.

In some embodiments, a polymer may comprise a targeting or other biological entity which may be useful in applications where the polymers are used for the determination of analytes and/or biological target molecules. For example, the end-capping group of a polymer may be a targeting moiety for cancer, and the polymer may be used in an application for determining, treating, and/or imaging cancer in a subject. Groups which may be suitable for such applications are described herein, in connection with functionalizing the surface of an emulsion (e.g., see those described for "surface-altering moieties"). The targeting of other biological entity may be fluorophobic or fluorophilic. In embodiments where the targeting or other biological entity is fluorophobic and the polymer is fluorophilic, the targeting or other biological entity may arrange itself at or near a fluorous/non-fluorous solvent interface (e.g., at the surface of emulsion droplets).

Those of ordinary skill in the art will be aware of methods and techniques for synthesizing the monomers and the polymers (e.g., luminescent polymers) of the present invention. In some embodiments, the polymer may be synthesized using standard palladium-catalyzed techniques. For example, poly (phenyleneethynylene)s may be synthesized by palladium-catalyzed cross coupling between dihaloaryl monomers and diacetylene monomers. Bicyclic ring systems (e.g., iptycenes, pentipeptycenes) of the invention may be synthesized using known routes, for example, via Diels-Alder reactions.

In some embodiments, the polymerization method makes use of known cross-coupling reactions. For example, in some embodiments, the first monomer and the second monomer may be polymerized using Sonogashira-Hagihara cross-coupling polymerization (e.g., see FIG. 7). Those of ordinary skill in the art will be aware of other suitable methods and systems for synthesizing the polymers of the present invention. In some cases, the catalyst is a palladium catalyst. In some cases, the catalyst is provided in an amount of or less than an amount of about 0.1 mol %, about 0.2 mol %, about 0.3 mol %, about 0.4 mol %, about 0.5 mol %, about 1 mol %, about 2 mol %, about 3 mol %, about 4 mol %, about 5 mol %, about 6 mol %, about 7 mol %, or about 8 mol %, about 10 mol %, about 12 mol %, or about 15 mol %.

In some embodiments of the present invention, methods of forming a polymer (e.g., a luminescent polymer) are provided, wherein the method comprises the use of a biphase technique. In some cases, the biphase technique comprises providing a fluorous phase (e.g., involving a fluorous solvent) and a non-fluorous phase (e.g., involving an organic solvent). A catalyst (e.g., a palladium catalyst) and a first type of monomer may be contained in the non-fluorous phase, and a second type of monomer may be contained in the fluorous phase. The two phases may be mixed (e.g., via agitation, heating, etc.) under conditions and for a period of time such that the polymer forms (e.g., comprising a least a portion of first type of monomer and at least a portion of the second type of monomer). In some cases, the two phase solution may be mixed under conditions such that a single phase solution forms. Following polymerization the fluorous phase and the non-fluorous phase may be allowed to separate (e.g., by cooling the solution, allowing the materials to phase separate by sitting for a period of time, etc.). The polymer (e.g., in embodiments where the polymer is fluorous-soluble) can then be isolated from the fluorous phase. In some cases, the method advantageously allows for isolation of a fluorous-soluble polymer from a fluorous phase without the need for further purification. This is, at least in part, because the catalyst may be contained in the non-fluorous phase, and, after phase separation, the polymer has been isolated from the catalyst.

Biphase chemical techniques and methods will be known to those of ordinary skill in the art, as in Horvath, Acc. Chem. Res, 1998, 21, 641-650. In some cases, a single phase solution (e.g., comprising a fluorous phase and a non-fluorous phase) may be formed by heating the solvent system. For example, perfluoromethylcyclohexane and toluene form a single phase solution at temperatures greater than about 70° C. In some embodiments, the system comprising a fluorous phase and a non-fluorous phase may be heated to or at temperatures greater than about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., or higher. The two phases may be mixed for a period of time about or greater than about 30 minutes, about 1 hour, about 2 hours, about 4 hours, about 8 hours, about 12 hours, about 18 hours, about 24 hours, about 2 days, about 3 days, about 4 days, about 5 days, about 6 days, about 1 week, or greater.

In some embodiments, the first monomer is substantially insoluble in fluorous solvents and/or is substantially soluble is non-fluorous solvents. In some embodiments, the second monomer is substantially insoluble in non-fluorous solvents and/or is substantially soluble in fluorous solvents. In some cases, the first monomer does not form a homopolymer under the reaction conditions and/or the second monomer does not form a homopolymer under the reaction conditions (e.g., the first monomer is not polymerizable with itself and/or the second monomer is not polymerizable with itself, under the reaction conditions).

According to some aspects of the present invention, emulsions are provided. In some embodiments, an emulsion comprises a non-fluorous continuous phase and a fluorous non-continuous phase. In some cases, the fluorous non-continuous phase contains a polymer (e.g., as described herein). In some cases, the fluorous non-continuous phase contains a luminescent polymer. In some cases, the luminescent polymer has a quantum yield of greater than about 50%, greater than about 60%, greater than about 70%, greater than about 75%, greater than about 80%, greater than about 85%, greater than about 90%, greater than about 95%, or greater.

In some embodiments, however, as mentioned above, a polymer (e.g., a luminescent polymer and/or a polymer as described herein) may be modestly soluble in a fluorous solvents but also have an affinity for a second solvent (e.g., a non-fluorous continuous phase). Accordingly, in such embodiments, the luminescent polymer may be arranged at the interface between the fluorous and the non-fluorous phase.

Without wishing to be bound by theory, in some embodiments of the present invention, where the polymer comprising a plurality of fluorous-soluble pendant groups (e.g., perfluoroalkyl chains) and a plurality of fluorophobic chains (optionally hydrophobic or hydrophilic, for example, ether chains), the polymer may be able to itself act as a surfactant and/or organize at the interface of a two-phase systems (e.g., at the surface of emulsion droplets). For example, if a polymer of the present invention comprises a plurality of ether pendant groups, and a plurality of perfluoroalkyl chains, the perfluoroalkyl chains and the ether chains may be oriented on different sides of the polymer chain, and the polymer may oriented itself such that the perfluoroalkyl chains are directed toward the fluorous solvent and the ether chains are directed towards a non-fluorous solvent (e.g., water).

Emulsion chemistry and techniques will be known to those of ordinary skill in the art. The term "emulsion," as used herein, is given its ordinary meaning in the art and refers to a stable mixture of at least two immiscible liquids. In general, immiscible liquids tend to separate into two distinct phases. An emulsion can be stabilized by the addition of a surfactant which functions to reduce surface tension between the at least two immiscible liquids. In some embodiments, emulsion described herein include a discontinuous or disperse phase (i.e., the isolated phase stabilized by a surfactant) formed of a fluorophilic (e.g., fluorous solvent) substance. The continuous phase may be formed of a fluorophobic substance (e.g., non-fluorous solvent). In some embodiments, emulsions described herein are macroemulsions. Macroemulsions are emulsions that are kinetically stable, as compared to microemulsions, which are thermodynamically stable and undergo spontaneously formation. In some cases, a microemulsion may include droplets having an average diameter of less than about 50 nm.

In some embodiments, emulsion of the invention are stable for at least about 1 minute, at least about 5 minutes, at least about 10 minutes, at least about 20 minutes, at least about 30 minutes, at least about 40 minutes, at least about 1 hour, at least about 2 hours, at least about 6 hours, at least about 12 hours, at least about 1 day, at least about 1 week, at least about 1 month, or at least about 2 months, at a temperature of about 25 degrees Celsius and a pressure of 1 atm. As used herein, a "stable emulsion" means that greater than about 90%, about 93%, about 95%, about 97%, about 99%, or greater, of the droplets of the emulsion do not coalesce, e.g., to form larger droplets.

In some embodiments, the stability of the emulsions may be determined based on the zeta-potential of the emulsions. Generally, emulsions having a zeta-potential of about ±40 mV or greater are considered to have good stability. In some cases, the zeta-potential may be about ±30 mV, about ±35 mV, about ±40 mV, about ±45 mV, about ±50 mV, about ±55 mV, about ±60 mV, about ±65 mV, about ±70 mV, or greater.

In some embodiments, the emulsions of the invention include discontinuous fluorous droplets in a continuous, non-fluorous phase. This means that separate, isolated regions of droplets of an fluorous (e.g., fluorophilic) component are contained within a continuous non-fluorous (e.g., fluorophobic) phase. The discontinuous fluorous droplets in the non-fluorous phase typically may have an average cross-sectional dimension of greater than 25 nm. In some embodiments, the average cross-sectional dimension of the droplets is greater than 50 nm, greater than 100 nm, greater than 250 nm, greater than 500 nm, greater than 1 micron, greater than 5 microns, greater than 10 microns, greater than 50 microns, greater than 100 microns, greater than 200 microns, or greater than 500 microns, etc. In some embodiments, the average cross-sectional dimension of the droplets is between about 1 nm and about 100 um, between about 10 nm and about 10 um, between about 100 nm and about 1000 nm, between about 1 nm and about 1000 nm, between about 1 nm and about 500 nm, or between about 100 nm and about 500 nm. In some cases, the droplets of the emulsion may also be referred to particles, in the sense that the droplet contains a significant amount of polymer material, such that the droplet essentially becomes solid or semi-solid.

In some embodiments, the emulsions of the invention include a polymer that selectively organizes at the surface of the emulsion particle. In the case that the emulsion is between a fluorous phase and water, the polymer can present hydrophilic functionality at the interface directed into the water. Such constructs can be useful for the assembly of systems capable of interacting with biological molecules, cells, viruses of protein aggregates. In preferred embodiments the hydrophilic functionality attached to the polymer will contain a ligand or receptor specific to a biological molecule of interest. In some cases, a targeting moiety may be associated (e.g., through a bong) to a polymer containing emulsion will produce a change in the emission properties and allow for the detection of the biological molecules, cells, viruses of protein aggregates.

As used herein, "substantially," in connection with an polymer (or other material) being contained within solvent phase (e.g., a fluorous phase) means that at least about 75%, at least about 80%, or at least about 85%, at least about 90%, at least about 95%, at least about 96%, at least about 97%, at least about 98%, at least about 99%, at least about 99.5%, at least about 99.6%, at least about 99.7%, at least about 99.7%, at least about 99.9%, at least about 99.95%, at least about 99.99%, or more, of the polymer is contained within the solvent phase.

Those of ordinary skill in the art will be aware of methods and systems for forming emulsions. For example, non-limiting techniques include sonication, controlled shearing, membrane emulsification, microfluidic techniques, etc. In a particular embodiment, an emulsion is formed using sonication. For example, a fluorous solvent containing a polymer may be added to a non-fluorous solvent, optionally heated and/or optionally comprising a surfactant. The fluorous solvent may be added to the non-fluorous solvent under probe sonication.

In some embodiments, an emulsion of the present invention comprises at least one surfactant. The term "surfactant," is given its ordinary meaning in the art and refers to a molecule that, when combined with a first component defining a first phase, and a second component defining a second phase, will facilitate assembly of separate first and second phases. In some cases, a surfactant of the invention typically can have one or more main chains which are fluorophilic and one or more chains which are fluorophobic. In some cases, one end of the surfactant in fluorophilic and the other end is fluorophobic. In some cases, the surfactant may be a multi-block surfactant (i.e., having an alternating copolymeric structure or an (A-B-)$_n$ structure, i.e., ABA, ABAB, ABABA, ABA-BABA, etc.). In such cases, one block may be soluble in the fluorophilic phase of the emulsion and one block may be soluble in the other phase of the emulsion (e.g., the fluorophobic phase). In still other cases, additional components may be present within the surfactant.

Non-limiting examples of surfactants suitable for use with the invention include perfluoroheptaneic acid, perfluorooctanoic acid, perfluorononanoic acid, perfluorodecanoic acid, perfluoroundecanoic acid, perfluorododecanoic acid, perfluorotetradecanoic acid, perfluorohexadecanoic acid, perfluorooctadecanoic acid, perfluorosuccinic acid, perfluoroglutaric acid, perfluoroadipic acid, perfluorosuberic acid, perfluoroazelaic acid, perfluorosebacic acid, methyl perfluoroheptanoate, methyl perfluorooctanoate, methyl perfluorononanoate, methyl perfluorodecanoate, methyl perfluoroundecanoate, methyl perfluorododecanoate, methyl perfluorotridecanoate, methyl perfluorotetradecanoate, methyl perfluoropentadecanoate, methyl perfluorohexadecanoate, methyl perfluorooctadecanoate, dimethyl perfluorosuccinate, dimethyl perfluoroglutarate, dimethyl perfluoroadipate, dimethyl perfluorosuberate, dimethyl perfluoroazelate, dimethyl perfluorosebacate, perfluoro-1, 10-decanedicarboxylic acid, dimethyl ester, and dimethyl perfluorododecanedioate. In a particular embodiment, the surfactant is 2H,2H,3H,3H-perfluorononaoic acid, a surfactant which has been approved by the FDA for use as a component in human blood surrogate.

Figure 13:
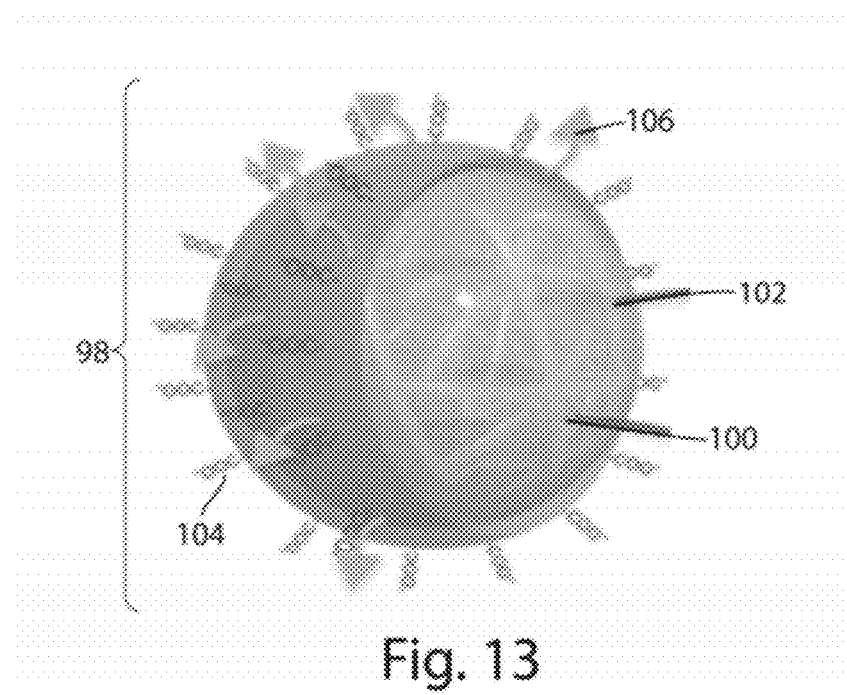
FIG. 13 shows a schematic illustration of an emulsion droplet comprising targeting ligands.

In some embodiments, the emulsion droplets comprise a plurality of surfactant molecules at or near the surface of the emulsion droplets, and the surfactant molecules provides a plurality of functional groups (e.g., carboxylic groups) at or near the surface of the emulsion droplets. The plurality of functional groups may be functionalized with one or more surface-altering moieties. The term "surface-altering moiety", as use herein, refers to moiety which is present on the surface of an emulsion droplet (or particle) and alters the surface of the moiety. In some cases, the surface-altering moiety may be associated with the droplet during and/or following formation of the droplet. For example, as shown in FIG. 13, a droplet 98 contains polymer 100, and optionally, fluorophore 102 (e.g., as described herein). The surfactant present on the surface of the droplet provides functional groups 104 (in this case, illustrated by COO⁻ groups). Surface-altering moieties 106 may be present on the surface of the droplet by association of a moiety with a functional group.

In some cases, the surface-altering moieties may be selected such that they aid in the use or application of the particles. For example, as described herein, the emulsions of the present invention may be used for application for determining, treating, and/or imaging of a condition and/or disease in a subject and/or tissue. Thus, the surface-altering moieties may be targeting moieties for determining, imaging, and/or treatment of a condition or disease in a subject and/or tissue. For example, the disease may be cancer (e.g., breast cancer) and the surface-altering moieties may be targeting ligands for cancer cells. In some embodiments, the subject is a human. Those of ordinary skill in the art will be able to select surface-altering moieties suitable for use in a specific application and non-limiting examples are described herein. In some cases, the surface-altering moiety is a targeting moiety for targeting a species in or on a tissue or a subject. In some cases, the surface-altering moiety may be fluorinated (e.g., as compared to the usual state of the targeting moiety, etc.) to aid in the solubility and/or association of the surface-altering moiety with the emulsion droplet. In some cases, however, the surface-altering moiety will be selected so as to not be soluble in the emulsion droplet, and thus, may be arranged at the interface between the two phases. Additionally, as described above, in some cases, the polymer contained in an emulsion may itself be associated with a targeting or other biological entity which may be useful in applications where the polymers are used for the determination of analytes and/or biological target molecules.

Figure 2:
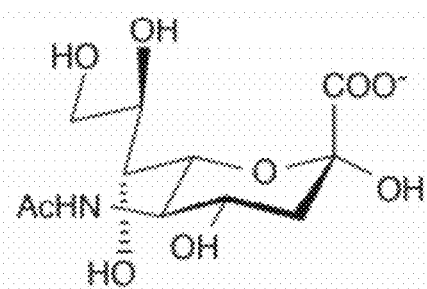
FIG. 2 shows the structure of sialic acid.

In some embodiments, the surface-altering moieties may comprise biological recognition entities. For example, a biological recognition entity may be capable of specifically interacting with a cell or species associated a cell. In some cases, the biological recognition entity may specifically associate with a cell membrane, bypassing other biological species at the surface of the cell. In some cases, the biological recognition entity may also target the nuclear membrane barrier. In one embodiment, the biological recognition entity may be capable of having a specific binding interaction with a target species in a cell. As used herein, "binding" can involve any hydrophobic, non-specific, or specific interaction, and the term "biological binding" refers to the interaction between a corresponding pair of molecules that exhibit mutual affinity or binding capacity, typically specific or non-specific binding or interaction. Biological binding defines a type of interaction that occurs between pairs of molecules including proteins, nucleic acids, glycoproteins, carbohydrates, hormones, and the like. Specific examples include protein/carbohydrate, antibody/antigen, antibody/hapten, biotin/streptavidin, biotin/avidin, enzyme/substrate, enzyme/inhibitor, enzyme/cofactor, protein/substrate, protein/ligand, lectin/carbohydrate, receptor/hormone, receptor/effector, complementary strands of nucleic acid (e.g., DNA and/or RNA), protein/nucleic acid, repressor/inducer, ligand/receptor, virus/ligand, etc. "Specific interaction" is given its ordinary meaning as used in the art, i.e., an interaction between pairs of molecules where the molecules have a higher recognition or affinity for each other than for other, dissimilar molecules. As a specific example, the surface-altering moieties may be a targeting moiety for a virus of bacteria, such as an influenza virus. Influenza viruses are known to bind to sialic acids, which is shown in FIG. 2. Accordingly, in some embodiments, the surface-altering moieties may comprise a perfluoroalkylate sialic acid. In some embodiments, the presence or absence of a bacteria, virus, and/or biomarker is determined.

In one embodiment, the biological recognition entity is a peptide (e.g., a cell-penetrating peptide, signal peptides targeting the nuclear membrane). In one embodiment, the biological recognition entity is a protein. In one embodiment, the biological recognition entity is a nucleic acid (e.g., DNA, RNA, an oligonucleotide). In one embodiment, the biological recognition entity is a small interfering RNA (siRNA). Other examples of suitable biological recognition entities include folic acid, carbohydrates, antibodies, and the like.

In another embodiment, the surface-altering moiety may be an moiety which quenches, reduces, or alters the luminescence of the polymer, and is released in the presence of a selected target. Upon release of the surface-altering moiety, the luminescence of the polymer may be restored. For example, in one embodiment, the surface-altering moiety may be an oligopeptide known to be degraded in the presence of matrix metalloproteases. The association of a plurality of oligopeptides with the emulsions and/or polymers of the present invention may cause the luminescence of the emulsion and/or polymer to be lowered, quenched, and/or altered (e.g., emission at a different wavelength). Upon release of the oligopeptide from the emulsion/polymer (e.g., upon exposure to a matrix metalloprotease), the luminescence of the emulsion and/or polymer may be restored. Accordingly, the presence of a matrix metalloprotease can be determined by determining the change in the luminescence of the polymer or emulsion.

Those of ordinary skill in the art will be aware of methods for associating surface-altering moieties with an emulsion droplet (or particle) of the present invention. Non-limiting examples of functional groups which may be present on the emulsion droplet and may be useful for attachment of a surface-altering moiety include amino groups, carboxylic groups, epoxide groups, maleimide groups, oxo groups, and thiol groups. Non-limiting examples of reactions which may be employed to associate a surface-altering moiety with a emulsion droplet include substitution, condensation, metal-catalyzed coupling, halogenation, pericyclic reactions, other bond-forming reactions, and the like. In a particular embodiment, the surface-altering moieties may be associated with the emulsion via condensation chemistry. For example, a plurality of carboxylic groups may be present on the surface of the emulsion droplet and the carboxylic groups may be reacted with a precursor to a surface-altering moiety comprising amine groups, thereby forming a plurality of amide linkages between the surface-altering moieties and the carboxylic groups of the emulsion droplet.

The emulsions of the present invention may find use in numerous applications. In some embodiments, methods are provided for determining, treating, and/or imaging a condition and/or disease in a subject. In some cases, the method comprises providing an emulsion, administering the emulsion to the subject, followed by imaging, determining, and/or treating a condition and/or disease in a subject. In some cases, the emulsion comprises a fluorous non-continuous phase, a non-fluorous continuous phase, at least one surfactant, at least one surface-altering moiety (e.g., associated with the emulsion droplets), and a polymer (e.g., as described herein) contained within the fluorous phase. In some cases, the polymer is luminescent.

In some cases, compositions for determining, treating, and/or imaging a condition or disease in a subject are provided. In some cases, the composition comprises an emulsion comprising a fluorous discontinuous phase, wherein a fluorescent entity (e.g., a luminescent polymeric material as described herein) is associated with the fluorous discontinuous phase, and a surface-altering moiety associated with the emulsion, for targeting a species in or on a tissue or a subject.

The luminescent polymer of the present may be used in various detection schemes for determining, treating, and/or imaging a condition or disorder in a subject. In some cases, the luminescent polymer may be used in a "turn-off" detection mechanism, wherein, in the presence of analyte (e.g., associated with the disease or disorder), the excited state of a luminescent polymer may interact with the analyte via photoinduced electron transfer to "quench" the luminescence (e.g., fluorescence, phosphorescence, etc.) of the polymer. "Quenching" of luminescence may occur when a chromophore such as a luminescent polymer in an excited state is exposed to an "acceptor" species that can absorb energy from the excited state chromophore. The excited state chromophore returns to a ground state due to nonradiative processes (i.e. without emitting radiation), resulting in a reduced quantum yield. Thus, the excited state chromophore can function as a "donor" species in that it transfers energy to the acceptor species. The acceptor species can be an external molecule (e.g., analyte) or an internal species such as another portion of the same polymer. For example, a "turn-off" detection method may be used to determine the presence and/or amount of an analyte. Alternatively, the luminescent polymer may be used in a "turn-on" detection mechanism, wherein, in the absence of analyte, the luminescent polymer may exist in a quenched state and substantially no emission signal, or a significantly reduced emission signal, is observed. In the presence of analyte, the polymer may interact with the analyte to produce an emission. In some cases, the "turn-on" fluorescence sensory scheme may be preferred since there are often fewer potential interferents that could cause a false positive with an emission increase or "turn-on" detection scheme.

In some embodiments, the polymers of the present invention may also be used in combination with an additional fluorophore, such as a small organic molecule, a fluorescent dye, green fluorescent protein, or the like, to enhance the performance of the fluorophore in cell imaging, cell monitoring, cell determination, etc. Such fluorophores may be unstable and may often undergo photobleaching, making the quantitative (and long-term) study of biological systems difficult. Conjugated polymers of the present invention may be useful in enhancing the photostability of fluorophore by, for example, undergoing fluorescence resonance energy transfer (FRET) with a fluorophore. The term "fluorescence resonance energy transfer" or "FRET" is known in the art and refers to the transfer of excitation energy from an excited state species (i.e., FRET donor) to an acceptor species (i.e., FRET acceptor), wherein an emission is observed from the acceptor species.

Figure 17:
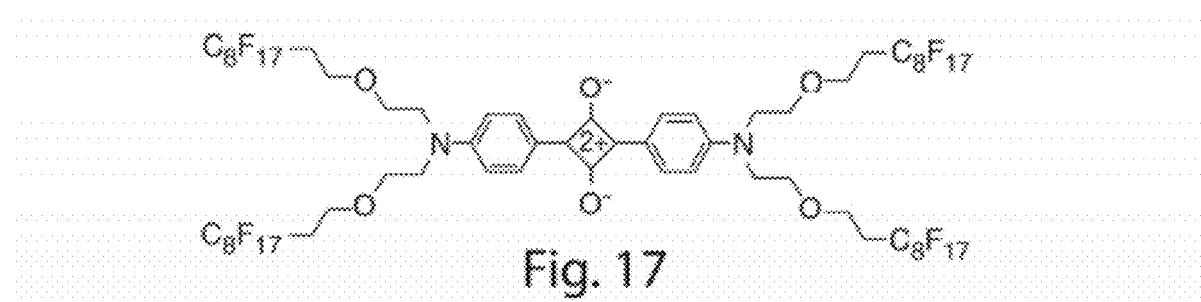
FIGS. 17 and 18 shows non-limiting examples of chromophoric systems, according to some embodiments.
Figure 18:
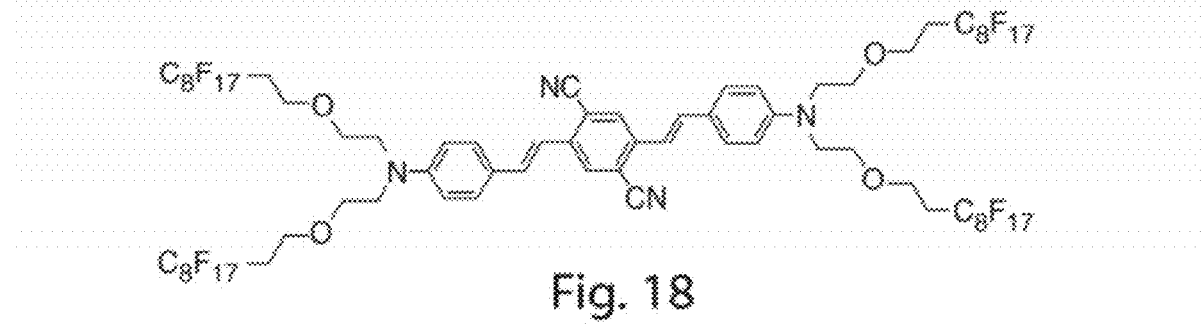
Figure 19:
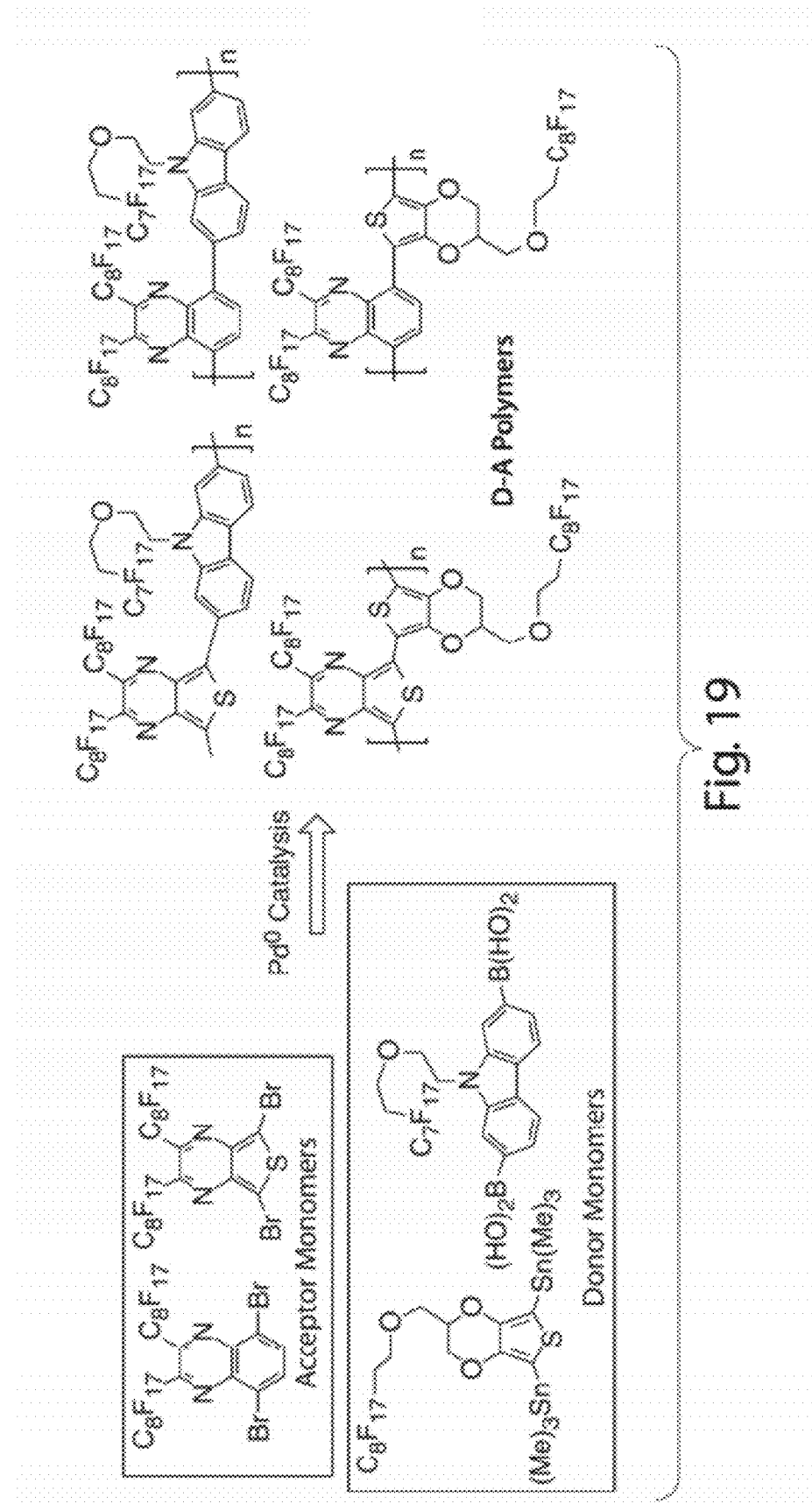
FIG. 19 shows non-limiting examples of chomophoric polymers, according to some embodiments.

According, in some embodiments, the compositions, emulsions, methods, and/or systems of the present invention further comprise at least one fluorophore. In some cases, the fluorophore may be comprised in the fluorous phase of the emulsion and/or composition. In some cases, a fluorophobic fluorophore may be fluorinated to increase the solubility of the fluorophore in a fluorous phase. Non-limiting examples of fluorophores which may be contained in the fluorous phase of an emulsion are shown in FIGS. 17, 18, and 19.

In one embodiment, the present invention provides a method for determining an analyte (e.g., a cell, a biological target, etc.), wherein the analyte interacts with a fluorophore. The species may be exposed to a conjugated polymer of the present invention and a fluorophore, wherein the polymer is a FRET donor and the fluorophore (e.g., small organic molecule, fluorescent dye, GFP) is a FRET acceptor. Exposure of the conjugated polymer to a source of energy may form an excitation energy, which may then be transferred to the fluorophore, causing an emission from the fluorophore. The analyte may be determined (e.g., observed, quantified, etc.) by the emission. Such methods may allow for reduced photobleaching in fluorophores and, in some cases, amplification of emission, allowing for more reliable quantification of fluorescence emission. In some cases, less than about 10 wt %, less than about 5 wt %, less than about 4 wt %, less than about 3 wt %, less than about 2 wt %, less than about 1 wt %, less than about 0.5 wt %, less than about 0.1 wt %, or the less, of the fluorophore is present as compared to the polymer.

In some embodiments, the polymer (e.g., contained in an emulsion, composition, film, device, etc.) may be excited using a one-, two-, three-, or more, photon method. In a particular embodiment, the polymer of the present invention may be excited using a two-photon method. Excitation using a two-photon methods will be known to those of ordinary skill in the art and generally involved the use of a chromophoric system. Generally, molecular systems having the largest two-photon absorption cross-sections exhibit symmetric structures with units having lower electronic affinities (electron donors, D) and those having higher electronic affinities (electron acceptors, A), linked by conjugated pi-systems. In some cases, the chromophoric system is present in a fluorous non-continuous phase of an emulsion.

Figure 15:
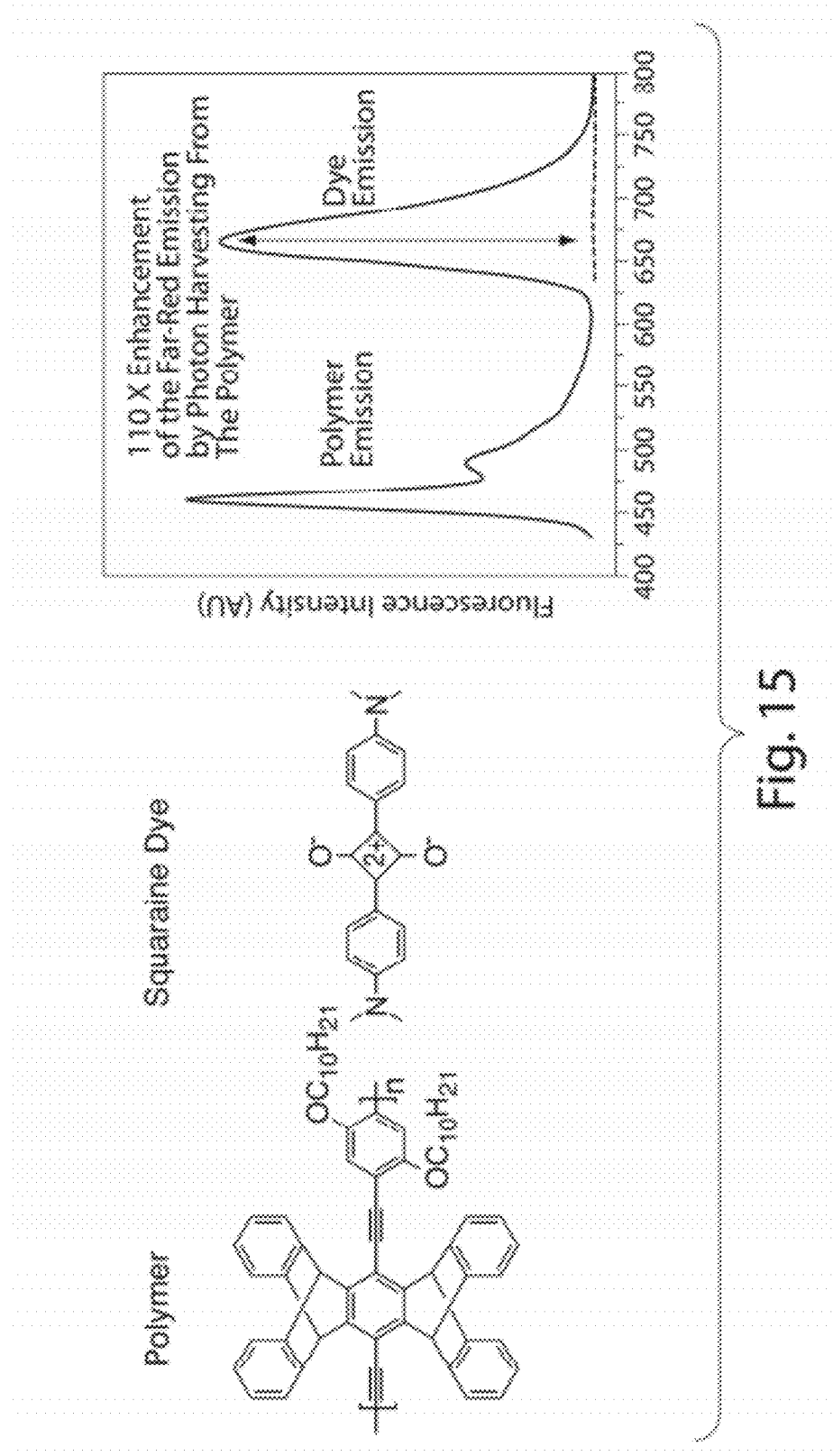
FIG. 15 shows a light harvesting polymer and far-red dye (0.5 wt %) and the thin film absorption (solid) and emission (dotted) spectra.

Suitable chromophoric systems for use with the polymers of the invention and for two-photon excitation will be known to those of ordinary skill in the art. Chromophoric systems having D-A-D are well suited to produce materials with high two-photon absorption cross-sections. Fluorous soluble analogs of known two-photon absorbing dyes may be produced (e.g., to aid in the solubility of the chromophoric system in fluorous solvents). For example, a fluorous analog of a well known D-A-D distyrylbenzene (FIG. 18) may be produced. The —$CH_2CH_2OCH_2CH_2$— spacer between the amine and the perfluorooctyl group may help minimize the inductive effects of the perfluorooctyl moiety on the donor nitrogens to maintain the high two-photon absorption cross-section. Far-red emitting small molecule two-photon absorbing dyes based on squaraine structures, for example, as shown in FIG. 15, are also known and hence fluorous analogs (FIG. 17) may be produced for direct two-photon excitation and as energy acceptors.

An advantage of polymer-based two-photon absorption, in some embodiments, is the fact that the harvested energy can undergo facile migration along the polymer backbone to an emissive dye. As a result, collection of light by a conjugated polymer and subsequent down conversion to a minority far-red dye has the prospects of producing a stronger two-photon response. Polymers with D-A structures (FIG. 19) are suitable candidates as strong two photon absorbers and have appropriate D-A-D triads. The strongly electron withdrawing nature of perfluoroalkyl groups make them natural candidates for integration into acceptor groups. The acceptor monomers shown in FIG. 19 should be accessible through condensation reactions between the phenyl- and thiophene-diamines and fluorous carbonyl compounds. These acceptor monomers make use of intermediates previously developed by in similar syntheses of non-fluorous analogs In some cases, the perfluoroalkyl groups may be isolated from the donor units to minimize or eliminate inductive effects that limit the electron donation and hence the two-photon absorption efficiency.

Figure 22:
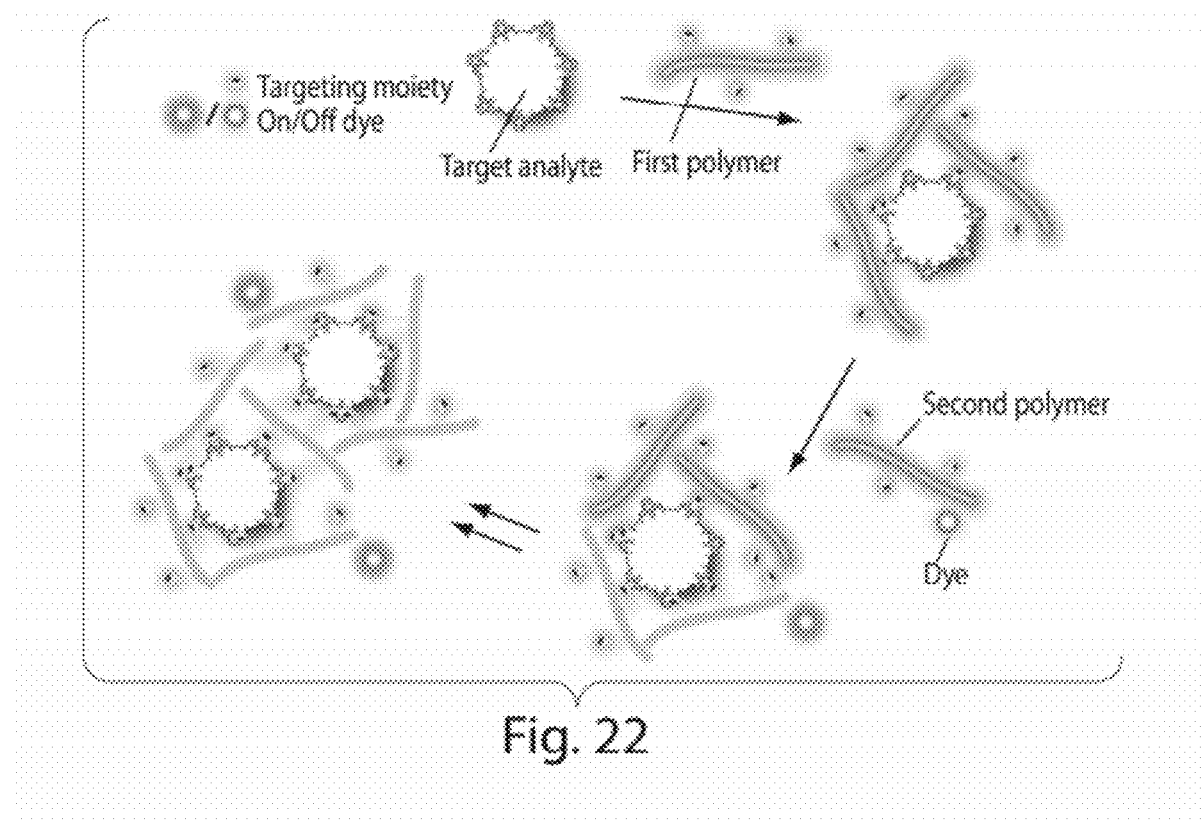
FIG. 22 shows a schematic of multivalent sensing.

In some embodiments of the present invention, the emulsions and polymer described herein may be used in sensing application, wherein the sensing comprises multivalent sensing. Multivalent sensing techniques and methods will be known to those of ordinary skill in the art. In some cases, a system for multivalent sensing comprises a first luminescent polymer comprising pendant groups (e.g., comprising a targeting moiety) and a second luminescent polymer with pendant groups associate with a low energy dye (e.g., a red dye) or a local low energy minimum in the polymer's band gap. As a specific example, the luminescent polymer may comprise pendent PPE groups associated with multiple sialic acid groups attached along the chain. When a mixture of the two luminescent polymers are exposed to a target analyte (e.g., a flu virus) which has multiple receptors associated with the target analyte (e.g., on the surface of the target analyte), the first and the second luminescent polymers may aggregate around the target analyte. When the first and second luminescent polymers are in close proximity to one another (e.g., via association with a target analyte), an the energy migration pathway may form between the polymers to the longer wavelength emitting dye or local minimum in the polymer's band gap may be enhanced (e.g., by harvests the energy of the polymers and channeling it to the dye). Thus, a "turn-on" response would aid in the sensing of the target analyte. See FIG. 22 for a schematic illustration of multivalent sensing.

In some embodiments, the present invention provides films of a polymer described herein, for example, formed on the surface of a material. The films may be incorporated into devices such as sensors. In some cases, the polymeric films exhibit enhanced optical properties such as luminescent lifetimes, amplified emissions, and enhanced stabilities.

Films may be formed using techniques known to those of ordinary skill in the art. For example, a film may be formed by spin-casting method, drop-casting method, dip coating method, roll coating method, screen coating method, a spray coating method, screen printing method, ink-jet method, and the like. In some cases, the thickness of the film may be less than about 1000 um, less than 100 um, less than about 10 um, less than about 1 um, less than about 100 nm, less than about 10 nm, less than about 1 nm, or thinner. In some cases, the film may have a thickness greater than 1 mm.

In some cases, the film may have a substantially uniform thickness over a large surface area (e.g., greater than 200 $nm^2$). A film having a "substantially uniform" thickness may refer to a film having a thickness which deviates less than about 20%, less than about 10%, less than about 5%, or, in some cases, less than about 2%, from an average thickness of the film. In some cases, the material may have a substantially uniform thickness over a surface area of at least about 200 $nm^2$, about 300 $nm^2$, about 400 $nm^2$, about 500 $nm^2$, or, in some cases, greater.

In one embodiment, the film comprising a polymer of the present invention has a quantum yield of at least about 0.05 times, about 0.1 times, about 0.15 times, about 0.2 times, about 0.25 times, about 0.3 times, about 0.4 times, about 0.5 times, or more, the quantum yield of the polymer in solution.

In some embodiments, a film comprising a polymer of the present invention may be incorporated into a device and system, for example an organic light emitting diodes (OLED), an organic field effect transistor (OFET), or a photovoltaic cell. In some embodiments, a thin film of a polymer as described herein may be incorporated into devices which, in some cases, comprises at least one addition layer of a non-fluorous soluble polymeric material. Without wishing to be bound by theory, devices formed comprising a first film comprising a fluorous soluble polymeric material and a second film comprising a non-fluorous soluble polymeric material may have a sharp boundary region between the two layers. That is, there may be minimal or essentially no bleeding of one polymeric material into the layer of the other polymeric material. This may be due to the inverse solubility of the two polymeric materials. The ability to form devices comprising multiple layers of polymer films with minimal or essentially no bleeding of the polymeric materials may be advantageous for applications in which efficiency and/or performance is improved with sharp boundary regions (e.g., OLEDs, photovoltaic devices, etc.).

Figure 3:
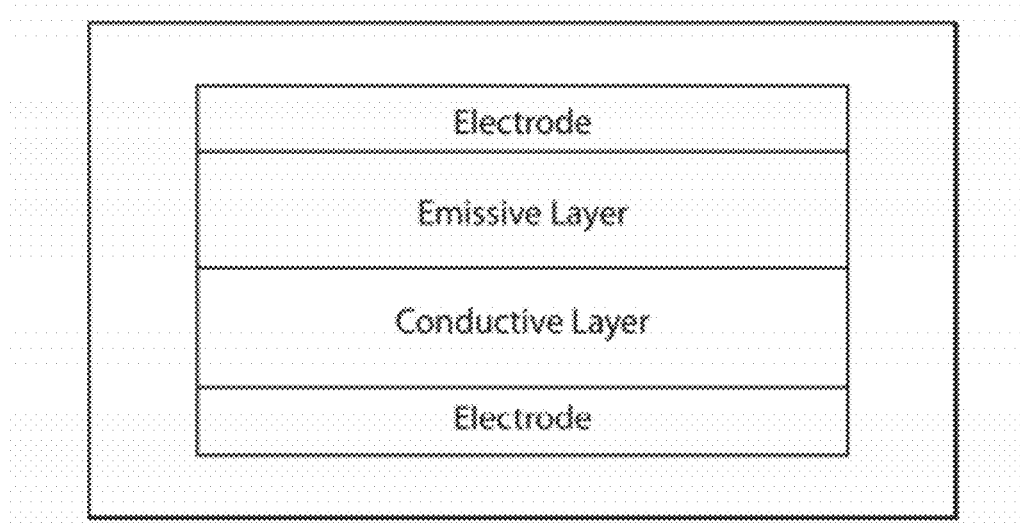
FIG. 3 shown a non-limiting schematic of an organic light emitting diode.

In some cases, the present invention provides an OLED comprising a thin film of a polymer described herein. OLED devices and methods for forming OLEDs will be known to those of ordinary skill in the art. A non-limiting example of an OLED device is shown in FIG. 3. In this schematic, an emissive layer and a conductive layer are sandwich between two electrodes. In some cases, the top electrode is the anode and the bottom electrode is the cathode, or vice versa. In some cases, the emissive layer may comprise a polymer of the present invention.

The present invention can also be used in a light-sensitive or light-activated device or sensors, such as a photodetector or a photovoltaic device. Incident light can, for example, interact with a polymer of the invention through a chromophore or an activation site. The exciton produced by such an interaction may then be transmitted, amplified, and/or detected by any suitable means (e.g., through electronic or photonic means), depending on the application. For example, energy may be collected by the activation site in the form of an exciton (e.g., a hole-electron pair), which then migrates to a separation site or a detection site, for example, to store charge or indicate the absorption of a photon. In one embodiment, an exciton in a polymer aggregate may act as an electron donor. Upon diffusion of the exciton to an interface with an acceptor (for example, titanium dioxide, a semiconductor, a polymer/molecular composition capable of accepting an electron, or an electron acceptor in liquid electrolyte), the polymer may transfer an electron to the acceptor, serving as an effective hole transport medium. In another embodiment, the polymer may be an electron acceptor. Upon diffusion of the exciton to an interface with a donor (for example, metal electrode, semiconductor, a polymer/molecular composition capable of donating an electron, or an electron donor in liquid electrolyte), an electron may be transferred to the polymer.

Figure 4:
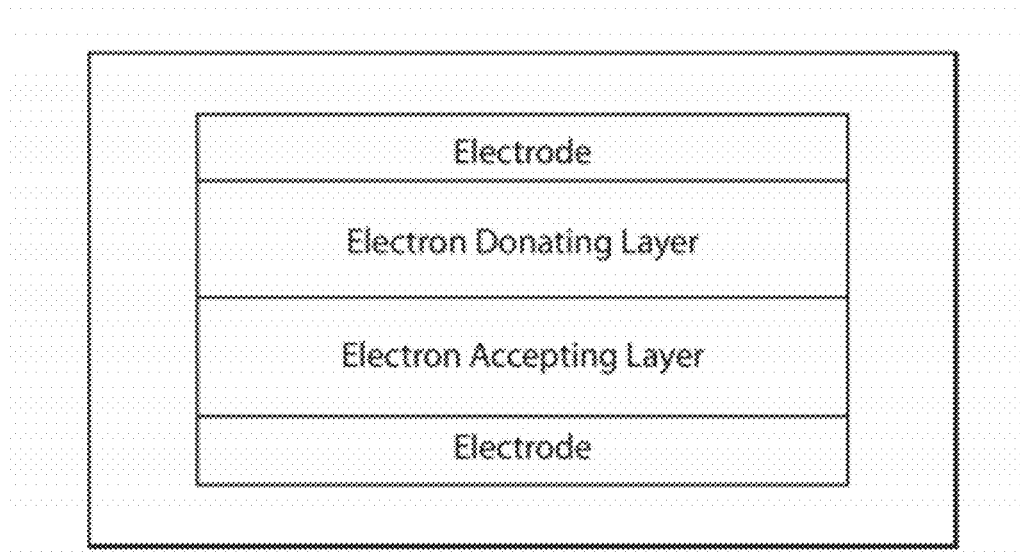
FIG. 4 shows a non-limiting schematic of a photovoltaic device.

A non-limiting schematic of a photovoltaic device is shown in FIG. 4. In this schematic, two materials (e.g., organic materials) are sandwiched between inorganic electrodes. Exposure of the device to incident light creates excitons (hole-electron pairs). The holes are trapped in electron donating layer and the electron are trapped in electron accepting layer.

In some embodiments, polymers described herein may in useful as semiconductor materials, including n-type materials or materials having more negative carriers (electrons) than positive carriers (holes). For example, the polymer may be a conjugated polymer semiconductor material comprising fluorine-containing groups as described herein and having enhanced electrochemical n-doping behavior, a relatively low band gap, as well as good solubility and air stability. Such materials may be advantageously high electron affinity for smooth electron injection, and may be low in cost and readily processed.

The compositions, polymers, and/or emulsions of the present invention may be administered to a subject using any known technique. Existing techniques include, for example, oral administration, direct injection into body tissue, topical or transcutaneous administration, and intravenous administration. In some cases, the compositions, polymers, and/or emulsions described herein are formulated as a pharmaceutical composition. The term "pharmaceutical compositions" or "pharmaceutically acceptable" compositions is given its ordinary meaning in the art and refers to a composition in comprising a therapeutically effective amount of one or more of the polymers or compositions described herein, formulated together with one or more pharmaceutically acceptable carriers (additives) and/or diluents. A pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

As used herein, a "subject" or a "patient" refers to any mammal (preferably, a human), and preferably a mammal that may requires or has undergone a joint replacement surgery. Examples include a human, a non-human primate, a cow, a horse, a pig, a sheep, a goat, a dog, a cat or a rodent such as a mouse, a rat, a hamster, or a guinea pig. Generally, of course, the invention is directed toward use with humans. The terms do not denote a particular age, and thus encompass adults, children, and newborn. In other cases, the invention may be directed towards use with dogs or horses.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone, 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, OR, N(R)$_2$, or a salt thereof, where each R is independently hydrogen, alkyl, alkenyl, heteroalkenyl, alkynyl, heteroalkynyl, aryl, heteroaryl, heterocycle, or the like. Where W is OR, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiocarbonyl" group. Where W is a SR, the formula represents a "thioester." Where W is SH, the formula represents a "thiocarboxylic acid." On the other hand, where W is alkyl, heteroalkyl, alkenyl, heteroalkenyl, alkynyl, heteroalkynyl, aryl, heteroaryl, etc., attached to the carbonyl via a carbon atom, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" refer to both unsubstituted and substituted amines, e.g., a moiety that can be represented by the general formula: N(R')(R'')(R''') wherein R', R'', and R''' each independently represent a group permitted by the rules of valence. An example of a substituted amine is benzylamine.

Any of the above polymers or groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

The function and advantage of these and other embodiments of the present invention will be more fully understood from the examples below. The following examples are intended to illustrate the benefits of the present invention, but do not exemplify the full scope of the invention.

Example 1

This example describes the synthesis and properties of two heavily fluorinated poly(p-phenylene ethynelene)s (PPEs), P1 and P2. (FIG. 5) Both polymers were shown to be highly fluorescent in solution and in thin film. Furthermore, P1, which displays selective solubility in fluorous solvents, can be synthesized via fluorous biphase polymerization, allowing for facile isolation/purification of the polymer after polymerization. (FIG. 6) The alkoxylated counterpart, P2, showed good solubility in organic solvents but was essentially insoluble in fluorous phase. Selective solubility of P1 in fluorous solvents can allow for the creation of a highly fluorescent and stable emulsion in water.

Figure 7:
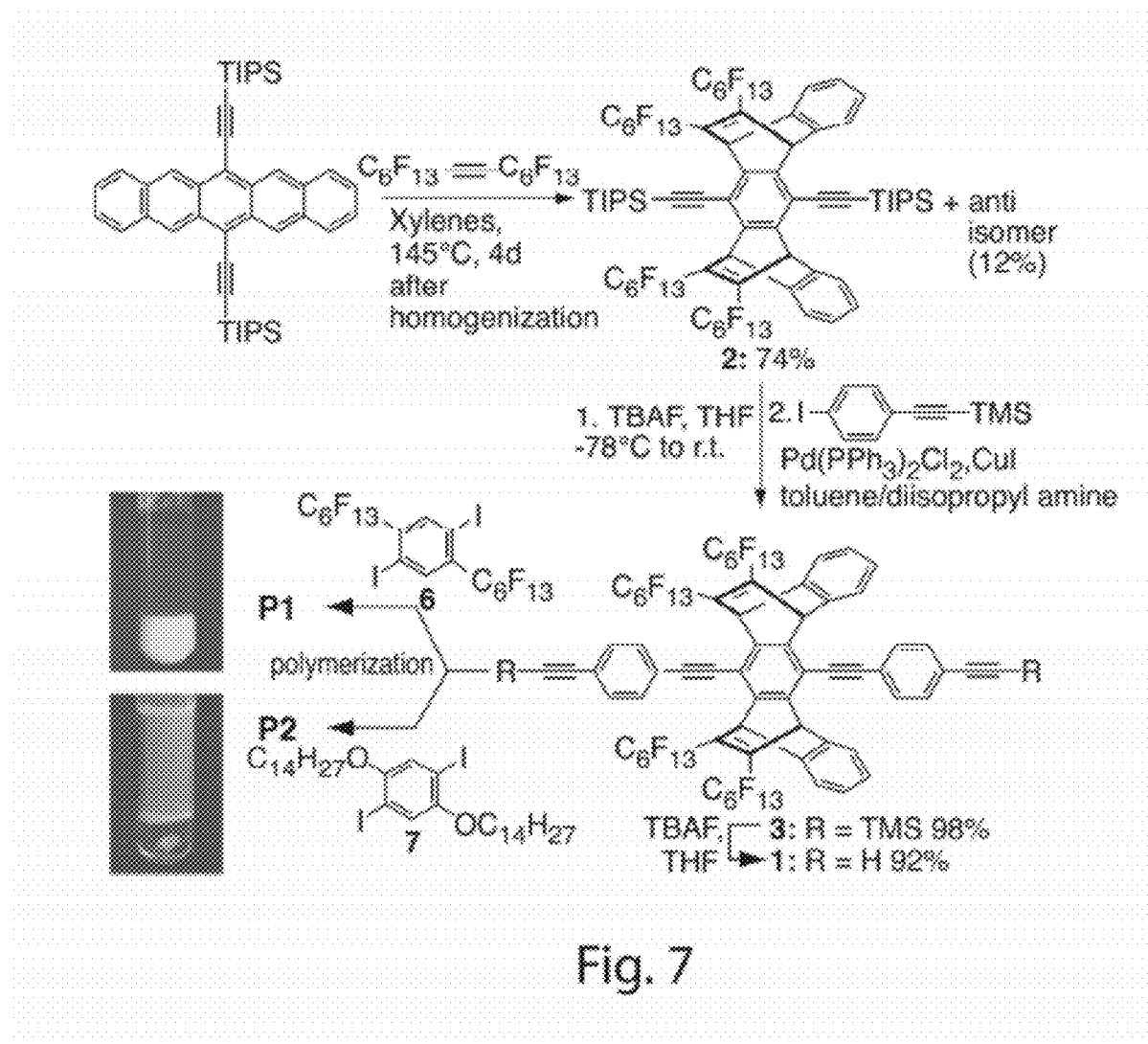
FIG. 7 shows non-limiting synthetic routes to P1 and P2.

The design principle of P1 was based on qualitative guidelines of fluorous compatibility and comprises a) majority fluorine content by weight and b) long perfluoroalkyl chains forming a sheath around the PPE backbone. Furthermore, a rigid, bulky architecture was desired to discourage aggregation of the polymer both in solution and in solid state. The synthesis of the monomer, 1, for a polymer that meets such requirements and the syntheses of P1 and P2 from 1 is outlined in FIG. 7, where the polymerization conditions involved mixing the monomers in 3:5:1 perfluoro(methylcyclohexane)/toluene/diisopropylamine in the presence of 5 mol % Pd(PPH$_3$)$_4$ and 7 mol % CuI at 85° C. for 4 days. The photographs in FIG. 7 show the reaction mixtures at the end of the reaction irradiated with hand-held ion-wave UV lamps.

When the pentacene derivative 2 was treated with an excess of perfluoro(7-tetradecyne) in xylenes at 145° C., no reaction was observed after 4 days. The lack of reactivity was attributed to the lack of solubility of perfluoro(7-tetradecyne) in xylenes even at elevated temperatures. When the reaction mixture was homogenized with a high-sheer mixer at 80° C. before raising the temperature to 145° C., the desired twofold Diels-Alder reactions took place, affording the desired di-adduct, 3, in 86% yield. The reaction gave the syn-isomer as the major product, with a 6:1 syn/anti ratio. This selectivity is in sharp contrast to the Diels-Alder reactions of 2 with hexafluorobutyne and DMAD, in which cases the anti-isomers are observed as major products. The anti isomer displayed sparing solubility in most organic solvents, while the syn isomer was highly soluble, and therefore the synthesis was carried forward using only the syn isomer.

Removal of the TIPS moieties gave the corresponding diacetylene 4. Sonogashira-Hagihara cross coupling polymerization under various conditions between the diacetylene and diiodode 6 gave only oligomeric products. The low degree of polymerization may be attributed to the sterically encumbered environment around acetylene moieties of 4. It was therefore envisioned that monomer 1, with reduced steric hindrance around the acetylene functional groups, could yield higher polymers.

When monomer 1 was subjected to Sonogashira-Hagihara cross coupling polymerization in toluene/diisopropyl amine solvent system with diiodode 6, higher molecular weight products were obtained, although the products were soluble in organic solvents. It was expected that more fluorous solvent condition for Sonogashira-Hagihara cross coupling reaction would yield polymers with higher molecular weights, which may subsequently render the material selectively soluble in fluorous solvents. When 5:3:2 toluene/perfluoro(methylcyclohexane)/diisopropyl amine was heated, it was observed that the solvent mixture became monophasic at 82° C., and, upon cooling, the fluorous phase separated out from the organic (toluene/diisopropyl amine) phase cleanly. The Sonogashira-Hagihara cross coupling polymerization between monomer 1 and 6 in this solvent system at 85° C. gave, upon cooling, a biphasic mixture in which bright blue fluorescence is localized in the fluorous layer (photograph, Scheme 1). Removal of the organic layer, followed by washing the fluorous layer with methanol, acetone, and ethyl acetate gave P1 in 87% yield. This constitutes a first example of a fluorous biphasic synthesis of a conjugated polymer. The polymer obtained in this manner was optically pure and was used without further purification for photophysical measurements. When monomer 1 was treated with co-monomer 7 under identical conditions, a complete reversal of solubility was observed, with the fluorescence of the product biphasic mixture localized in the upper organic phase. Removal of the fluorous layer, followed by precipitation of the organic layer into ethanol and washing the solids with acetone, gave P2 in 78% yield.

Figure 8:
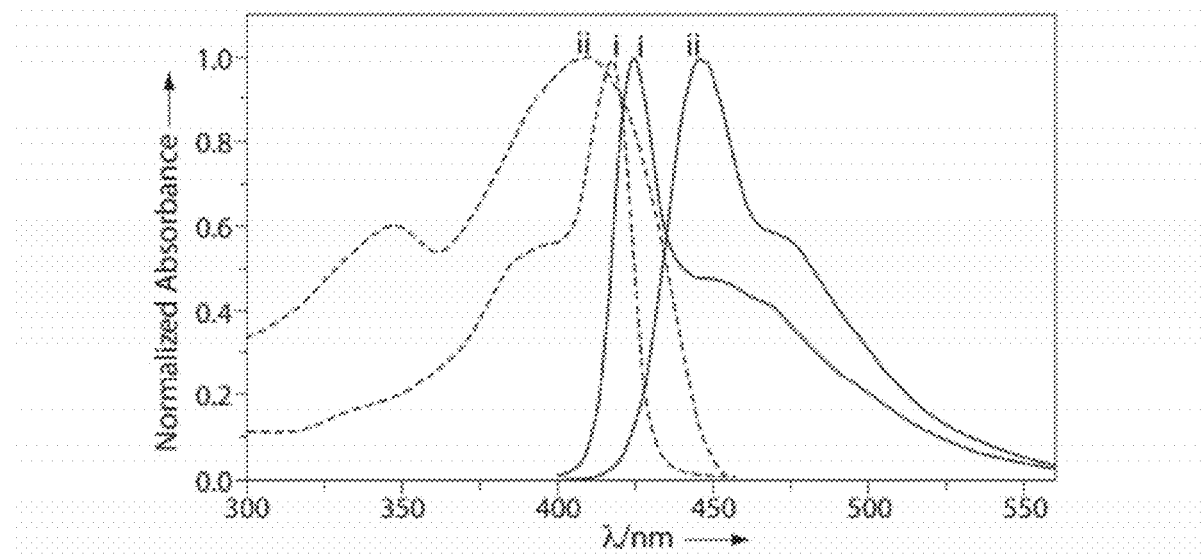
FIG. 8 shows the normalized absorption (dotted) and emission (solid) spectra of P1 (i) and P2 (ii).

FIG. 8 shows the normalized absorption (dotted lines) and emission (solid lines) spectra of i) P1 in perfluorodecalin and (ii) P2 in toluene. Fluorous soluble P1 displays band edge and emission maximum that are both blue-shifted in relation to P2. Small Stokes shift and sharp absorption and emission spectra of P1 (5-6 nm) suggested that the structure of the polymer in solution is highly rigid. Both P1 and P2 were highly fluorescent. Fluorous P1 had a quantum yield of 0.95 in perfluorodecalin and the organic-soluble P2 had a quantum yield of 0.84 in toluene. Furthermore, both polymers exhibited high quantum yields in thin film (0.32 for P1 and 0.42 for P2). The relatively lower thin-film quantum yield of P1 in comparison to P2 could be associated to the flat geometry of the co-monomer 6 relative to 7, resulting in higher degree of aggregation for P1 in solid state than P2.

Figure 9:
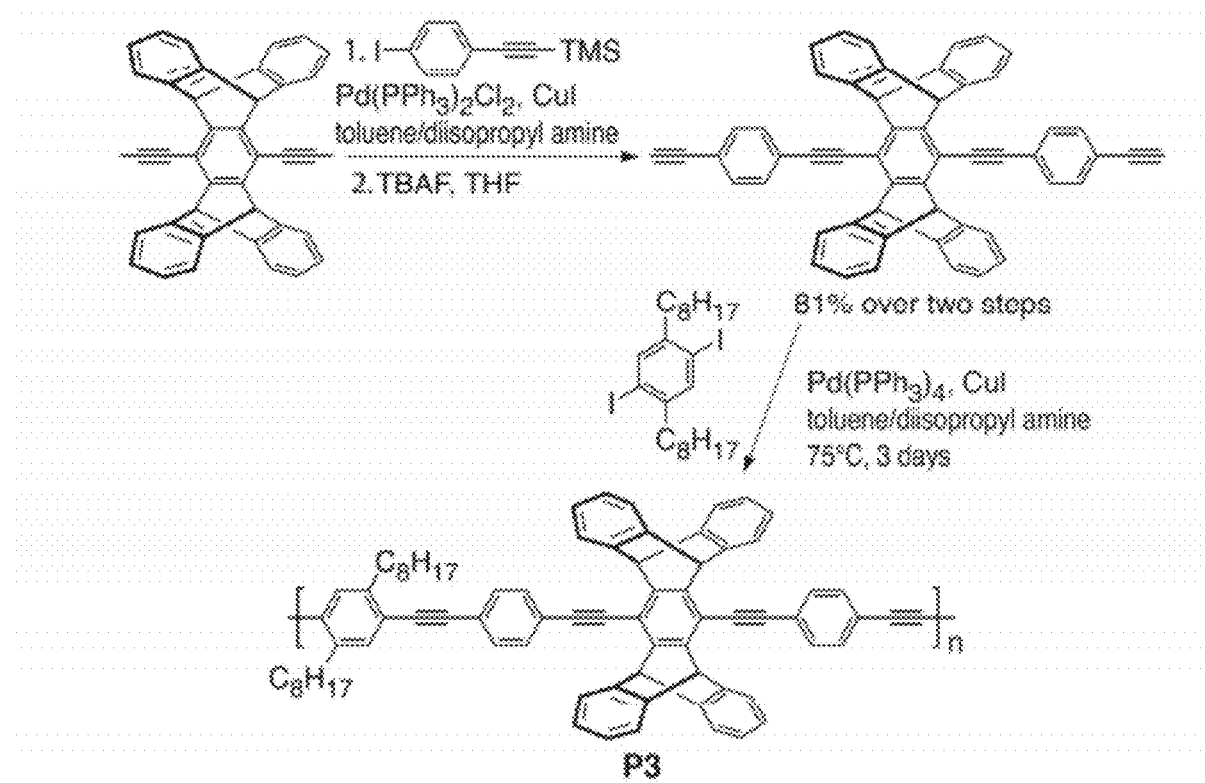
FIG. 9 shows the synthetic route to P3, according to a non-limiting embodiment.

To compare these properties to a non-fluorinated polymer, a new polymer, P3, featuring a rigid, three-dimensional architecture and dialkyl aryl moiety in the backbone, was synthesized as shown in FIG. 9. The solution absorption and emission spectra for P3 are described in Example 2 and shown in FIG. 21. P3 displayed a reduced solution quantum yield (0.48 in toluene) compared to P1 and P2. The thin-film emission spectrum of P3 showed a broad and red-shifted peak, suggesting large degrees of aggregation, whereas the thin-film emission spectra of P1 and P2 did not display significant shifts from their respective solution spectra, as described in Example 2 and shown in FIG. 10. Also, P3 was substantially insoluble in fluorous solvents.

While monomer 1 was substantially soluble in organic solvents including acetone, hexanes, chloroform, ethyl acetate, and THF, and substantially insoluble in non-polar fluorous solvents (such as FC-72, perfluoromethylcyclohexane, and perfluorodecalin), P1 was substantially soluble in those fluorous solvents but was substantially insoluble in organic solvents. Dynamic light scattering (DLS) analysis showed that the average length of P1 was 16 nm, a value which is the typical persistence length of long PPEs. DLS measurement in perfluorodecalin also showed similar length distribution. When P1 was end-capped with 1-bromo-4-tert-butylbenzene, no tert-butyl signals were observed in proton NMR spectrum, indicating high degree of polymerization (>20). The organic soluble P2 was analyzed by GPC, and was shown to have $M_n$=520 kDa, $M_w$=2,850 kDa, and PDI=5.48.

Figure 11A:
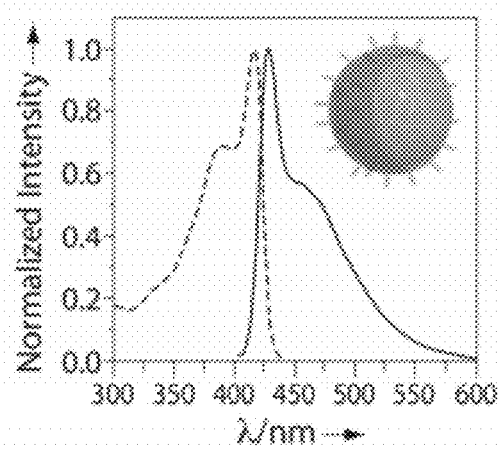
FIG. 11 shows absorption (dotted) and emission (solid) spectra of an emulsion of perfluorodecalin solution of P1 and b) photographs of the emulsion before (left) and after (right) irradiation with hand-held laboratory UV lamp.
Figure 11B:
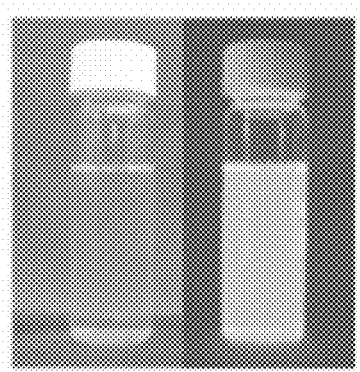

In order to make possible imaging and sensory applications of such fluorous-phase soluble fluorescent polymers, fluorous solutions of P1 were processed into a stable emulsion in water with easily modifiable functional groups adorning the surface. Perfluorodecalin, which has been approved by the FDA for use as a component in human blood surrogate, was chosen as the fluorous component of the emulsion. When a solution of P1 in perfluorodecalin was added slowly to a hot solution of 2H,2H,3H,3H-perfluorononanoic acid under probe sonication, a turbid and strongly fluorescent emulsion formed. Upon cooling, a relatively monodisperse emulsion was obtained with an average diameter of 245.8 nm and PdI of 0.099 as determined by DLS. The emulsion displayed absorption and emission maxima identical to P1. (FIG. 11) FIG. 11 shows (a) absorption (dotted) and emission (solid) spectra of the emulsion of perfluorodecalin solution of P1 in pH 7.4 PBS buffer (Q.Y. 0.58), and a pictorial representation of the emulsion particle, and b) a photograph of the emulsion before (left) and after (right) irradiation with hand-held laboratory UV lamp. The emulsion in PBS buffer was highly fluorescent, with a quantum yield of 0.58. Z-potential can be used to measure the stability of colloids in water. Higher surface charges generally discourage aggregation of particles. Colloids with surface potential of ±40 mV and higher are considered to have good stability. Emulsion of perfluorodecalin solution of P1 in water showed Z-potential of −57 mV with 13.2 mV deviation, indicating that the surfaces of the emulsion were sufficiently charged to confer good stability to the overall emulsion.

Two PPE's were synthesized from a novel, heavily fluorinated building block, 1, and demonstrated that, depending on the choice of the co-monomer, the solubility properties of the materials could be changed. Both polymers were highly fluorescent both in solution and in thin film. The fluorous phase soluble PPE, P1, could be processed into a stable emulsion in PBS buffer (pH 7.4). The emulsion involved a nontoxic fluorous solvent, was highly fluorescent, and has functional groups on the surface, which could be further modified.

Example 2

General.

All air- and moisture-sensitive synthetic manipulations were performed under an argon atmosphere using standard Schlenk techniques. Column chromatography was performed using ultra pure silica gel (SILIYCYCLE, 40~63 μm). NMR spectra were obtained on a Varian Mercury-300 spectrometer, and all proton chemical shifts are referenced to residual CHCl$_3$ or C$_6$D$_6$, and all fluorine chemical shifts are referenced to an external CFCl$_3$ standard. High-resolution mass spectra were obtained at the MIT Department of Chemistry Instrumentation Facility (DCIF) on a Bruker Daltronics APEX II3 Tesla FT-ICR-MS. Polymer molecular weights and polydispersity indexes were estimated by gel permeation chromatography (GPC) using a HP series 1100 GPC system. Polystyrene standards were used for calibration, and tetrahydrofuran (THF) was used as the eluent at a flow rate of 1.0 ml/min. Fluorescence spectra were measured on a SPEX Fluorolog-τ3 fluorimeter (model FL-321, 450 W Xenon lamp) using right-angle detection for solutions and front-face detection for thin films. Ultraviolet-visible absorption spectra were measured with an Agilent 8453 diode array spectrophotometer and corrected for background signal with a solvent-filled cuvette for solutions and glass slide for thin films. Fluorescence quantum yields of polymer solutions were determined by the optically dilute method using quinine sulfate in 0.1M H$_2$SO$_4$, coumarin 6 in ethanol, or 9,10-diphenylanthracene in hexanes as a standards and were corrected for solvent refractive index and absorption differences at the excitation wavelength. Fluorescence quantum yields of polymer thin films were determined using 9,10-diphenylanthracene in poly(methyl methacrylate) (PMMA) ($\Phi_F$=0.83). Dynamic light scattering (DLS) data for polymer length distribution was obtained from Wyatt Technologies DynaPro Titan using perfluoromethylcyclohexane and perfluorodecalin as solvents. The emulsion size and Z-potential was obtained from Malvern Zeta Sizer Nano ZS90.

Materials.

All solvents were spectral grade unless otherwise noted. Anhydrous toluene and tetrahydrofuran were obtained using a solvent purification system (Innovative Technologies). Perfluorohexyl iodide ($C_6F_{13}I$) was freshly distilled before use. Diisopropylamine was distilled over calcium hydride. Perfluoromethylcyclohexane and FC-77 (perfluorooctane) was purified according to literature procedures prior to use (e.g., see Glew, D. N.; Reeves, L. W. *J. Phys. Chem.* 1965, 615). All other chemicals were used as received. Solvents for polymerization (perfluoromethylcyclohexane, toluene, and diisopropylamine) were degassed via freeze-pump-thaw prior to use.

Synthesis

Scheme S1. Synthesis of perfluoro(7-tetradecyne) (S4).

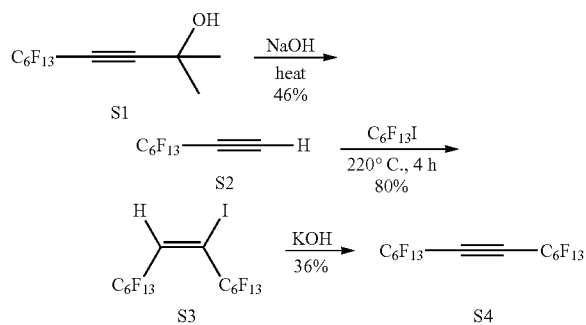

3,3,4,4,5,5,6,6,7,7,8,8,8-tridecafluorooct-1-yne (S2). A flame-dried 50 mL round-bottom flask equipped with distillation apparatus was charged with 5,5,6,6,7,7,8,8,9,9,10,10,10-tridecafluoro-2-methyldec-3-yn-2-ol (S1) (35.3 g, 88 mmol) and NaOH pellets (2.5 g, 61 mmol) under argon. The pressure was reduced to 400 mmHg and the flask was heated to 100° C. The crude product was collected over an hour in a receiving flask in a brine/ice bath. The product was washed 3 times with distilled water and was subsequently dried over $MgSO_4$. Removal of drying agent via filtration gave S2 (13.4 g, 46%) as a clear liquid. B.p. 92-94° C. $^1$H NMR (300 MHz, $CDCl_3$): δ 3.07 (t, $J_{H-F}$=5.7 Hz, 1H). 19F NMR (282 MHz, $CDCl_3$): δ −126.69 (2F), −123.39 (2F), −123.25 (2F), −121.83 (2F), −99.76 (2F), −81.33 (3F).

(Z)-1,1,1,2,2,3,3,4,4,5,5,6,6,9,9,10,10,11,11,12,12,13,13,14,14,14-hexacosafluoro-7-iodotetradec-7-ene (S3). Compound S2 (17.5 g, 50 mmol) and $C_6F_{13}I$ (33.4 g, 75 mmol) were added to a Parr bomb under $N_2$, and the reaction was sealed and heated to 220° C. The pressure of the reaction vessel increased initially to 95-100 psi, and was gradually reduced to 28 psi over 4 hours. The reaction was removed from heat and allowed to cool to room temperature before venting. The excess $C_6F_{13}I$ was distilled off at 10 mmHg, and the product (S3, 31.8 g, 80%) was obtained as a clear liquid by distillation at 6 mmHg. B.p. 99-101° C. (6 mmHg). $^1$H NMR (300 MHz, $CDCl_3$): δ 7.14 (t, $J_{H-F}$=12.6 Hz, 1H). 19F NMR (282 MHz, $CDCl_3$): δ −126.62 (4F), −123.35 (6F), −122.22 (2F), −121.18 (2F), −119.25 (2F), −111.34 (4F), −104.21 (2F), −81.21 (6F). HR-MS (EI): calcd for $C_{14}HF_{26}I$ 789.8702. found 789.8723.

Perfluoro(7-tetradecyne) (S4). A flame-dried 100 mL round-bottom flask was charged with anhydrous KOH (10 g, 170 mmol) under argon. Compound S3 (27.7 g, 35 mmol) was added, and the flask was equipped with a 15 cm vigreux column and a short-path distillation apparatus. The pressure was decreased to 6 mmHg, and the reaction mixture was placed in an oil bath pre-heated to 60° C. The reaction was heated slowly to 105° C. The product collected in the receiving flask was further purified by distillation at 6 mmHg (65-67° C.) and S4 (8.8 g, 38%) was obtained as a clear liquid. B.p. 65-67° C. (6 mmHg). $^1$H NMR (300 MHz, $CDCl_3$): blank. $^{19}$F NMR (282 MHz, $CDCl_3$): δ −126.43 (4F), −123.14 (4F), −122.83 (4F), −121.61 (4F), −102.44 (4F), −81.04 (6F).

Scheme S2. Synthesis of monomer 1.

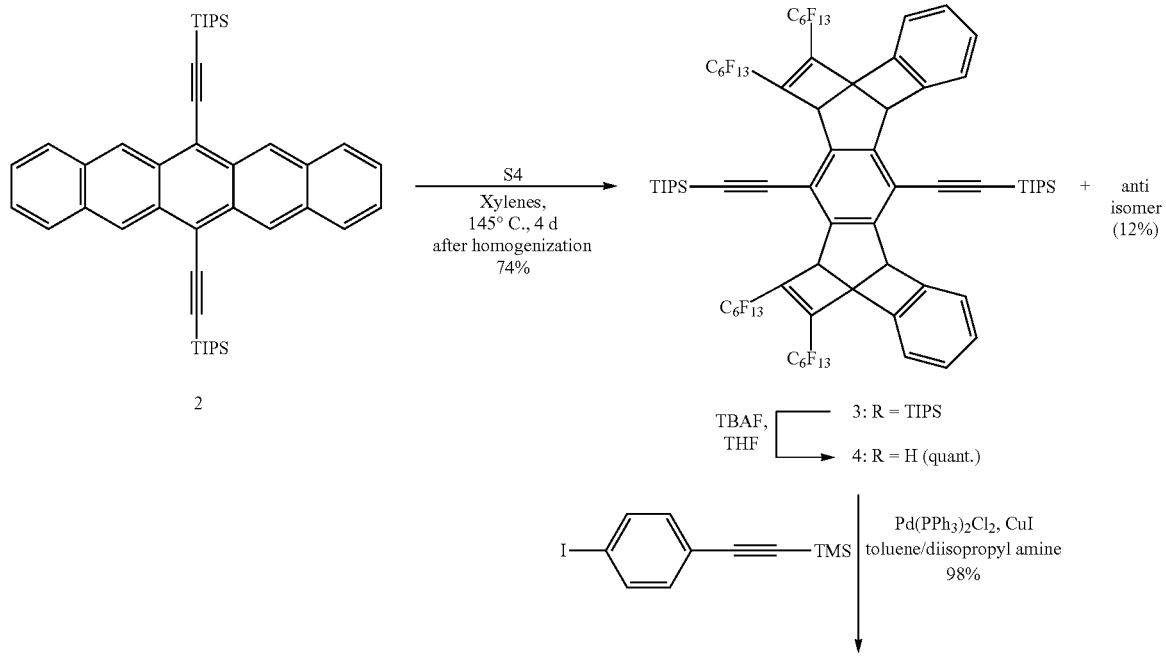

-continued

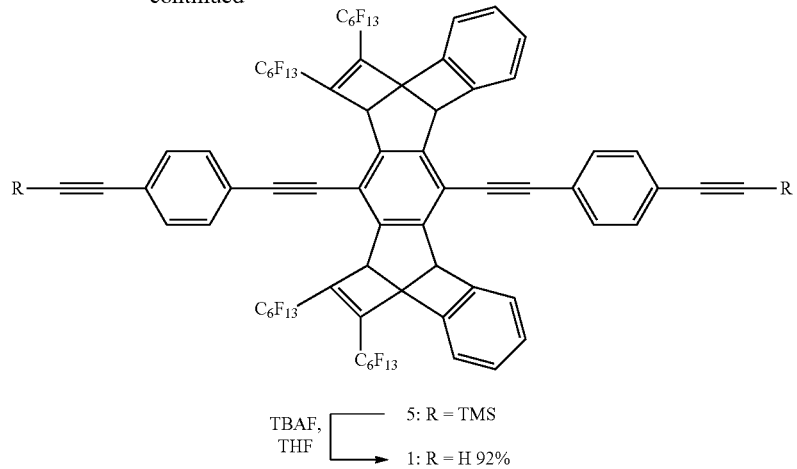

TBAF, THF
5: R = TMS
1: R = H 92%

Compound 3. A flame-dried 25 mL pressure tube was charged with 2 (640 mg, 1.0 mmol), S4 (2.0 g, 3.0 mmol), and xylenes (6 mL). The reaction mixture was degassed by bubbling argon through for 20 minutes while stirring. The reaction vessel was then placed in an oil bath at 80° C. After stirring for 20 minutes, the reaction mixture was homogenized with a high-sheer mixer for 20 seconds. The reaction vessel was then sealed and heated to 135° C. The color of the reaction changed gradually from deep blue to yellow over 4 days, at which point the reaction was allowed to cool to room temperature. Solvent and excess S4 was removed via distillation. The crude product was recrystallized in dichloromethane to give the anti isomer (217 mg, 11%). The mother liquor was concentrated and was purified by column chromatography (silica gel, 100% hexanes) to give the syn isomer, which was further purified by recrystallization in acetone to give 3 (1.14 g, 58%) as rod-like crystals. Anti: M.p.>300° C. $^1$H NMR (300 MHz, CDCl$_3$): δ 1.28 (s, 42H), 5.97 (s, 4H), 7.11 (dd, J=5.4 and 3.3 Hz, 4H), 7.36 (dd, J=5.4 and 3.3 Hz, 4H). 19F NMR (282 MHz, CDCl$_3$): δ −126.73 (4F), −123.41 (4F), −122.33 (4F), −119.58 (4F), −109.62 (4F), −81.33 (6F). HR-MS (EI): calcd for C$_{76}$H$_{38}$F$_{52}$Si$_2$ 1994.1676. found 1994.1624. Syn (3): M.p.>300° C. $^1$H NMR (300 MHz, CDCl$_3$): δ 1.28 (s, 42H), 5.97 (s, 4H), 7.03 (dd, J=5.4 and 3.3 Hz, 4H), 7.27 (dd. J=5.4 and 3.3 Hz, 4H). 19F NMR (282 MHz, CDCl$_3$): δ −126.77 (4F), −123.47 (4F), −122.50 (4F), −119.83 (4F), −109.50 (2F), −108.30 (2F), −81.47 (6F). HR-MS (EI): calcd for C$_{76}$H$_{38}$F$_{52}$Si$_2$ 1994.1676. found 1994.1624.

Compound 4. In a flame-dried 100 mL round bottom flask under argon, 3 (800 mg, 0.41 mmol) was dissolved in anhydrous THF (20 mL). The flask was cooled to −78° C. in dry ice/acetone bath. Tetrabutyl ammonium fluoride (0.85 mL, 0.85 mmol) solution was added dropwise. The reaction was stirred at −78° C. for 30 minutes. After warming up to room temperature, the reaction mixture was diluted with 10 mL ethyl acetate and 40 mL hexanes and subsequently passed through a plug of silica gel. The solvents were evaporated under reduced pressure and the crude product was purified by column chromatography (silica gel, hexanes as the eluent) to give 4 as white, foamy solids (690 mg, quantitative). M.p.>300° C. $^1$H NMR (300 MHz, CDCl$_3$): δ 3.73 (s, 2H), 5.90 (s, 4H), 7.04 (dd, J=5.4, 3.1 Hz, 4H), 7.37 (dd, J=5.4, 3.1 Hz, 4H). 19F NMR (282 MHz, CDCl$_3$): δ −126.70 (4F), −123.38 (4F), −122.47 (4F), −119.86 (4F), −108.89 (2F), −108.57 (2F), −81.34 (6F). HR-MS (ESI): calcd for C$_{54}$H$_{14}$F$_{52}$ 1673.0157 [M+Na]$^+$. found 1673.0192.

Compound 5. Flame-dried 10 mL Schenk flask was charged with 4 (415 mg, 0.251 mmol), 4-iodophenylethynyl trimethylsilane (180 mg, 0.600 mmol), Pd(PPh$_3$)$_2$Cl$_2$ (9.0 mg, 0.013 mmol), and copper(I) iodide (5.0 mg, 0.026 mmol). The flask was evacuated and back-filled with argon three times. Toluene (2 mL) and diisopropyl amine (1 mL), degassed by freeze-pump-thaw, was added via syringe. The reaction mixture was stirred at 40° C. for 12 hours. The reaction mixture was poured into 100 mL hexanes/100 mL aqueous hydrochloric acid (0.1 M). The organic layer was washed with saturated aqueous sodium bicarbonate solution followed by water, dried over MgSO$_4$, and solvent removed under reduced pressure. Crude product was purified by column chromatography (silica gel, 100% hexanes to 5% dichloromethane in hexanes) to give 5 as off-white solids (478 mg, 95%). M.p.>300° C. $^1$H NMR (300 MHz, CDCl$_3$): δ 0.30 (s, 18H), 5.95 (s, 4H), 7.05 (dd, J=5.4, 3.0 Hz, 4H), 7.40 (dd, J=5.4, 3.0 Hz, 4H), 7.56 (s, 8H). 19F NMR (282 MHz, CDCl$_3$): δ −126.53 (4F), −123.25 (4F), −122.32 (4F), −119.77 (4F), −108.53 (2F), −108.26 (2F), −81.17 (6F). HR-MS (EI): calcd for C$_{76}$H$_{38}$F$_{52}$Si$_2$ 1994.1676. found 1994.1624.

Monomer 1. In a 50 mL round bottom flask under argon, 5 (320 mg, 0.160 mmol) was dissolved in 10 mL anhydrous tetrahydrofuran. The solution was cooled to −78° C., and tetrabutylammonium fluoride (1.0 M in tetrahydrofuran, 0.340 mL, 0.340 mmol) was added dropwise. The reaction mixture was stirred at −78° C. for 30 minutes and warmed up to room temperature, and subsequently passed over a plug of silica gel, eluting with 25% ethyl acetate in hexanes. The solvents were removed under reduced pressure, and the crude product was purified by column chromatography (silica gel, 2% dichloromethane in hexanes) to give 2 as an off-white powder (276 mg, 93%). M.p.>300° C. $^1$H NMR (300 MHz, CDCl$_3$): δ 3.26 (s, 2H), 5.95 (s, 4H), 7.06 (dd, J=5.3, 3.0 Hz, 4H), 7.40 (dd, J=5.3, 3.0 Hz, 4H), 7.59 (s, 8H). $^{19}$F NMR (282 MHz, CDCl$_3$): δ −126.71 (4F), −123.42 (4F), −122.49 (4F), −119.84 (4F), −108.72 (2F), −108.33 (2F), −81.35 (6F). HR-MS (ESI): calcd for C$_{70}$H$_{22}$F$_{52}$ 1873.0783 [M+Na]$^+$. found 1873.0822.

Scheme S3. Synthesis of Monomer 6.

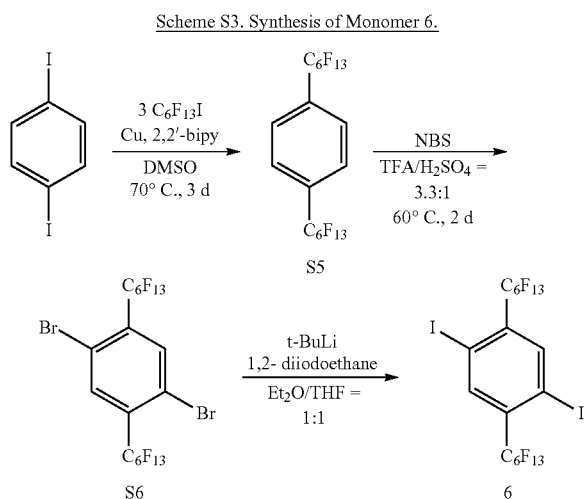

1,4-bis(perfluorohexyl)benzene (S5). A 100 ml Schlenk flask equipped with a stir bar was flame-dried and then charged with 1,4-diiodobenzene (3.30 g, 10 mmol), Cu powder (5.08 g, 80 mmol), and 2,2'-bipy (156 mg, 1 mmol). The flask was evacuated and back-filled with argon three times. Anhydrous dimethylsulfoxide (30 mL) was added via a syringe. Perfluorohexyl iodide (6.5 mL, 30 mmol) was added dropwise while stirring. Upon completion of addition, the reaction mixture was heated to 70° C. for 72 hours then removed from heat. The reaction mixture was poured into 100 mL $H_2O$/100 mL diethyl ether and stirred vigorously for 30 min. Solid residues were removed by filtration, and the organic layer was washed twice with dilute $NH_4OH$ solution, twice with water, dried over $MgSO_4$. The solvent was removed by evaporation under reduced pressure, and the resulting off-white solids were subjected to sublimation to give S5 as white solids (5.61 g, 78%). $^1$H NMR (300 MHz, $CDCl_3$): δ 7.77 (s, 4H). 19F NMR (282 MHz, $CDCl_3$): δ −126.58 (4F), −123.26 (4F), −122.15 (4F), −121.87 (4F), −111.71 (4F), −81.16 (6F).

1,4-dibromo-2,5-bis(perfluorohexyl)benzene (S6). A 50 mL round-bottom flask was charged with S5 (2.00 g, 2.80 mmol), trifluoroacetic acid (20.0 mL), and concentrated $H_2SO_4$ (6.0 mL). The reaction mixture was heated to 60° C., and N-bromosuccinimide (1.50 g, 8.43 mmol) was added in portions (250 mg/hr) over 6 hours. The stirring was continued for 48 hours at 60° C., and the reaction mixture was poured into iced water. Yellow precipitate was collected by filtration and were recrystallized twice in ethanol to give S6 as clear crystals (2.37 g, 97%). $^1$H NMR (300 MHz, $CDCl_3$): δ 7.94 (s, 2H) $^{19}$F NMR (282 MHz, $CDCl_3$): δ −126.60 (4F), −123.16 (4F), −122.31 (4F), −119.70 (4F), −108.01 (4F), −81.23 (6F). HR-MS (EI): calcd for $C_{18}H_2Br_2F_{26}$ 871.8090. found 871.8049.

1,4-diiodo-2,5-bis(perfluorohexyl)benzene (6). A flame-dried 100 mL round-bottom flask was charged with S6 (872 mg, 1.0 mmol), and evacuated and back-filled with argon three times. Anhydrous diethyl ether (8.0 mL) and anhydrous tetrahydrofuran (8.0 mL) were added via syringe. The flask was cooled to −78° C. and tert-butyllithium (1.5 M in pentanes, 3.0 mL, 4.5 mmol) was added dropwise over 15 minutes. The stirring was continued for 1.5 hours at −78° C. and diiodoethane (900 mg, 3.2 mmol) was added in one portion. The reaction was stirred in the dark at −78° C. for an additional hour and was removed from bath. The stirring continued for an additional 16 hours. Water (50 mL) was added to quench the reaction and the mixture was extracted with diethyl ether (2×50 mL). Organic layer was washed twice with NaOH solution (0.2 M), water, then brine, and solvent was removed under reduced pressure. Crude product was recrystallized in ethanol to give 6 (mg, %). M.p. 129-131° C. $^1$H NMR (300 MHz, $CDCl_3$): δ 8.14 (s, 2H). 19F NMR (282 MHz, $CDCl_3$): δ −126.31 (4F), −122.88 (4F), −121.83 (4F), −118.83 (4F), −107.47 (4F), −80.93 (6F). HR-MS (EI): calcd for $C_{18}H_2F_{26}I_2$ 965.7825. found 965.7859.

P1. A flame-dried 100 mL Schlenk vessel with teflon screw-on cap under argon was charged with monomer 1 (74.35 mg, 0.0402 mmol), monomer 6 (37.67 mg, 0.0390 mmol), $Pd(PPh_3)_4$ (2.30 mg, 0.0020 mmol), and CuI (0.40 mg, 0.0021 mmol). In a glove box, perfluoromethylcyclohexane (6 mL), toluene (10 mL), and diisopropyl amine (2 mL) were added. The Shlenk vessel was removed from the glove box and was stirred vigorously at 85° C. for 3 days. The reaction mixture, which was initially biphasic, became monophasic at c.a. 82° C. After allowing to cool down to room temperature, 10 mL of FC-77 was added. The fluorous (lower) phase, which was fluorescent, was subsequently removed and was washed 3 times with methanol (5 mL each), 3 times with ethyl acetate (5 mL each), and 3 times with acetone (5 mL each). Removal of the fluorous solvents under reduced pressure yielded P1 as a yellow film, which was detached from the flask via sonication in ethanol (20 mL). Ethanol was then removed under reduced pressure to give P1 (89.7 mg, 87%) as a bright yellow film. Prior to photophysical measurements, impurities were further removed from P1 via Soxhlet extraction ($CHCl_3$, 3 days) prior to drying the polymer under vacuum (2 days). Polymer length=16.3 nm. $^1$H NMR (500 MHz, FC-77, $C_6D_6$ external lock): δ 8.15-7.26 (br, 14H), 6.89 (br, 4H), 6.23 (br, 4H).

P2. A flame-dried 100 mL Schlenk vessel with teflon screw-on cap under argon was charged with monomer 1 (28.60 mg, 0.01505 mmol), monomer 7 (11.17 mg, 0.01500 mmol), $Pd(PPh_3)_4$ (0.80 mg, 0.00069 mmol), and CuI (0.20 mg, 0.0011 mmol). In a glove box, perfluoromethylcyclohexane (5 mL), toluene (10 mL), and diisopropyl amine (5 mL) were added. The Shlenk vessel was removed from the glove box and was stirred vigorously at 70° C. for 3 days. The reaction mixture, which was initially biphasic, became monophasic at c.a. 65° C. After allowing to cool down to room temperature the fluorous layer, which was not fluorescent, was removed. The organic layer was divided into two portions and each portion was added to 50 mL methanol. Yellow precipitates were collected via centrifugation, and the process was repeated three times with methanol, followed by three times with acetone to give P2 (27.6 mg, 78%) as bright yellow solids after drying under vacuum. Mn=520 kDa; PDI=5.48; DP=219 (THF-GPC). $^1$H NMR (500 MHz, $CDCl_3$): δ 7.67 (br, 8H), 7.44 (br, 4H), 7.11 (br, 6H), 6.00 (br, 4H), 4.12 (br, 4H), 1.93 (br, 4H), 1.61 (br, 4H), 1.44 (br, 4H), 1.26 (br, 36H), 0.84 (t, 6H). $^{19}$F NMR (282 MHz, $CDCl_3$): δ −126.66 (4F), −123.37 (4F), −122.38 (4F), −119.71 (4F), −108.72 (2F), −108.19 (2F), −81.32 (6F).

Scheme S4. Synthesis of P3.

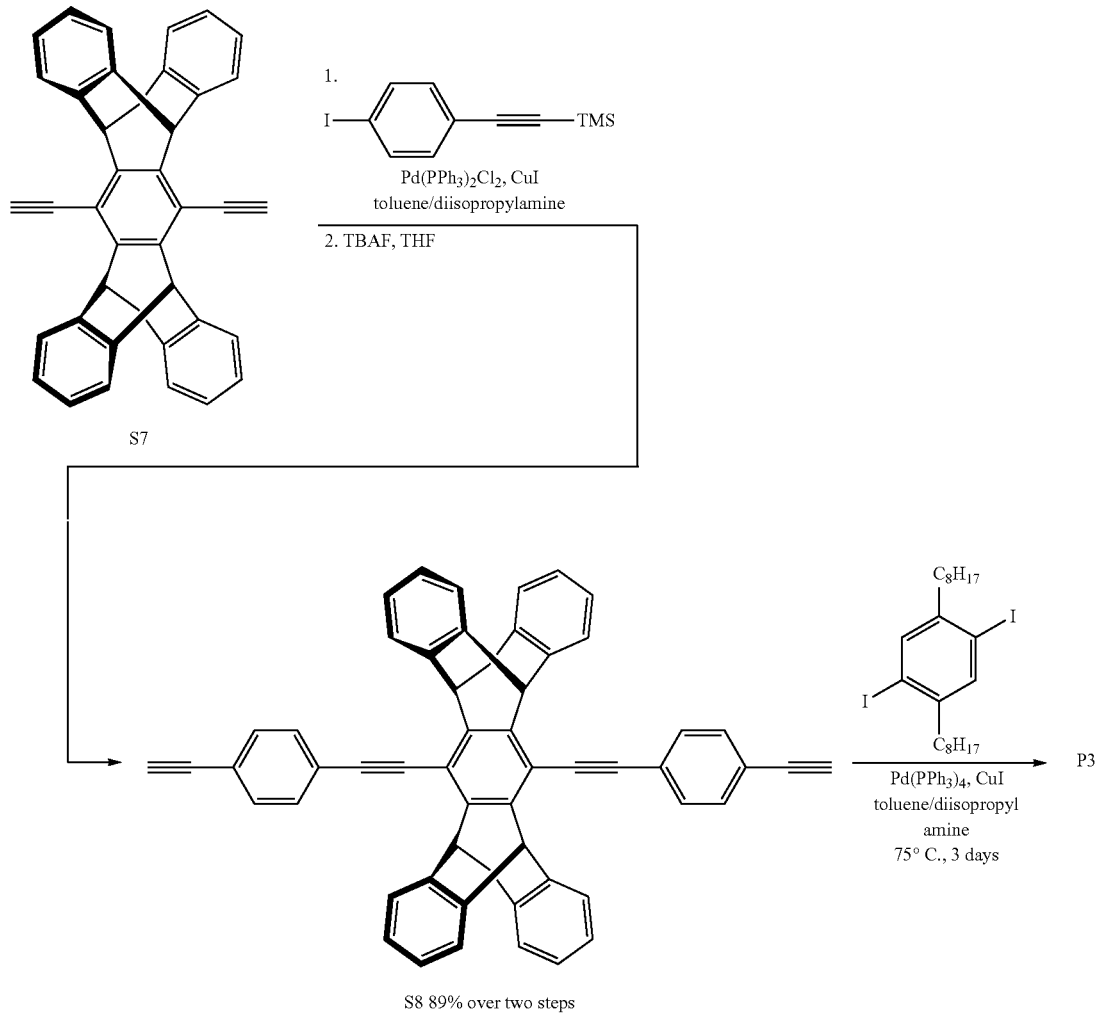

S8 89% over two steps

Monomer S8. Flame-dried 10 mL Schenk flask was charged with S7 (180 mg, 0.376 mmol), 4-iodophenylethynyl trimethylsilane (237 mg, 0.790 mmol), Pd(PPh$_3$)$_2$Cl$_2$ (13.2 mg, 0.019 mmol), and copper(I) iodide (7.2 mg, 0.038 mmol). The flask was evacuated and back-filled with argon three times. Toluene (2 mL) and diisopropyl amine (0.5 mL), degassed by freeze-pump-thaw, was added via syringe. The reaction mixture was stirred at 60° C. for 16 hours. The reaction mixture was then precipitated into methanol (50 mL). The solids were further cleaned by re-precipitation in methanol three times, followed by re-precipitation in acetone three times. The resulting off-white solids were suspended in 10 mL anhydrous tetrahydrofuran under argon. Tetrabutylammonium fluoride (1.0 M in tetrahydrofuran, 0.770 mL, 0.770 mmol) was added dropwise. The reaction mixture was stirred at room temperature for 15 minutes, and subsequently passed over a plug of silica gel, eluting with 50% dichloromethane in hexanes. The solvents were removed under reduced pressure, and the crude product was purified by column chromatography (silica gel, 30% dichloromethane in hexanes) to give S8 as an off-white powder (203 mg, 81% over two steps). M.p.>300° C. $^1$H NMR (300 MHz, CDCl$_3$): δ 3.27 (s, 2H), 5.86 (s, 4H), 6.96 (dd, J=5.1, 3.3 Hz, 8H), 7.38 (dd, J=5.1, 3.3 Hz, 8H), 7.65 (d, J=5.1 Hz, 4H), 7.75 (d, J=5.1 Hz, 4H).

P3. A flame-dried 100 mL Schlenk vessel with teflon screw-on cap under argon was charged with monomer S8 (69.92 mg, 0.103 mmol), 1,4-diiodo-2,5-dioctylbenzene (55.43 mg, 0.100 mmol), Pd(PPh$_3$)$_4$ (5.8 mg, 0.050 mmol), and CuI (1.3 mg, 0.070 mmol). In a glove box, toluene (16 mL), and diisopropyl amine (4 mL) were added. The Shlenk vessel was removed from the glove box and was stirred at 75° C. for 3 days. The reaction was then precipitated into 100 mL methanol. Yellow precipitates were collected via centrifugation, and the process was repeated three times with methanol, followed by three times with acetone to give P3 (66.7 mg, 68%) as bright yellow solids after drying under vacuum. Mn=73.7 kDa; PDI=10.5; DP=75 (THF-GPC). $^1$H NMR (500 MHz, THF-d$_8$): δ 7.92 (br, 4H), 7.78 (br, 4H), 7.52 (br, 2H), 7.41 (br, 8H), 6.95 (br, 8H), 6.00 (br, 4H), 1.30-1.60 (br, 24H), 1.44 (br, 4H), 0.98 (br, 10H).

Emulsion Synthesis

TABLE 1

Emulsion synthesis conditions and the resulting emulsion properties.

| [P1] in PFD (mg/ml) | Volume of PFD solution (mL) | Volume of 1X PBS buffer | Surfactnat | Surfactant Concentration | Emulsion size | Emulsion Z-potential |
|---|---|---|---|---|---|---|
| 2 | 0.01 | 5.0 mL | S1 | 0.01M | 245.8 ± 43.9 nm | −57 ± 13 mV |
| 2 | 0.01 | 5.0 mL | S1 | 0.02M | 242.1 ± 23.6 nm | −79 ± 11 mV |
| 2 | 0.01 | 5.0 mL | S2 | 0.0025M | 3~4 μm | −42 ± 6 mV |

S1: 2H,2H,3H,3H-perfluorononanoic acid,
S2: 8:2 monoPAPS.[7]

Figure 10:
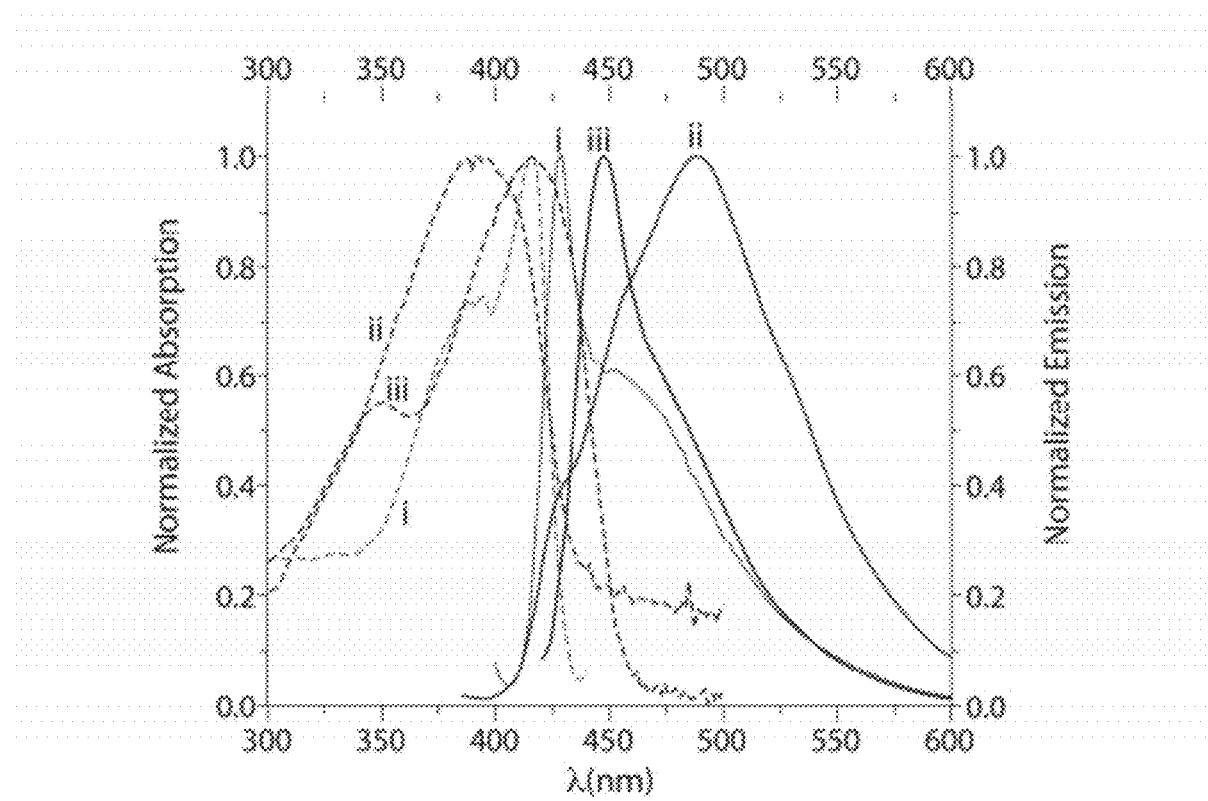
FIG. 10 shows the thin film absorption (dotted) and emission (solid) spectra of P1 (1), P2 (ii), and P3 (iii).
Figure 21:
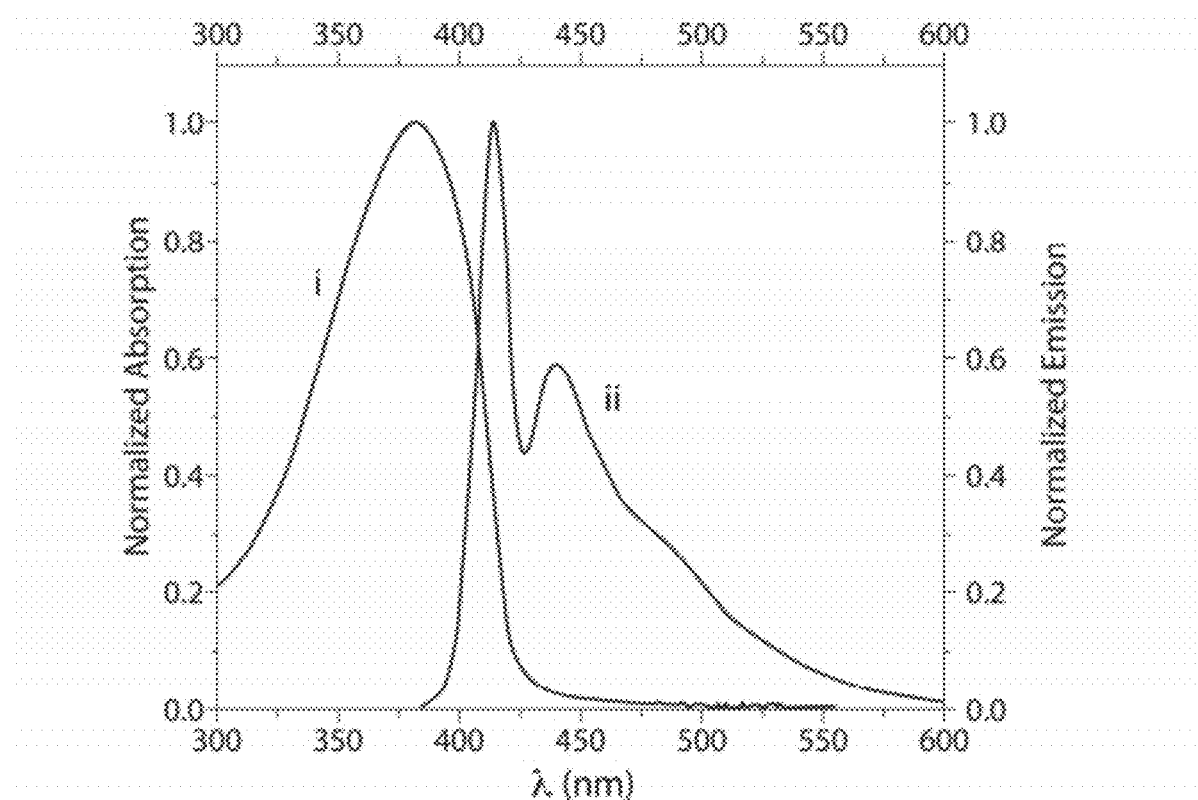
FIG. 21 shows the absorption (i) and emission (ii) spectra of P3 in toluene.

In a 50 mL round-bottom flask, surfactant (Table 1, columns 4 and 5) in 5.0 mL PBS buffer was heated to 75° C. while stirring. After complete dissolution of the surfactant, P1 (10 μL, 2 mg/ml in perfluorodecalin) was added. The flask was then removed from heat and was sonicated with a probe sonicator at 3 Watts (rms) for 5 minutes. The solution was subsequently allowed to cool to room temperature. Excess surfactant was removed via filtration. The size distribution and Z-potentials of the emulsions are shown in Table 1 (columns 6 and 7). FIG. 21 shows the absorption (i) and emission (ii) spectra of P3 in toluene. FIG. 10 shows the thin film absorption (dotted) and emission (solid) spectra of P1 (i), P2 (ii), and P3 (iii).

Example 3

This example describes prophetic and non-prophetic compositions, methods, and systems for the early detection, diagnosis, and/or treatment of cancers, including breast cancer.

Figure 12:
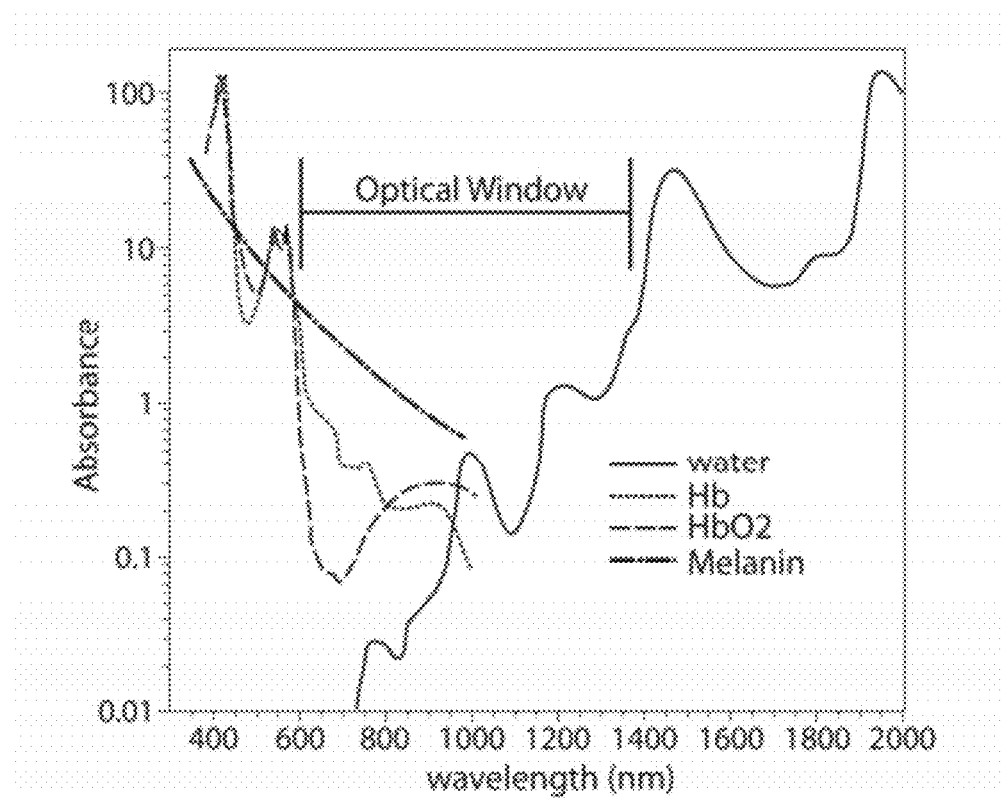
FIG. 12 shows relevant contributions to the absorption of electromagnetic radiation by human tissue.

The platform described in this example makes use of organic photonic materials and concepts to achieve highly selective and sensitive optical emissive responses at wavelengths between 650 and 900 nm where human blood and tissue have relative transparency. (FIG. 12) Long wavelength optical signals also benefit from the inverse fourth-power relationship between the wavelength and light scattering. This allows for the penetration of longer-wavelength light, which is generally necessary for in vivo imaging, through the living tissues. The platform described in this example also makes use of fluidized fluorous particles utilizing perfluorodecalin, which is a component of an FDA-approved artificial blood surrogate, Fluosol Fluorous soluble groups, which display strong phase separation from both aqueous and organic phases, can serve as robust anchors to keep the particles and assembled photonic elements, and ligands, intact. Fluorous chemistry can be used to create fluorous emissive polymers, far-red chromophores, targeting ligands, and transducing assemblies for localization at breast cancer cells. The fluidized fluorous particles have the advantage in that they have mechanical properties and physical sizes similar to blood cells and hence can naturally interact with cancerous tissues. In addition, the high oxygen solubility in perfluorodecalin has been shown to provide large enhancements in the efficacy of photodynamic therapy. As a result, integration of singlet oxygen sensitizers into this platform, along with two-photon excitation, can provide a route for treatment of cancer. An additional opportunity afforded by the described platform is the use of $^{19}F$ NMR signals originating from fluorinated groups localized to tumors in MRI imaging. As a result, the systems created may be used for multiplexed sensing and treatment of cancer.

The design of optical materials employ the optical window (FIG. 12) between 600 and 1200 nm to create systems capable of in vivo use to detect and treat cancer (e.g., breast cancer). In addition to the absorption effects, long wavelength optical processes have the advantage that the scattering from inhomogeneous structures is reduced or eliminated. Furthermore, at longer wavelengths, there is no or minimal autofluorescence from native biological species. Optical performance systems can be designed to create (1) a high-resolution system that allows for precise location of cancerous tissue and (2) a highly sensitive system capable of detecting early stage cancer. The optimization of these two criteria can be accomplished in a modular system such as the use of fluorous particles. (FIG. 13) In this embodiment, a perfluorodecalin (PFD) filled particle (e.g., 98) was stable with use of an anionic carboxylate (e.g., 104) or phosphate surfactant. Fluorous tagged ligands (e.g., 106) with hydrophilic head groups can be assembled on the particle surface to recognize cancer cells. The liquid nature of the cell allowed these ligands to be properly presented to receptors on cancer cells and assemble into groups for optimal multivalent binding. The interior of the particle contained PFD solvent and photonic elements, including semiconducting polymers for light harvesting (e.g., 100) and far-red dyes (e.g. 102) capable of being excited either by direct absorption of a photon or through energy transfer from the polymer. In some cases, the materials employed the absorption of light and the transfer of energy to minority low band gap groups in the polymer structure or other emissive dyes that are placed in a non-covalent assembly.

Fluorous soluble polymers and functional particles were prepared. (FIG. 14) These brightly emissive particles ($\Phi_F$=59 in PBS buffer) were stable for months and provided that the degree of charge in the surfactant coating was sufficiently high. As an initial step toward functionalizing these particles with ligands, the surface carboxylates were reacted with biotin-$(PEG)_3$-$NH_2$ groups and a coupling agent to produce amide linkages. These biotinylated fluorous particles were then subjected to Texas Red labeled streptavidin and confocal microscope imaging showed particle agglomeration from the polyvalency and a clear overlay of the emission of the polymer with that of the Texas Red dye. Control experiments wherein the surface of the particles was similarly functionalized with $CH_3$-$(PEG)_3$-$NH_2$ showed no agglomeration or coincidence of the streptavidin with the particles.

Figure 14:
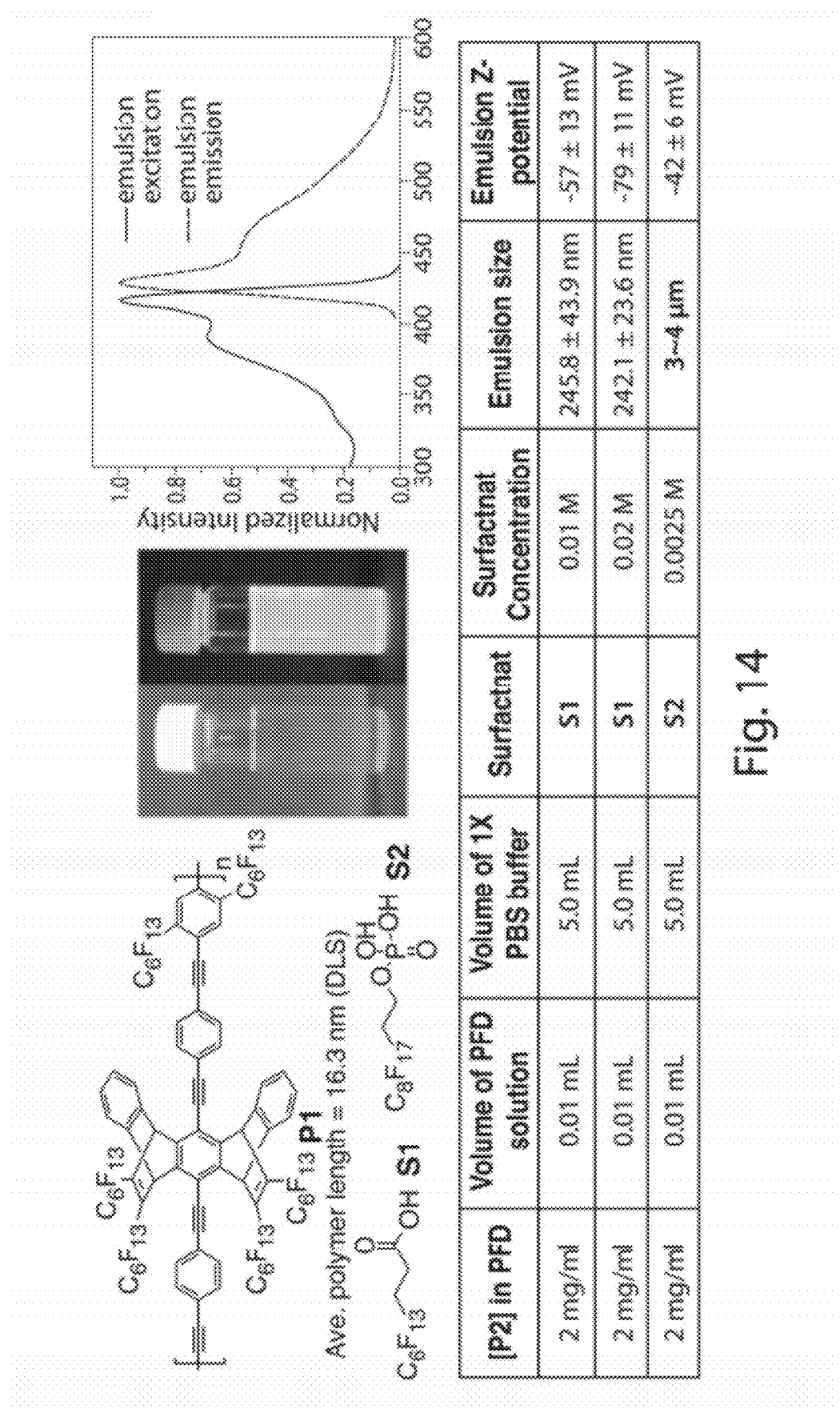
FIG. 14 shows the structure of P1, an emission/absorption spectra of P1, and a table of emulsions parameters and related data.

The emission particles shown in FIG. 14 have excellent behavior and confirm that stable particles containing semiconductive particles are highly stable and that fluorous tagged ligands on the particle surfaces can be used for biomolecular recognition. To excite these particles in the window for transmission in biological samples (FIG. 13), P1 can be excited using a two-photon method. As shown in FIG. 14, P1 is a fluorous conjugated polymer that has complete solvent orthogonality (fluorous soluble, organic insoluble). When P1 and PFD were dispersed with the surfactants (S1 and S2) in PBS buffer, emulsion particles were produced with bright emission as shown in the picture and spectrum in FIG. 14. The polymer provided a large absorption cross-section for two-photon absorption using methods similarly used to excite closely related non-fluorous materials. The extended conjugation of the polymer allowed for the excitations created by two-photon absorption to be transferred to lower bandgap dyes that luminesce at wavelengths greater than 600 nm for imaging. As shown in FIG. 15, these energy harvesting and transfer events result in enhancements in the far-red dyes relative to what may be achieved by direct excitation. As a result the photonic circuitry inside the fluorous particles can be used to effectively harvest light to give bright far-red emissions.

The data in FIG. 15 shows a 110-fold enhancement of the dye emission. This was accomplished with minimal overlap of the donor polymer's emission and the dye's absorption spectrum, which is generally assumed to be a requirement for efficient energy transfer in widely used fluorescence resonance energy transfer (FRET) schemes. After a number of systematic studies, it appeared that the energy transfer was accomplished through strong electronic (wavefunction) overlap between the polymer and the acceptor dye. This feature allows for the large shift to longer wavelengths. It should also be noted that only a small amount of dye (0.5 wt. %) was required to harvest more than half of the polymer's excitations.

Currently, breast cancer is largely identified via tissue biopsy combined with the identification of aberrant cell structures, while treatment is a combination of physical removal and toxicity targeted selectively at malignancies. Fluorous particles may be used for the in vivo detection of breast cancer at earlier stages and to also provide treatment. The fluorous soluble dyes and polymers may be synthesized as described herein. Additionally, the ligands and peptides may be associated with the surface of particles. Cancer recognition may be demonstrated with integrated particles and cancer cells.

The following sections describe (i) the synthesis of fluorous-soluble photonic materials, including two-photon absorbing emissive polymers capable of being excited by light >800 nm and far-red (near IR) dyes with high quantum yields and emissions between 650 and 800 nm; (ii) the synthesis of fluorous tagged ligands (e.g., folate and peptide) for targeting of cancer cells; (iii) the formation of integrated fluidized fluorous particles capable of being optically excited with light with wavelengths greater than 600 nm and the generation of far-red emissions from fluorous particles by two-photon excitation of a higher band-gap polymer and down conversion; and (iv) the binding of particles to cancer cells and analyze different perspective detection mechanisms involving direct imaging by binding of particles, as well as cancer cell-triggered changes in the fluorous particles.

Using techniques known to those of ordinary skill in the art, (e.g., depending upon the surfactant nature concentration), the size and concentration of the particles described above can be varied. The particles demonstrate high fluorescence quantum yields and exhibit selective binding to multivalent biological receptors when functionalized with a specific ligand. In addition, highly efficient fluorescence down conversion to far-red dyes, even with minimal spectral overlap as a result of overlap of the donor polymer's and acceptors dye's wavefunctions has been demonstrated. It should be understood that the polymer-dye combinations are not restricted by typical FRET design considerations. The ability to excite the class of target polymers by two-photon absorption was also demonstrated. The results in hand form a solid foundation for the design of new high performance systems for the detection and treatment of breast cancer. The following sections will detail additional materials that need to be produced in order to create improved particles and specific methods that will provide for high fidelity responses of these systems.

Figure 16:
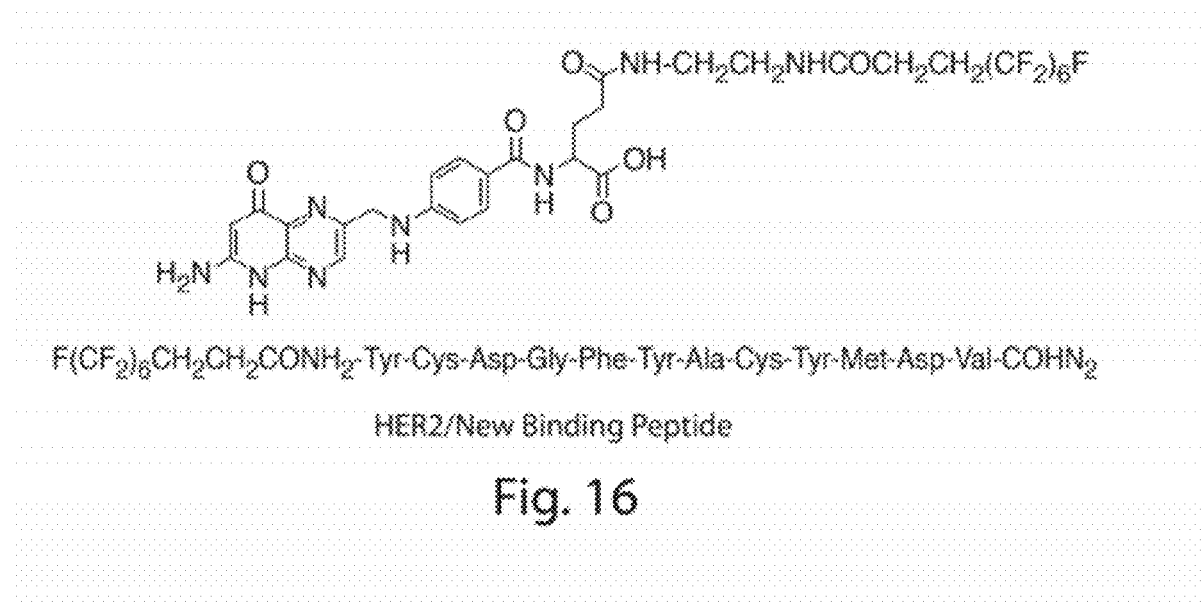
FIG. 16 shows a fluorous tagged folate and HER2/Neu binding peptide.

Targeting Ligands:

Similar to what was demonstrated with biotin and streptavidin described previously, fluorous-tagged ligands may be assembled on the surface of the fluorous emission particles. The fluid nature of the particles produced by the presence of PFD may allow for the ligands to be dynamically distributed on the surface of the particles and adopt optimal spatial distributions for interaction with cells. Cancer markers in serum for the early detection of most cancers are not readily available. Nanotechnology approaches to the treatment and detection of cancer include targeting ligands designed to bind directly to carcinomas. For example, fluorous tagged folate and HER2/Neu binding peptide (FIG. 16) may be produced using standard amide coupling procedures between the ligands and S1 (FIG. 14), and integrated into the emulsion particles. The modularity of the fluorous emulsion particle platform can readily allows for the introduction of other ligand systems, and hence the number of targeting ligands can be readily expanded.

Two Photon Absorbing Materials:

Molecular systems having the largest two-photon absorption cross-sections exhibit symmetric structures with units having lower electronic affinities (electron donors, D) and those having higher electronic affinities (electron acceptors, A), linked by conjugated pi-systems. Chromophoric systems having D-A-D are well suited to produce materials with high two-photon absorption cross-sections. Fluorous soluble analogs of known two-photon absorbing dyes may be produced. For example, a fluorous analog of a well known D-A-D distyrylbenzene (FIG. 18) may be produced. The —$CH_2CH_2OCH_2CH_2$-spacer between the amine and the perfluorooctyl group helps minimize the inductive effects of the perfluorooctyl moiety on the donor nitrogens to maintain the high two-photon absorption cross-section. Based upon the properties of the non-fluorinated analogs this dye may fluoresce at around 600 nm, and hence be on the edge of the transparency window given in FIG. 12. Far-red emitting small molecule two-photon absorbing dyes based on squaraine structures as shown in FIG. 15, are also known and hence fluorous analogs (FIG. 17) may be produced for direct two-photon excitation and as energy acceptors.

As described previously, an advantage of polymer-based two-photon absorption is the fact that the harvested energy can undergo facile migration along the polymer backbone to an emissive dye. As a result, collection of light by a conjugated polymer and subsequent down conversion to a minority far-red dye has the prospects of producing a stronger two-photon response. Polymers with D-A structures (FIG. 19) are suitable candidates as strong two photon absorbers and have appropriate D-A-D triads. The strongly electron withdrawing nature of perfluoroalkyl groups make them natural candidates for integration into acceptor groups. The acceptor monomers shown in FIG. 19 should be accessible through condensation reactions between the phenyl- and thiophene-diamines and fluorous carbonyl compounds. These acceptor monomers make use of intermediates previously developed by in similar syntheses of non-fluorous analogs As discussed before, the perfluoroalkyl groups may be isolated from the donor units to avoid inductive effects that limit the electron donation and hence the two-photon absorption efficiency.

Figure 20:
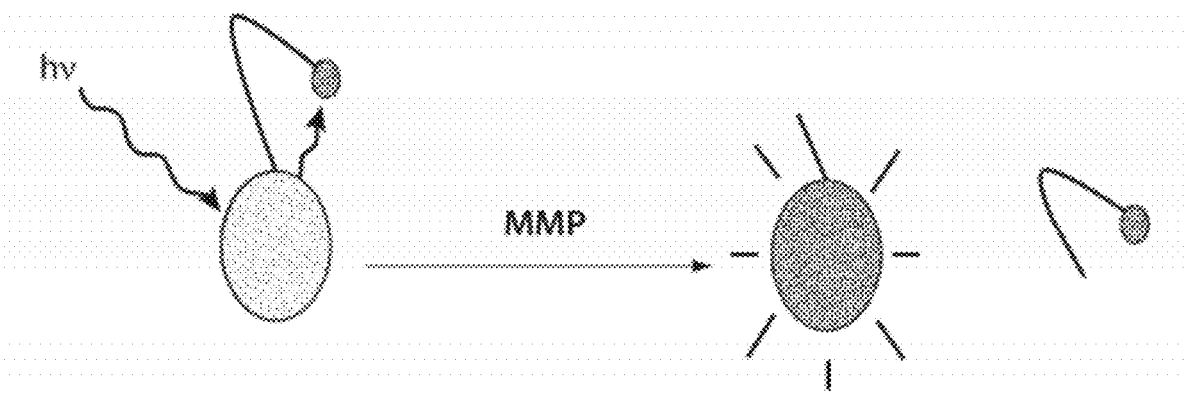
FIG. 20 shows a schematic illustrating the turn-on of a fluorous particle's fluorescence by cleavage of a quencher from the particle.

Spectroscopic Studies and Cancer Detection:

One- and two-photon photophysical studies may be performed on assembled fluorous emulsion particles and absorption cross-sections and emissive quantum yields can be determined. The energy transfer between the polymers in FIG. 19 as well as P1 and far-red squaraine dyes can be investigated. The high efficiency of this energy transfer may be a result of a tight complex between the donor polymers and the acceptor dyes. The fluorous effect may promote such types of interactions. Specifically, the long perfluoroalkanes on the dyes and the polymers may favor interactions with the PFD solvent. The aromatic faces of the chromophores, however, may or may not have specific interactions with the fluorous phase. As a result, the aromatic faces of the molecules may be driven together, similar to a hydrophobic effect in water. Energy transfer through the polymer network inside of the fluorous emulsion particles can also be probed by fluorescence depolarization measurements. FIG. 20 shows a schematic illustrating the turn-on of a fluorous particle's fluorescence by cleavage of a quencher from the particle.

Cell lines, including the human breast cancer cell line MCF-7 and the mouse (breast cancer) line TD, can be used in connection with the methods and compositions described herein. For example, studies with cells can use of a confocal microscopy and the binding of the compositions to cells can be analyzed and the specificity of these systems to cancer cells can be determined. Parameters which may be determined may be the charge on the particles (zeta potential, in FIG. 14), the concentration of the ligand(s), and the size of the particle.

Additional transduction mechanisms may be investigated to give greater fidelity in the detection of breast cancer cells by the fluorous emulsion particles. In some embodiments, two different particles may be prepared with the S1 surfactant. When the charge is lower (fewer ionic surfactants) the particles may condense and change shape with agitation. For lower-charged particles, reduced pH, along with agglomeration at the surface of cancer cells may give rise to particle equilibration (fusion and/or fission). This feature again reflects the dynamic nature of the fluorous particles. If two types of particles with different chromophoric cargos were presented to cancer cells, it may be determine if the reduced pH around cancer cells and agglomeration of the fluorous particles can cause a scrambling of the materials contents. This can potentially be used to create a large response. To understand this effect, consider the data in FIG. 15. Energy transfer from the polymer to the squaraine results in a large (110×) enhancement in the sqauraine's fluorescence. This effect may be even greater if the comparison were not to the direct excitation of the squaraine at its absorption maxima. Additionally, using two photon absorptions tuned to the polymers may also increase the contrast. A large turn-on signal and the high spatial resolution provided by two-photon excitation have excellent prospects for the detection smaller amounts of cancer cells for eventual in vivo detection.

A particularly insidious aspect of cancer is the ability of tumors to metastasize. A cadre of secreted proteins designed to decompose connective tissue facilitates the movement of malignant cells within an organism and makes metastasis possible. Matrix metalloproteases (MMPs) form an important part of this set of proteins, and act by degrading collagen in basement membranes, allowing cancerous cells to invade other tissues. The fluorous emulsion particle platform, can be readily functionalized with oligopeptides known to be degraded specifically by MMPs associated with certain cancer types. These oligopeptides can serve to tether a fluorescence quencher (nitroaromatic or strongly absorbing azo-dye) to the particle. As shown in FIG. 20, the particle may not initially fluoresce as strongly due to presence of tethered quenchers. Assuming that the peptide sequence is sufficiently specific, a MMP present in vivo may cleave the quenching agent from the particle resulting in the strong fluorescence from the particle. This method has previously employed with semiconductor polymers in solution to create amplified responses. Fluorous particles generating high degrees of quenching can be employed. For example, the polymer to be quenched can be localized at the surface of the particle. Analog of P2 shown in FIG. 5, which is not fluorous soluble, can serve this role. The geometry of the rigid polycyclic scaffold may be such that all of the four fluoroalkyl groups are oriented in the same direction. Hence P2 can behave as a fluorous surfactant and analogs with hydrophilic sidechains rather than the $C_{14}$ groups can stabilize aqueous fluorous emulsions. Thus, the particle's fluorescence may be localized in areas of high matrix metalloprotease activity. The peptides may also serve as an element stabilizing a specific particle size, the action of the MMP may serve to cause particle equilibration and, as discussed before, the fusion of particles having polymer donors with dye acceptors can provide a large signal gain in the far-red region. To evaluate these strategies, peptide-modified fluorous particles can be used to assay a variety of matrix metalloproteases (available commercially from Calbiochem, La Jolla, Calif.).

Example 4

The following example describes the synthesis of 2,3-Bis(perfluorohexyl)thieno-[3,4-b]pyrazine (2) according to the reported procedure by Uno, H. et al., Synlett 1993, 91. To a three-necked round-bottomed flask (500 mL) equipped with a magnet stirring bar were added thieno[3,4-b]pyrazine (1.05 g, 7.7 mmol), perfluorohexyl iodide (8.25 g, 18.5 mmol), and $Et_2O$ (77 mL) under an argon atmosphere. The solution was cooled at −78° C. before addition of $BF_3.OEt_2$ (2.28 mL, 18.5 mmol). To the resulting suspension was added an MeLi—LiBr (1.5 M ether solution, 12.3 mL, 18.5 mL) at −78° C. over a period of 15 min. The mixture was stirred at −78° C. for 1 h before quenching with saturated aqueous $NH_4Cl$ (30 mL). The organic layer was separated and aqueous layer was extracted with ether (100 mL×2 times). The combined organic layer was washed with saturated aqueous NaCl (100 mL), dried over $Na_2SO_4$, and evaporated under reduced pressure to give black solid. The residue was dissolved in $CH_2Cl_2$ (10 mL), absorbed with silica gel (10 g), and evaporated. The residue was purified by column chromatography on silica gel (hexane/AcOEt 95/5) to give the title compound as gray solid (3.57 g, 60%). Mp: 122-123° C. $R_f$ 0.60 (hexane/AcOEt 8:1). $^1$H NMR (300 MHz, $CDCl_3$): δ 4.23-4.25 (m, 2H), 4.32-4.42 (m, 2H), 6.13 (s, 2H); $^{19}$F NMR (282 MHz, $CDCl_3$): δ −81.2 (m, 6F), −116.5 (m, 1F), −117.5 (m, 1F), −121.6 (m, 6F), −122.4 (m, 4F), −123.2 (m, 4F), −126.5 (m, 4F). IR (KBr): ν 3438, 3095, 1604, 1520, 1239, 1203, 1142, 1121, 1070, 746, 647 cm$^{-1}$. HR-MS (EI): calcd for $C_{18}H_6F_{26}N_2S$ 776.9909 $[M+H]^+$. found 776.9901. Anal. Calcd for $C_{18}H_6F_{26}N_2S$: C, 27.85; H, 0.78; N, 3.61; S, 4.13. Found: C, 27.78; H, 0.73; N, 3.45; S, 4.21.

Example 5

The following example describes the synthesis of 5,7-Dibromo-2,3-bis(perfluorohexyl)thieno[3,4-b]pyrazine (3). To a two-necked round-bottomed flask (100 mL) equipped with a magnet stirring bar were added 2,3-bis(perfluorohexyl)tetrahydro-thieno[3,4-b]pyrazine (776.3 mg, 1.0 mmol) and THF (10 mL) under an argon atmosphere. To the solution was added N-bromosuccinimide (1.07 g, 6.0 mmol) portionwise over a period of 5 min, and the resulting mixture was stirred at room temperature for 1.5 h. After addition of silica gel (5 g) into the reaction mixture, evaporation of the resulting suspension under reduced pressure gave an orange residue, which was purified by column chromatography on neutral alumina (activated level 1, hexane) to give 5,7-dibromo-2,3-bis(perfluorohexyl)thieno[3,4-b]pyrazine (850.9 mg, 91%) as a light brown solid. Mp: 46-47° C. $R_f$ 0.57 (hexane/AcOEt 8:1. $^{19}$F NMR (282 MHz, CDCl$_3$): δ −81.2 (m, 6F), −106.4 (m, 4F), −118.2 (m, 4F), −120.3 (m, 4F), −123.1 (m, 4F), −126.4 (m, 4F). IR (KBr): ν 1509, 1366, 1318, 1239, 1200, 1143, 1085, 1012, 988, 721, 679 cm$^{-1}$. HR-MS (EI): calcd for $C_{18}Br_2F_{26}N_2S$ 930.7793 [M+H]$^+$. found 930.7793. Anal. Calcd for $C_{18}Br_2F_{26}N_2S$: C, 23.25; N, 3.01; S, 3.45. Found: C, 23.44; N, 2.92; S, 3.49.

Thienopyrazine 3 is highly soluble in common solvents, and was readily purified by column chromatography on neutral almumina with hexane as an eluent. Notably, thienopyrazine 3 was found to emit orange fluorescence both in solution and in the solid state. Without wishing to be bound by theory, this behavior may be attributed to the presence of rigid and bulky perfluoroalkyl side chains, which may reduce or suppress intermolecular pi-pi stacking between adjacent thienopyrazine rings.

Example 6

The following example describes the synthesis of poly(2,3-perfluorohexyl(thieno-[3,4-b]pyrazine) (P4). As described herein, fluorous biphase solvent systems can be effective in the synthesis of highly fluorinated conjugated polymers. Therefore, a polycondensation reaction using hexamethylditin, employing fluorous three-cosolvents system (i.e. THF/NMP/perfluoro-(methylcyclohexane) 2:1:2 v/v), was employed.

A Schlenk tube (50 mL) equipped with a magnetic stirring bar was charged with thienopyrazine 3 (465.0 mg, 0.50 mmol) and copper iodide (3.5 mg, 50 µmol). The tube was then capped with a rubber septum, evacuated for 5 min and purged with argon. The evacuation-purge operation was repeated twice. Hexamethylditin (177.5 mg, 0.525 mmol), Pd(PPh$_3$)$_4$ (28 mg, 25 µmol), THF (5 mL), NMP (2.5 mL), and perfluoro(methyl-cyclohexane) (5 mL) were added to the mixture at room temperature in a glove box. The resulting mixture was heated at 80° C. for 48 h. The reaction mixture was poured into aq. KF (5 wt %, 20 mL) after the mixture was allowed to cool to room temperature, and then the resulting mixture was stirred for 1 h. The fluorous layer was washed with MeOH (20 mL) and water (20 mL), dried over anhydrous Na$_2$SO$_4$, and then concentrated in vacuo to give a dark-blue film. The film was detached by sonication in EtOH (20 mL). Removal of EtOH in reduced pressure gave P4 (380.2 mg, 95%) as a dark-blue solid. Further purification was carried out by Soxhlet extraction with acetone, hexane, and CHCl$_3$ for 12 h each solvent. IR (KBr): ν 1517, 1422, 1361, 1237, 1195, 1137, 1081, 849, 793, 667 cm$^{-1}$. HR-MS (DART): calcd for $C_{18}Br_2F_{26}N_2S$ 930.7793 [M+H]$^+$. found 930.7793. Anal. Calcd for $(C_{18}Br_2F_{26}N_2S)_n$: C, 28.07; F, 64.13; N, 3.64; S, 4.16. Found: C, 28.46; F, 65.50; N, 3.67; S, 4.31.

Example 7

Figure 23:
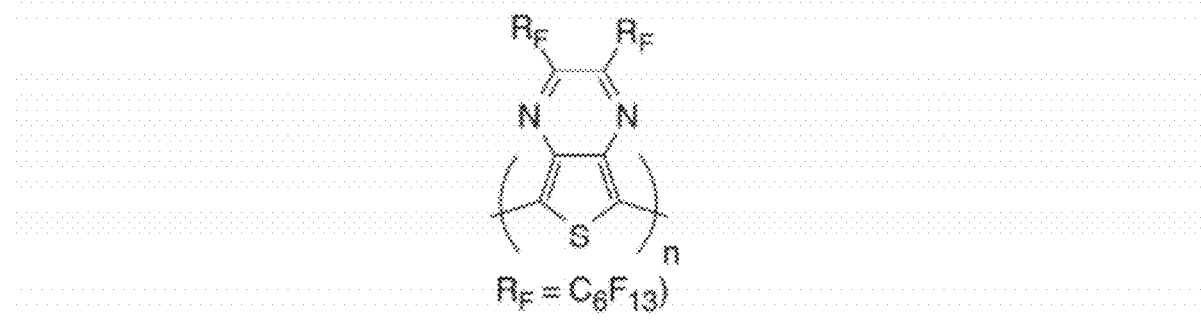
FIG. 23 shows an n-channel polymer semiconductor, poly (2,3-bis(perfluorohexyl)-thieno[3,4-b]pyrazine) ("P4"), according to one embodiment.
Figure 24:
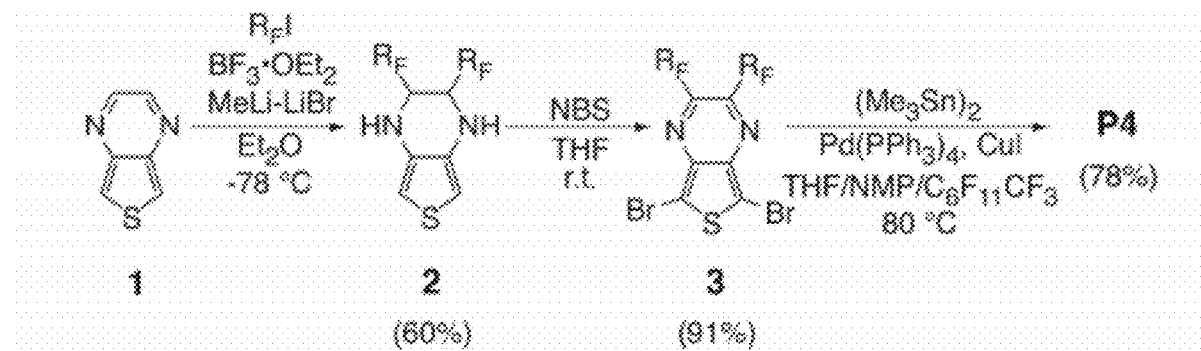
FIG. 24 shows the synthesis of polymer P4.

The following example describes the characterization and study of an n-channel polymer semiconductor, poly(2,3-bis(perfluorohexyl)thieno[3,4-b]pyrazine) ("P4"). (FIG. 23) The synthesis of P4 is shown in FIG. 24 and described in Examples 4-6.

Figure 29:
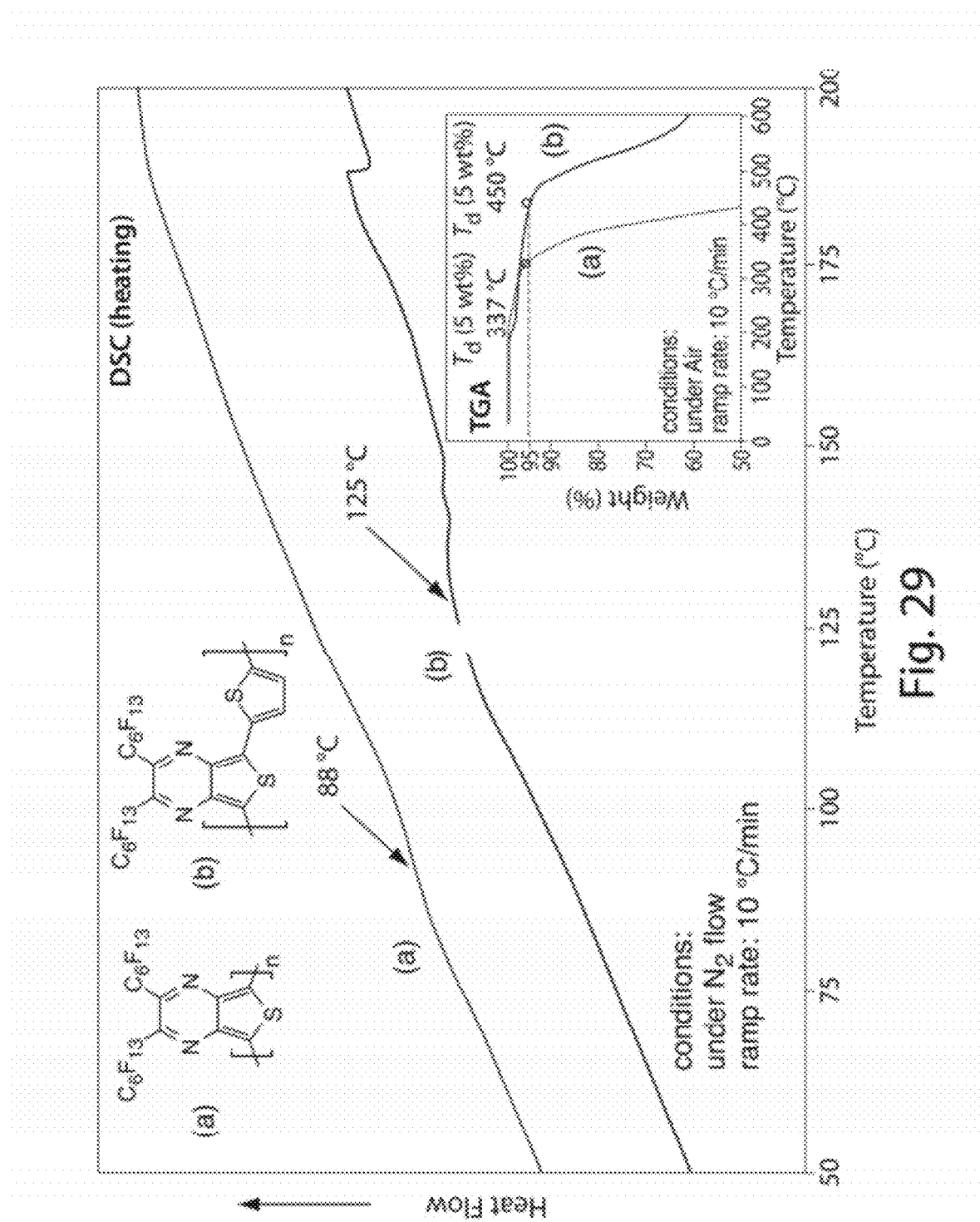
FIG. 29 shows differential scanning calorimetry (DSC) and thermogravimetric analysis (TGA) data for (a) P4 and (b) P5.

P4 was shown to be soluble in fluorous solvents such as perfluorooctane (FC-77), perfluoro(methylcyclohexane) (PFMC), and perfluorodecalin, but insoluble in common organic solvents like acetone, hexane, dichloromethane, and toluene. The orthogonal solubility of P4 allowed for facile purification. For example, crude P4 product was easily purified by extraction with FC-77 followed by Soxhlet extraction with hexane, acetone, and chloroform for 12 h, respectively, to give pure P4 in 78% yield. Thermogravimetric analysis (TGA) under the air showed high $T_d$ (5 wt %) of 337° C. while differential scanning calorimetry (DSC) analysis showed no drastic thermal transitions. (FIG. 29)

Figure 25A:
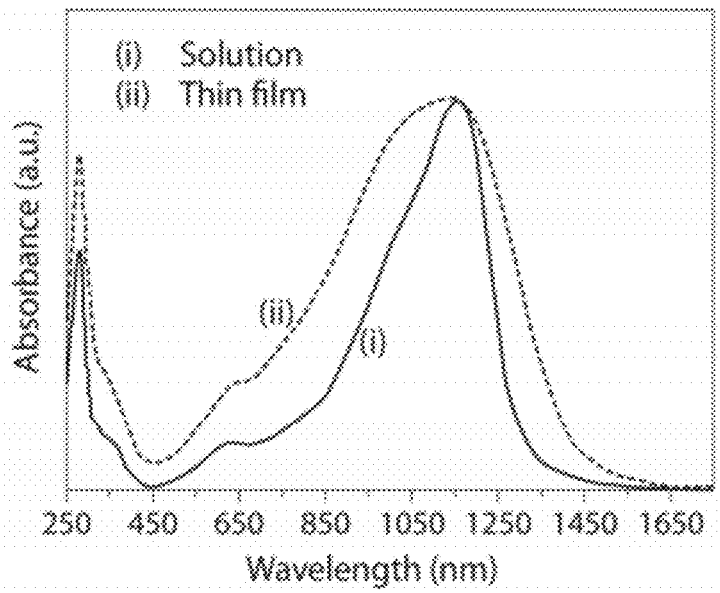
FIG. 25 shows (a) UV-vis-NIR absorption spectra of P4 in dilute perfluorooctane solution and a thin film deposited on a glass substrate; and (b) a cyclic voltammogram of a thin film of P4 deposited on an ITO electrode in an $CH_3CN$ solution of $Bu_4NPF_6$ (0.1 M) measured at the scanning rate of 10 mV/s.

FIG. 25A shows UV-vis-NIR absorption spectra of P4 as (i) a dilute FC-77 solution and (ii) a thin film deposited on a glass substrate. Both samples shows $\lambda_{max}$ at around 1100 nm, while the thin film shows a broad and relatively structureless peak compared to solution sample. Optical band gap $E_g$ estimated from the absorption edge $\lambda_{onset}$ of thin film was found to be as low as 0.75 eV, as shown in Table 2), which is lower that (0.93 eV) of chemically synthesized poly(2,3-dihexylthieno[3,4-b]pyrazine) (pC$_6$TP), the corresponding nonfluorinated counterpart of P4. The relatively lower band gap of P4 may be attributed to the more planar conformation of P4 than that of pC$_6$TP, which, without wishing to be bound by theory, may be induced by the presence of the rigid perfluoroalkyl side chains in P4.

Figure 25B:
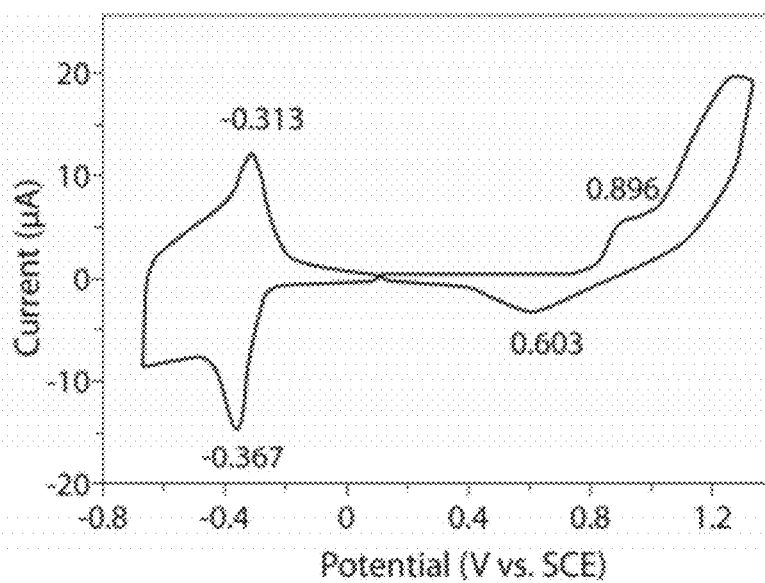

The electrochemical behavior of P4 was also investigated. FIG. 25B shows the cyclic voltammogram of a thin-film of P4 cast on an ITO electrode in acetonitrile. Electron affinity (EA) estimated from the reduction onset potential was found to be as high as 4.12 eV (Table 2), which is comparable to those of well-known electron transporting compounds, PCBM (4.2 eV) and BBL (4.0 eV). Ionization potential (IP) was calculated as 5.20 eV. Reversible color change of the film turning deep-purple from deep-blue during n-doping was observed. Without wishing to be bound by theory, these results suggest that the strong electron-withdrawing effect of perfluoroalkyl side chains may stabilize the electron-injected state of P4.

The conductivity (σ) of a thin film of P4 doped with THF solution of sodium naphthalide was measured using a four-point-probe method to be 17.9 S/cm. This value is significantly higher than that obtained with a thin film of poly(2,3-dihexylthieno[3,4-b]pyrazine), a non-fluorinated analogue of P4, when doped with NOBF$_4$ (see Pomerantz, M. et al. J. Chem. Soc., Chem. Commun. 1992, 1672).

In summary, P4 was shown to exhibit selective solubility to fluorous solvents, high electron affinity, electrochemical n-doping behavior, and a low band gap. Furthermore, OFET properties such as n-channel semiconductor properties are exhibited by P4.

TABLE 2

Summary of Optical and Electrochemical Properties of P4.

| $\lambda_{max}{}^a$ (nm) | $\lambda_{onset}{}^b$ (nm) | $E_g{}^{optc}$ (eV) | $E_{onset}{}^{redd}$ (V) | $E_{onset}{}^{oxe}$ (V) | EA$^f$ (eV) | IP$^g$ (eV) | $E_g{}^{ech}$ (V) |
|---|---|---|---|---|---|---|---|
| 1130 | 1644 | 0.75 | −0.284 | 0.795 | 4.12 | 5.20 | 1.08 |

$^a$Absorption maximum of a thin film.
$^b$Absorption edge of a thin film.
$^c$Optical band gap estimated from $\lambda_{onset}$.
$^d$Onset reduction potential (vs SCE).
$^e$Onset oxidation potential (vs SCE).
$^f$Electron affinity estimated from the following equation: EA = $E_{onset}{}^{red}$ + 4.4 (eV).
$^g$Ionization potential estimated from the following equation: $E_{onset}{}^{ox}$ + 4.4 (eV).
$^h$Electrochemical band gap calculated from the following equation: $E_g{}^{ec} = E_{onset}{}^{ox} − E_{onset}{}^{red}$.

Example 8

Figure 26:
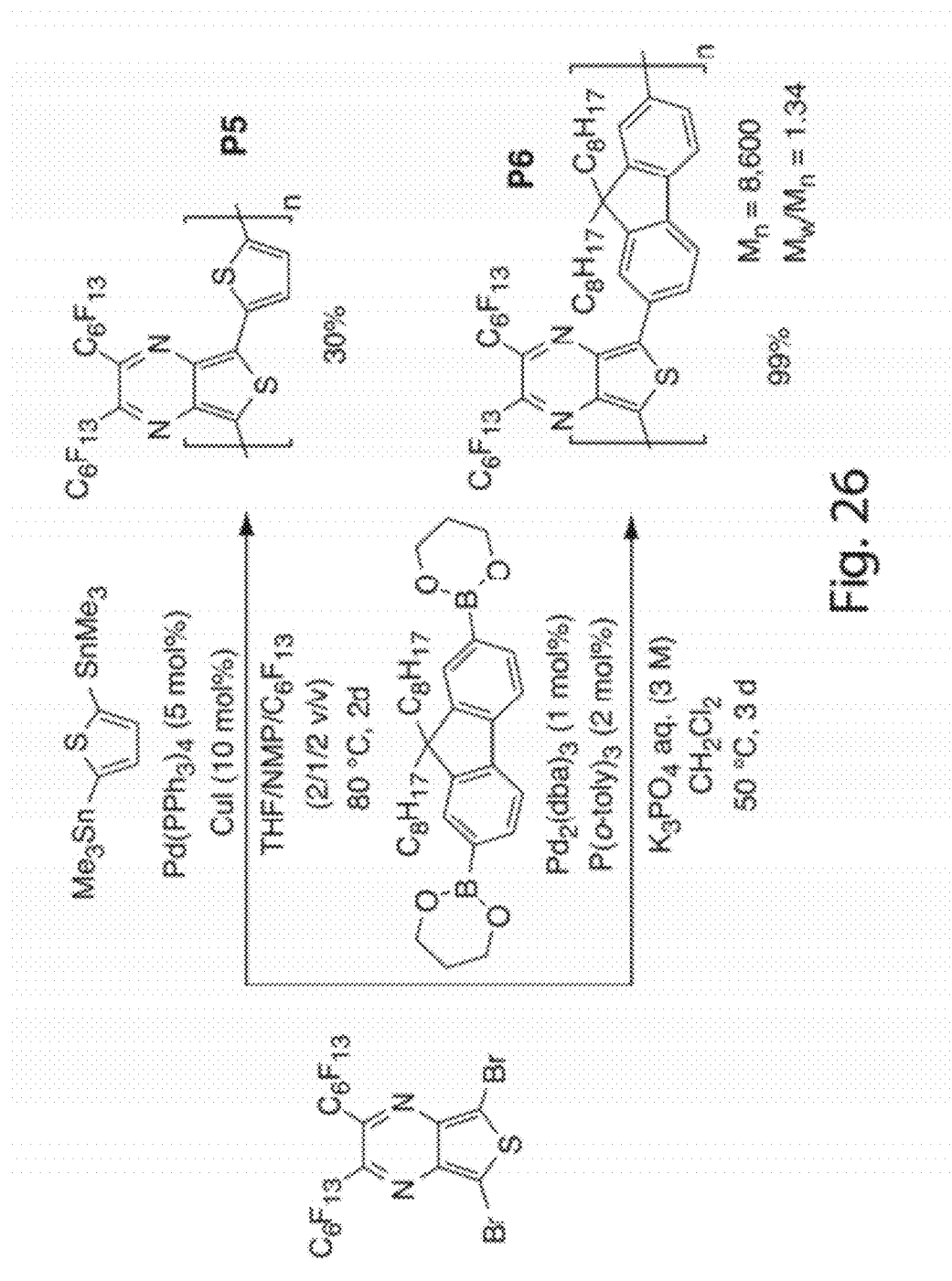
FIG. 26 shows the synthesis of thienopyrazine copolymers P5 and P6.
Figure 27A:
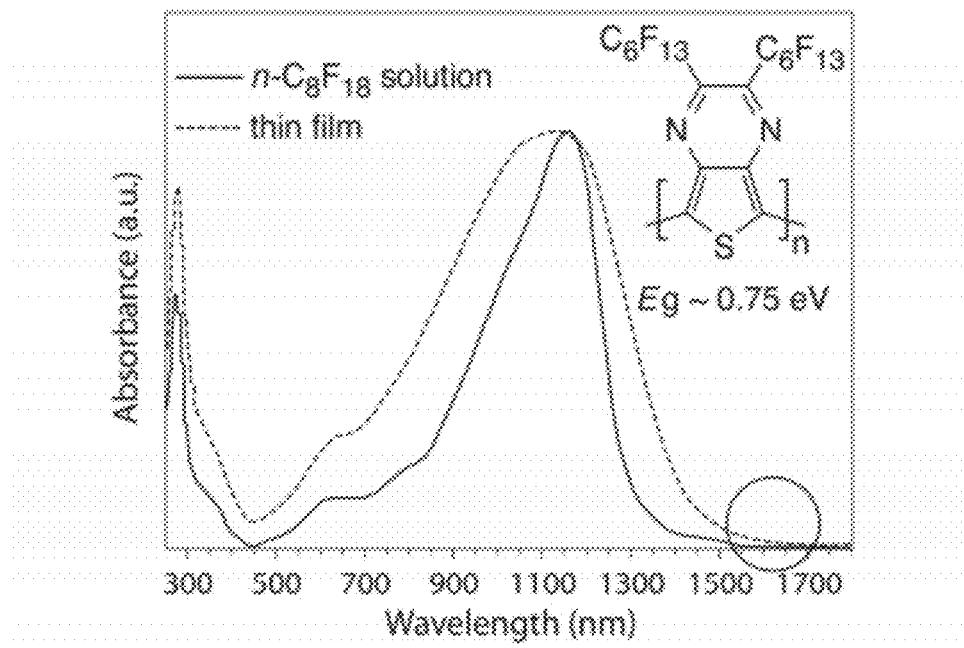
FIG. 27 shows the UV-vis-NIR absorption spectra for (a) P4, (b) P5, and (c) P6, as well as (d) an analogous, non-fluorinated thienopyrazine homopolymer.
Figure 27B:
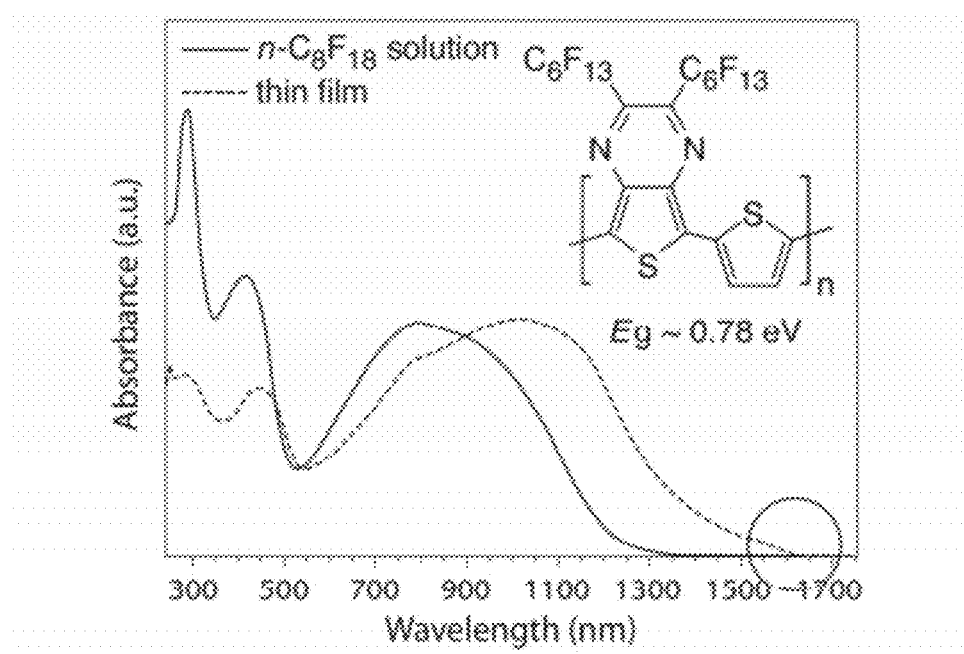
Figure 27C:
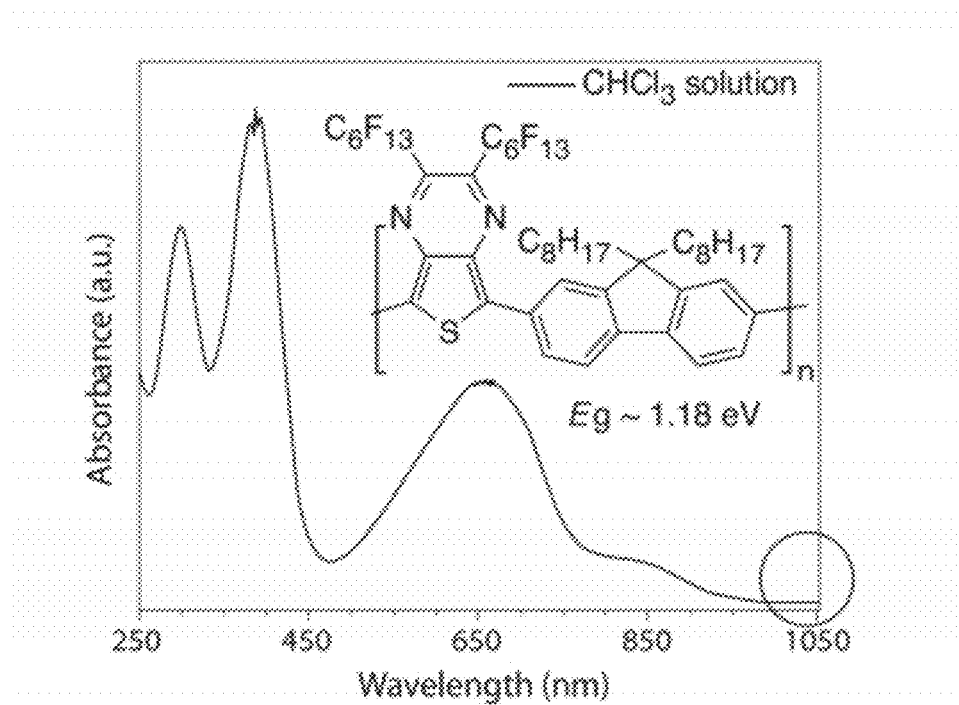
Figure 27D:
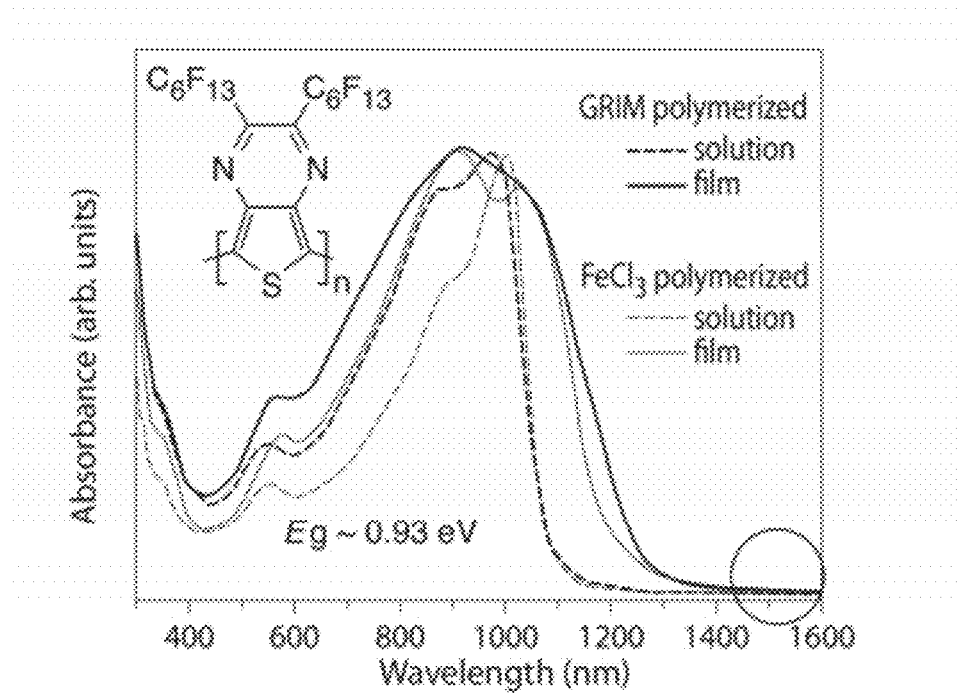

The following example describes the synthesis and study of various copolymers containing a fluorinated thienopyrazine unit. FIG. 26 shows the synthesis of polymers P5 and P6 using a procedure similar to that described in Example 6. P5 and P6 were shown to be soluble in both fluorous solvents, such as $C_6F_{11}CF_3$, $C_8H_{18}$, and common organic solvents, such as hexane, ether, toluene, and chloroform.

FIG. 27 shows the UV-vis-NIR absorption spectra for (a) P4, (b) P5, and (c) P6, as well as (d) an analogous, non-fluorinated thienopyrazine homopolymer. The changes in absorption and emission in the thin films suggest increased planarization and interchain interactions, which enhance electrical properties. For example, a film of fluorinated homopolymer P4 was found to have a bandgap of about 0.75 eV, lower than that of the corresponding non-fluorinated homopolymer analogue shown in FIG. 27D (e.g., 0.93 eV). Without wishing to be bound by theory, this may be ascribed to the increased planarity of P4. Copolymers P5 and P6 also exhibited lower bandgaps than that of the corresponding non-fluorinated copolymers.

Figure 28:
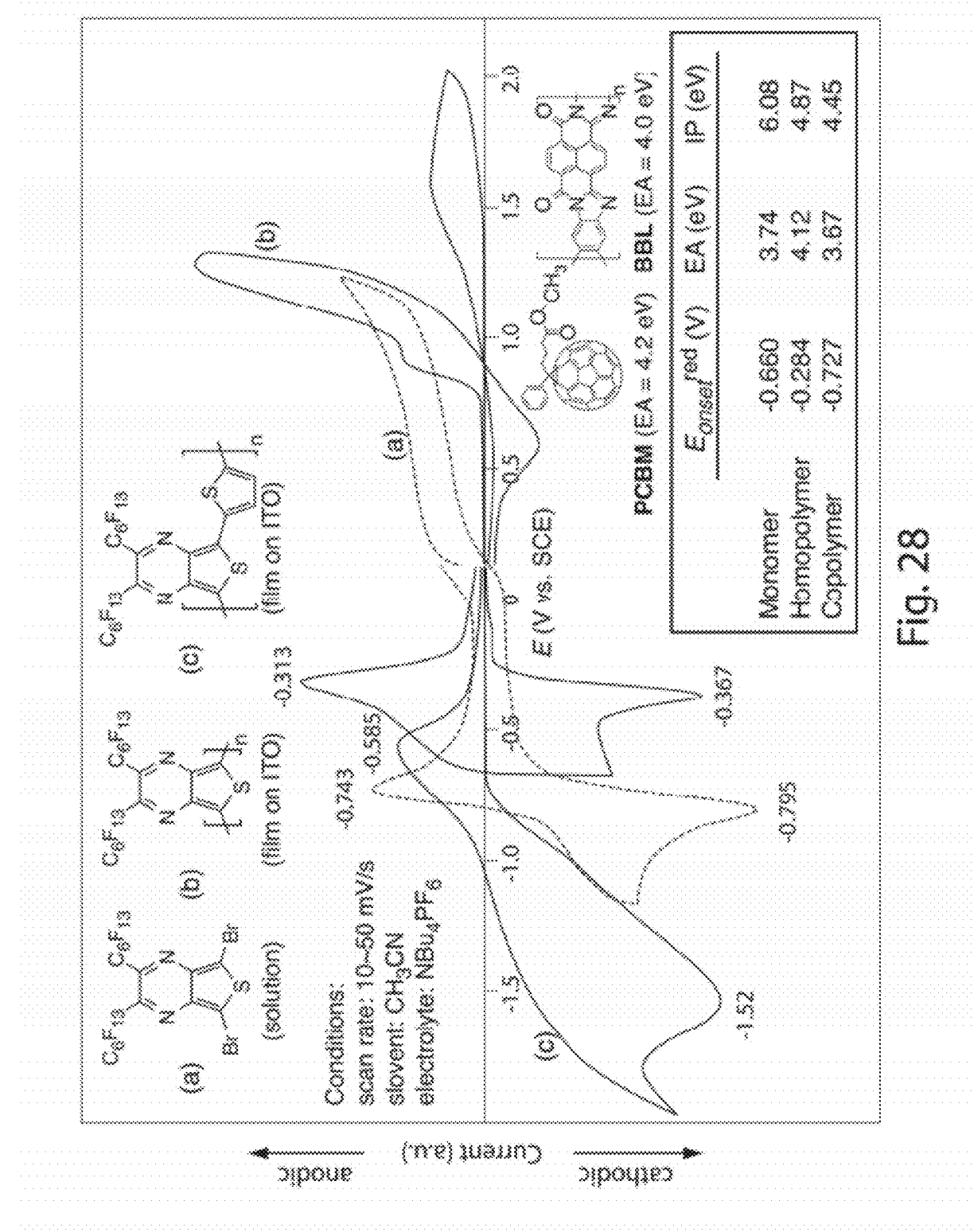
FIG. 28 shows cyclic voltammograms for (a) thienopyrazine 3 in solution, (b) a film of P4 on ITO, and (c) a film of P5 on ITO.

FIG. 28 shows cyclic voltammograms for (a) thienopyrazine 3 in solution, (b) a film of P4 on ITO, and (c) a film of P5 on ITO. The large difference between the thienopyrazine monomer 3 and the homopolymer P4 demonstrates the reversibility and enhanced electroactivity achieved in the polymer structure. The large electrochemical hysteresis of the copolymer P5 may be the result of slow ion diffusion and solid state reorganization with oxidation and reduction.

FIG. 29 shows DSC and TGA data for (a) P4 and (b) P5, illustrating the relative thermal transitions and the high temperature stability of these materials. The relatively high degradation temperatures ($T_d$) of 337° C. for P4 and 450° C. for P5 may be due to the presence of plural strong carbon-fluorine bonds.

Example 9

In the following example, fluorine-containing polymers were incorporated into organic devices, such as a an organic field effect transistor (OFET).

Figure 30A:
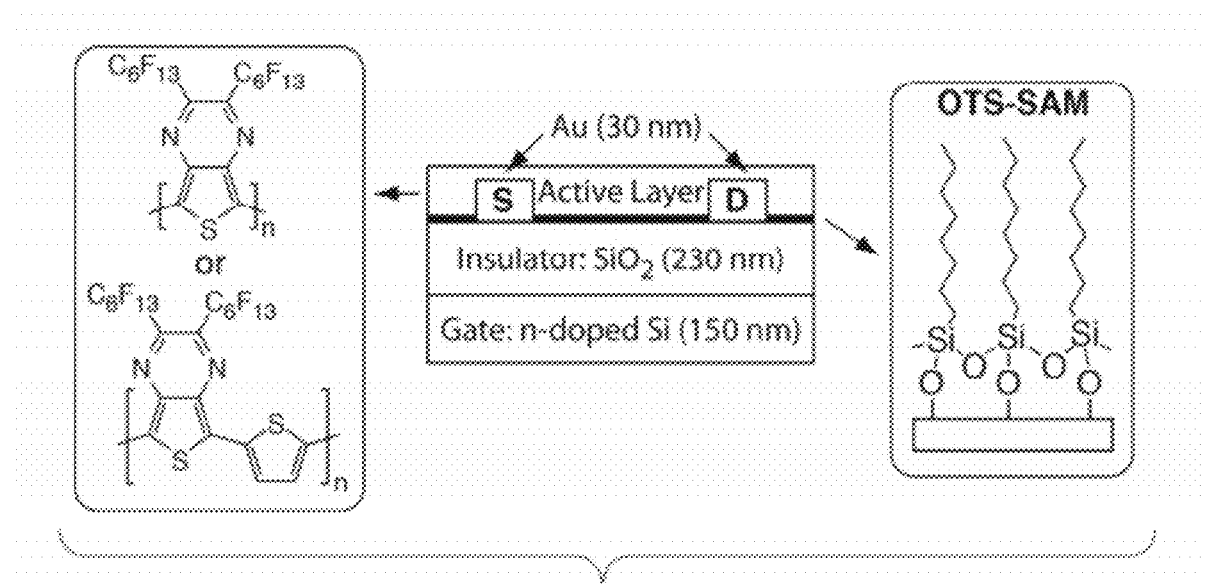
FIG. 30 shows (a) a schematic representation and (b) a photograph of an OFET device containing fluorine-containing polymers described herein.
Figure 30B:
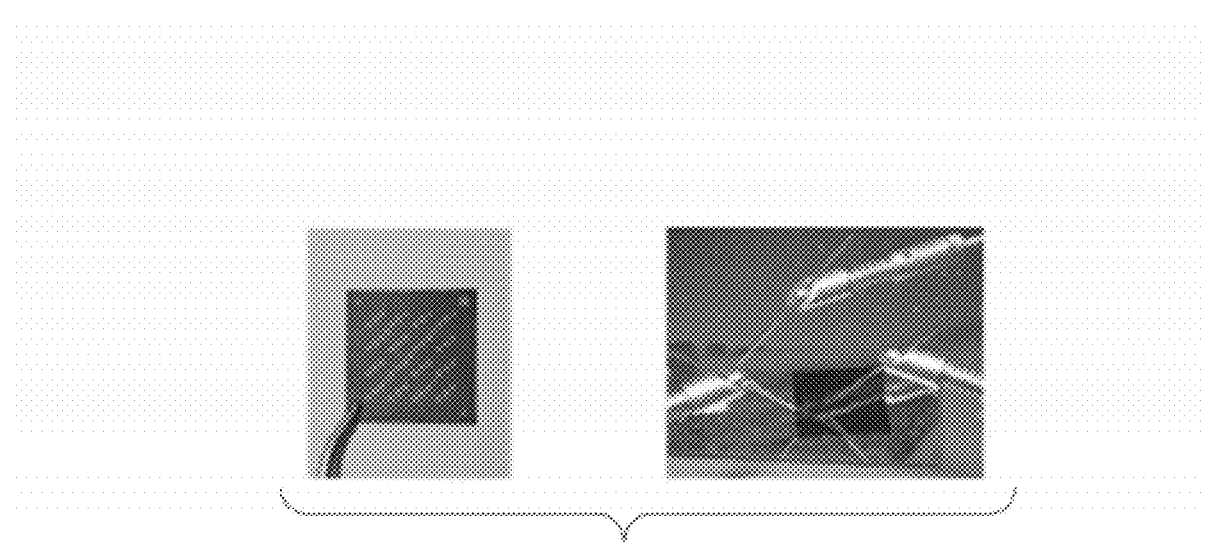

FIG. 30 shows a (a) schematic representation and (b) photographs of an OFET device containing fluorine-containing polymers described herein. The devices were fabricated according the procedure described in Umeda, T. et al., J. Appl. Phys. 2009, 105, 24516. The OFET devices were fabricated as bottom-contact type devices. Highly n-doped silicon substrates were used as common gate electrodes and thermally grown $SiO_2$ was used as the insulator, as illustrated in FIG. 30A. The substrates were sonicated in acetone, isopropyl alcohol, and deionized water in this order for 10 min for each solvent before washed with boiling EtOH vapor. After drying with a nitrogen gun, the substrates were treated with $UV/O_3$ for 15 min. The substrates were immediately transferred into a glove box and immersed into a toluene solution of octyltrichlorosilane (50 mM) for 15 h. The substrates were then removed from the glove box and cleaned by ultrasonication in toluene, then acetone, and then isopropyl alcohol, for 10 min per solvent. After washing with EtOH vapor and drying with a nitrogen gun, the substrates were annealed at 150° C. under an atmosphere of nitrogen gas for 5 min. Hot perfluorodecalin solutions of polymers P4 and P5 (1 mg/0.05 mL) were spin-coated onto the substrates, and the films were annealed at 150° C. for 1.5 h under an atmosphere of nitrogen gas.

Figure 31A:
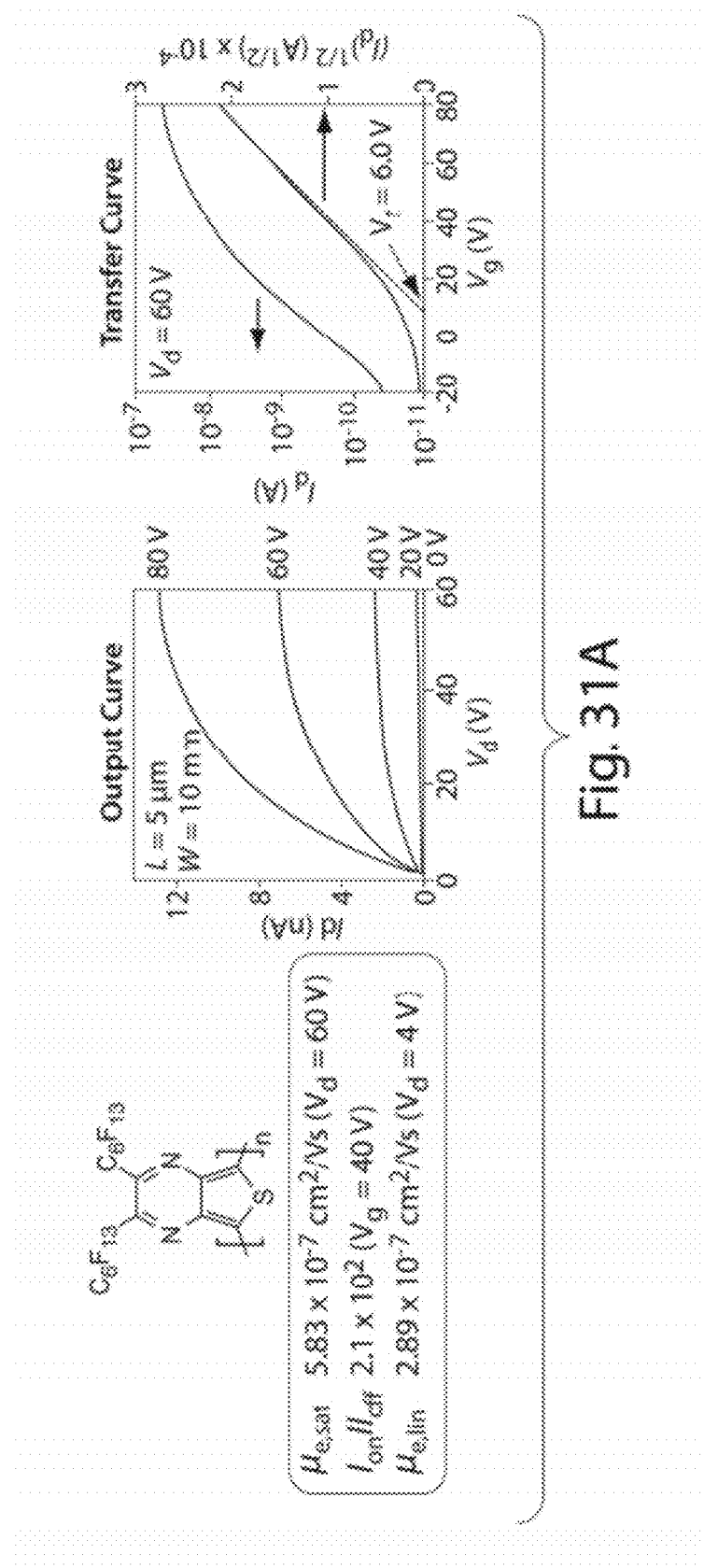
FIG. 31 shows the N-channel OFET properties of devices containing (a) P4 or (b) P5.
Figure 31B:
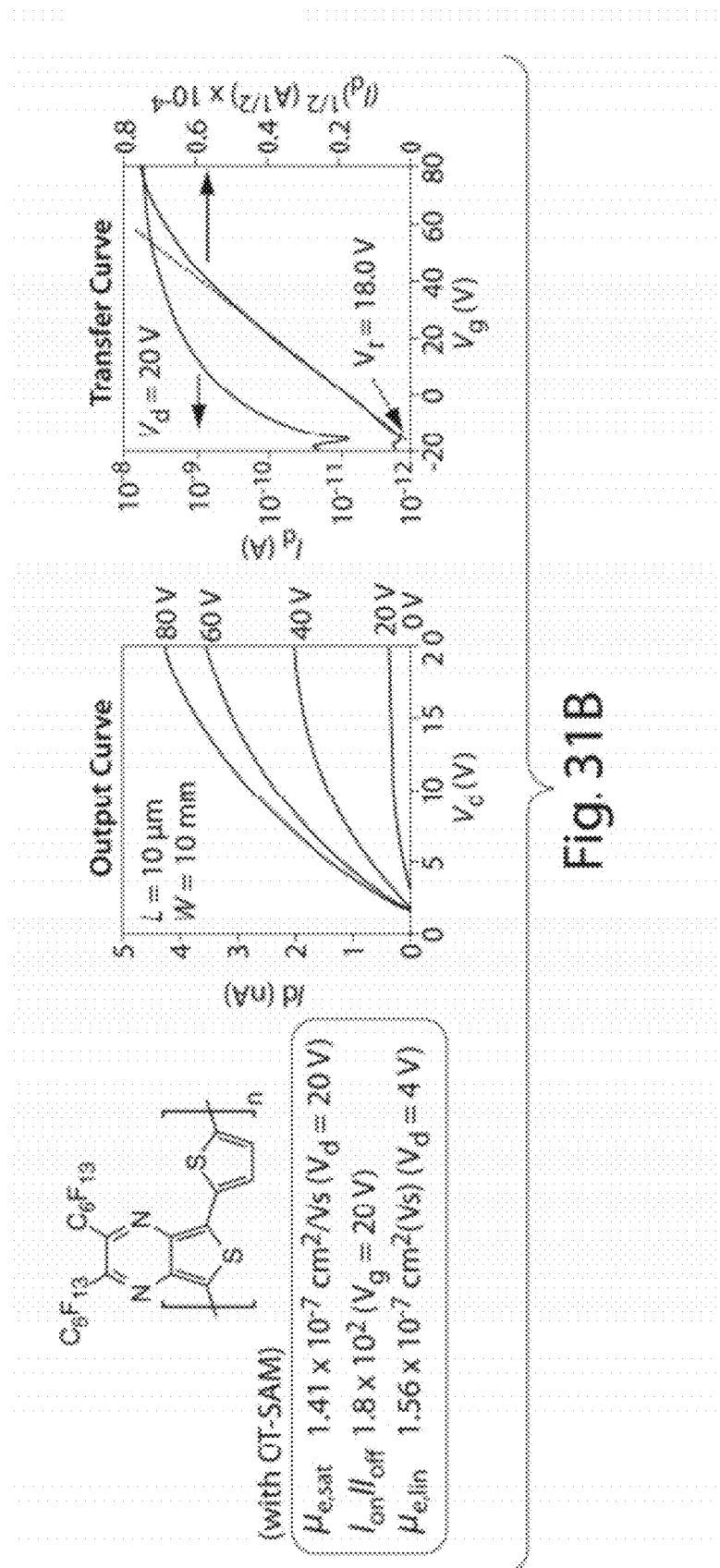

FIG. 31 shows the N-channel OFET properties of devices containing (a) P4 or (b) P5. The mobilities were calculated from the saturation regime and fitted in the regions of largest slope (Horowitz, G. et al. J. Appl. Phys. 2000, 87, 4456).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A polymer, comprising:
   a conjugated pi-backbone, the pi-backbone comprising a plane of atoms; and
   a first group and a second group attached to the pi-backbone, the first group having a first fixed height above the plane and the second group having a second fixed height below the plane wherein the sum of the first and second heights is at least 4.5 Å,
   wherein the polymer has a fluorine content of greater than 60% by mass.

2. The polymer of claim 1, wherein the polymer is a polyarylene ethynylene.

3. The polymer of claim 1, wherein the a sum of the first and second heights is at least 5.0 Å, is at least 5.5 Å, is at least 6.0 Å, or is at least 6.5 Å.

4. The polymer of claim 1, wherein the pi-backbone is essentially free from pi-stacking.

5. The polymer of claim 1, wherein the polymer comprises at least one iptycene repeating unit incorporated into the polymer.

6. The polymer of claim 5, wherein the iptycene repeating unit incorporated into the polymer has the structure:

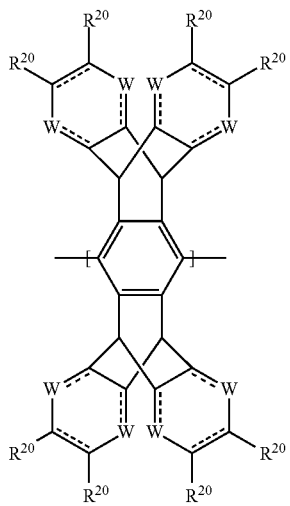

wherein each $R^{20}$ can be the same or different and is hydrogen, alkyl, heteroalkyl, aryl, or heteroaryl, any of which is optionally substituted with one or more fluorine atoms;
each W is CH or $CH_2$; and
each === is a single or double bond.

7. The polymer of claim 5, wherein the iptycene repeating unit incorporated into the polymer has the structure:

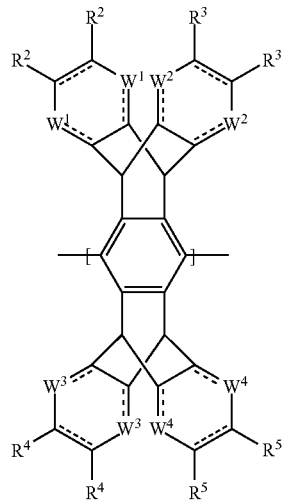

wherein each $R^2$-$R^5$ may be the same or different and is hydrogen, alkyl, heteroalkyl, heteroalkoxy, aryl, or heteroaryl, any of which is optionally substituted with one or more fluorine atoms;
each $W^1$-$W^4$ can be the same or different and is CH or $CH_2$; and
each === is a single or double bond.

8. The polymer of claim 1, wherein the polymer comprises a repeating unit having the structure:

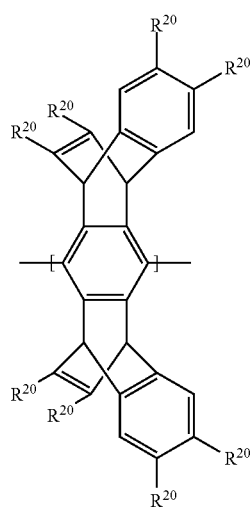

wherein each $R^{20}$ can be the same or different and is hydrogen, alkyl, heteroalkyl, aryl, or heteroaryl, any of which is optionally substituted with one or more fluorine atoms.

9. The polymer of claim 1, wherein the polymer comprises a repeating unit having the structure:

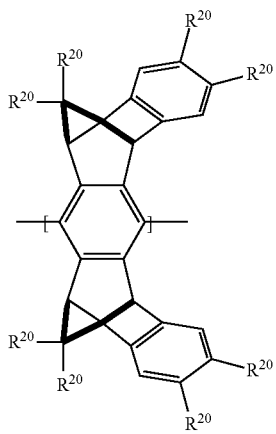

wherein each $R^{20}$ can be the same or different and is hydrogen, alkyl, heteroalkyl, aryl, or heteroaryl, any of which is optionally substituted with one or more fluorine atoms.

10. The polymer of claim 1, wherein the polymer comprises a pi-backbone comprising the structure:

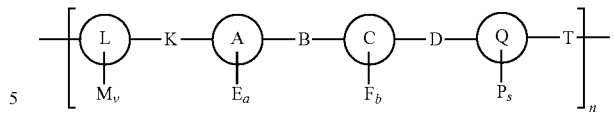

wherein A, C, L, and Q are aromatic groups;

B, D, K, and T are selected from the group consisting of a carbon-carbon double bond and a carbon-carbon triple bond, a, b, s, and v are integers which can be the same or different and are 0-4, provided not all of a, b, s, and v are zero; and n is less than 10,000, wherein at least one of E, F, M, and P comprises the first and second group;

wherein at least one of E, F, M, and P includes a bicyclic ring system having aromatic or non-aromatic groups; and wherein each E, F, M, and P group is or is optionally substituted by one or more $R^{22}$ wherein each $R^{22}$ is selected from the group consisting of hydrogen, alkyl, heteroalkyl, heteroalkoxy, aryl, and heteroaryl, any of which is optionally substituted with one or more fluorine atoms.

11. The polymer of claim 1, wherein the polymer comprises the structure:

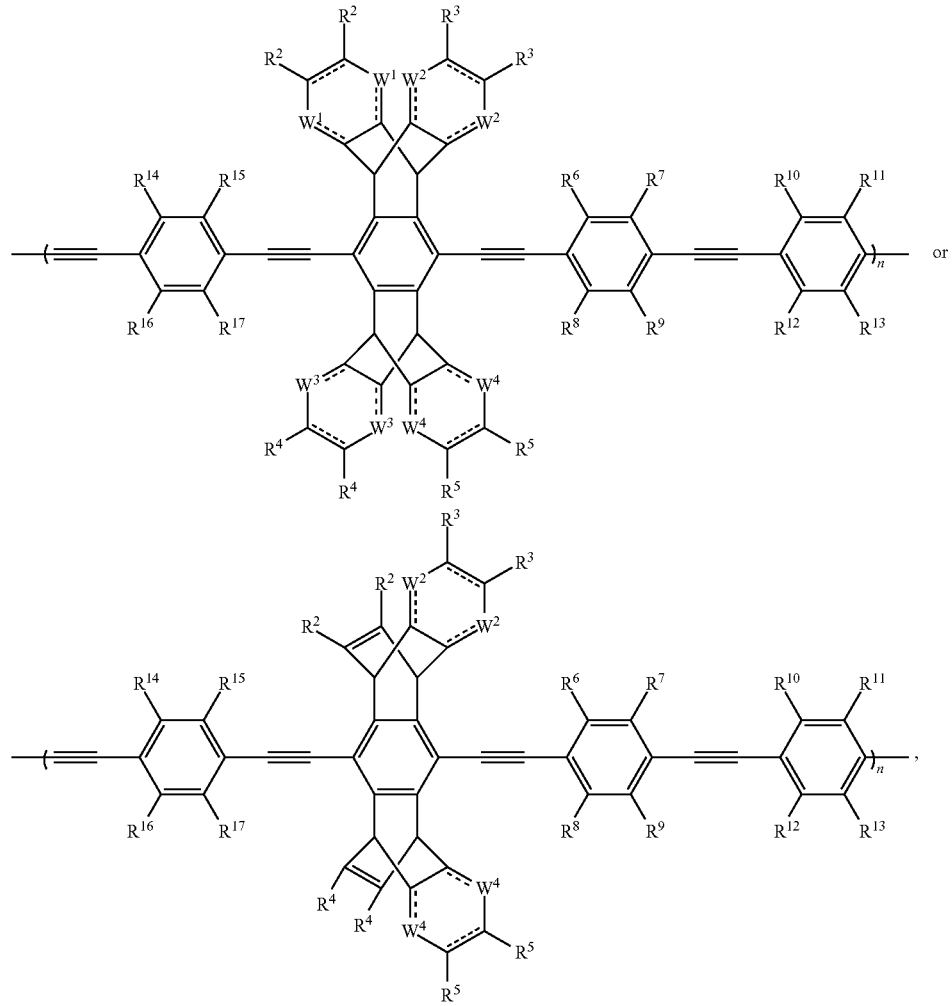

wherein each $R^2$-$R^{17}$ can be the same or different and is hydrogen, alkyl, heteroalkyl, heteroalkoxy, aryl, or heteroaryl, any of which is optionally substituted with one or more fluorine atoms;

each $W^1$-$W^4$ can be the same or different and is CH or $CH_2$; and n is less than 10,000.

12. The polymer of claim 11, wherein each $W^1$ and each $W^3$ is CH; or each $W^2$ and each $W^4$ is CH; or each $W^1$-$W^4$ is CH.

13. The polymer of claim 11, wherein:
each $R^2$ and each $R^4$ is alkyl, heteroalkyl, heteroalkoxy, aryl, or heteroaryl, any of which is optionally substituted with one or more fluorine atoms; and
each $R^3$ and each $R^5$ is hydrogen.

14. The polymer of claim 11, wherein each $R^2$ and each $R^4$ is alkyl, optionally fluorinated.

15. The polymer of claim 11, wherein each of $R^6$-$R^9$ is hydrogen and/or each of $R^{14}$-$R^{17}$ is hydrogen.

16. The polymer of claim 11, wherein:
$R^{10}$ and $R^{13}$ are alkyl, heteroalkyl, heteroalkoxy, aryl, or heteroaryl, any of which is optionally substituted with one or more fluorine atoms; and
$R^{11}$ and $R^{12}$ are hydrogen.

17. The polymer of claim 11, wherein:
$R^{11}$ and $R^{12}$ are alkyl, heteroalkyl, heteroalkoxy, aryl, or heteroaryl, any of which is optionally substituted with one or more fluorine atoms; and
$R^{10}$ and $R^{13}$ are hydrogen.

18. The polymer of claim 1, wherein the polymer has the structure:

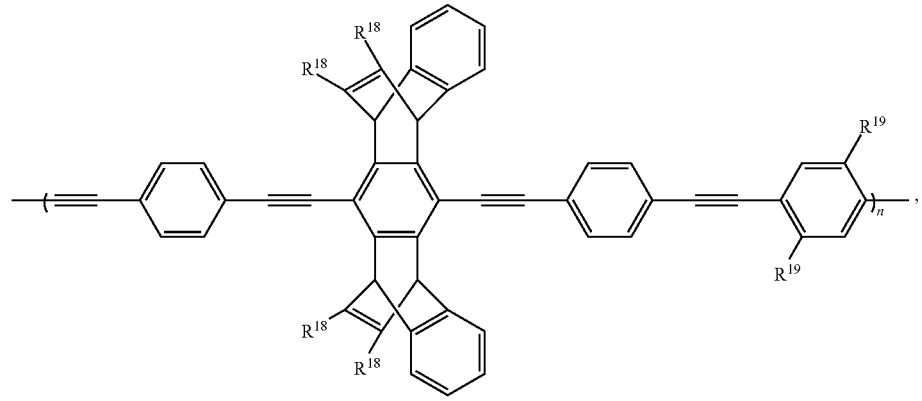

wherein each $R^{18}$ and each $R^{19}$ is alkyl, heteroalkyl, heteroalkoxy, aryl, or heteroaryl, any of which is optionally substituted with one or more fluorine atoms.

19. The polymer of claim 18, wherein the polymer has the structure:

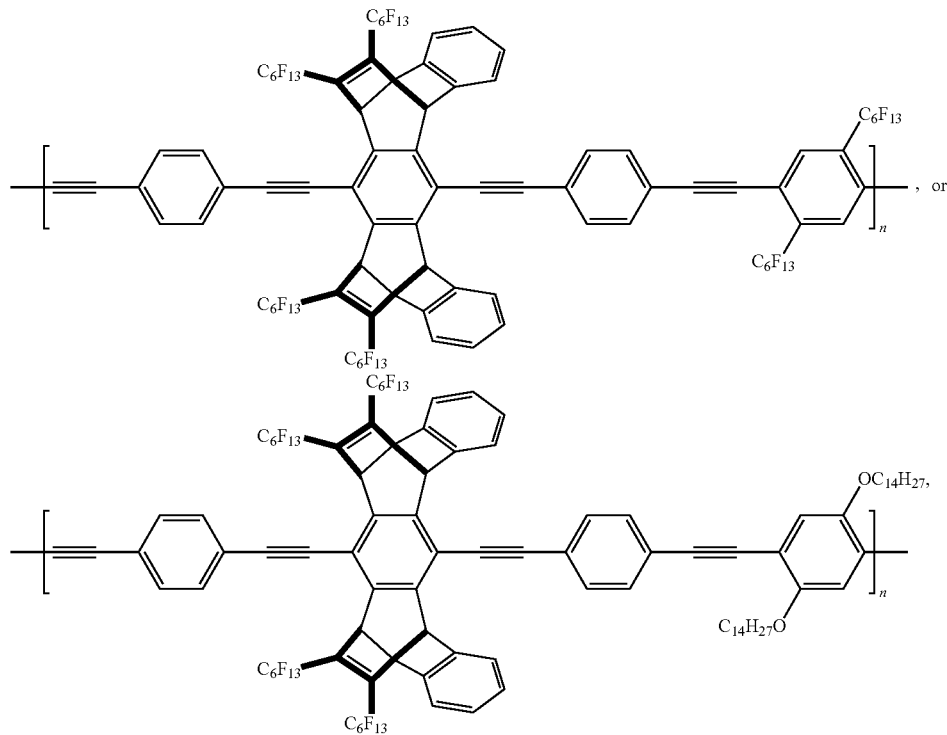

wherein n is less than 10,000.

20. The polymer of claim 18, wherein the polymer has the structure:

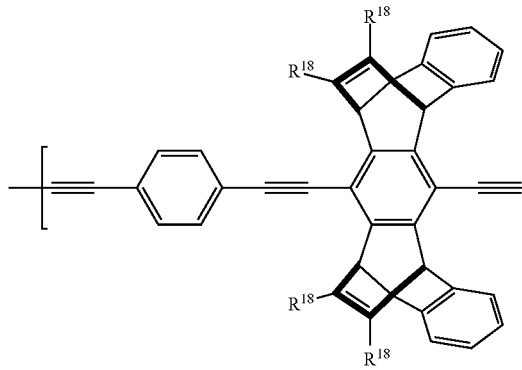

wherein each $R^{18}$ and $R^{23}$ is alkyl, heteroalkyl, heteroalkoxy, aryl, and heteroaryl, any of which is optionally substituted with one or more fluorine atoms;
wherein n is less than 10,000; and
k is an integer between 1-100, or between 1-50, or between 1-20, or between 1-10, or between 1-5.

21. The polymer of claim 1, wherein the polymer comprises at least one monomer having the structure:

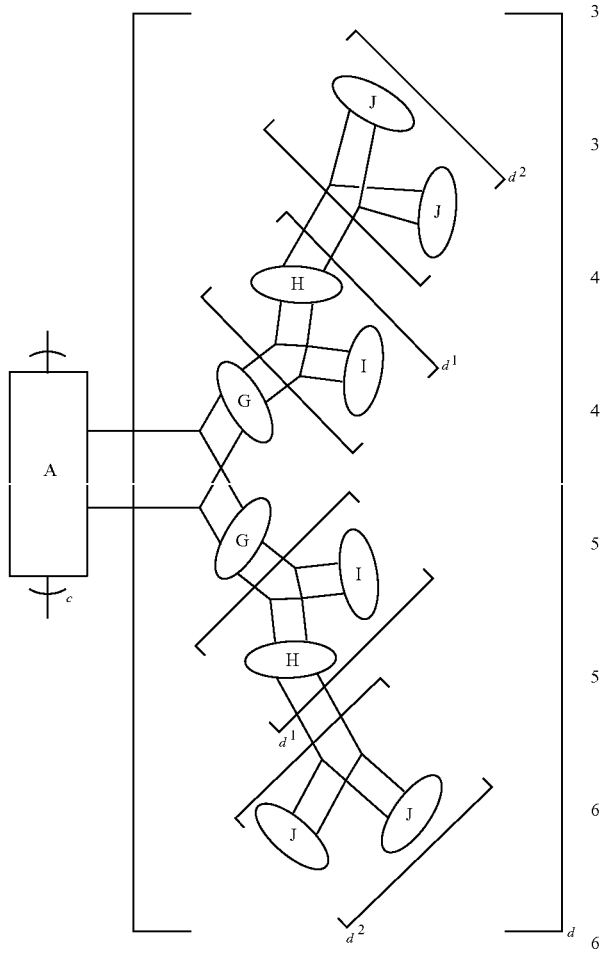

wherein each G, H, I and J are the same or different and are aromatic or cycloalkyl groups, optionally substituted;

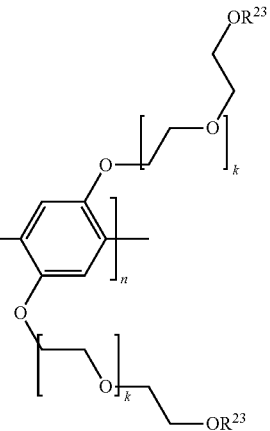

d is 1 or 2;
each $d^1$ is 0 or 1, such that when $d^1=0$, $d^2=0$, and when $d^1=1$, $d^2=0$ or 1;
and c is any number between 1 and 10,000.

22. The polymer of claim 21, wherein G and H are the same or different and are selected from the following aromatic groups:

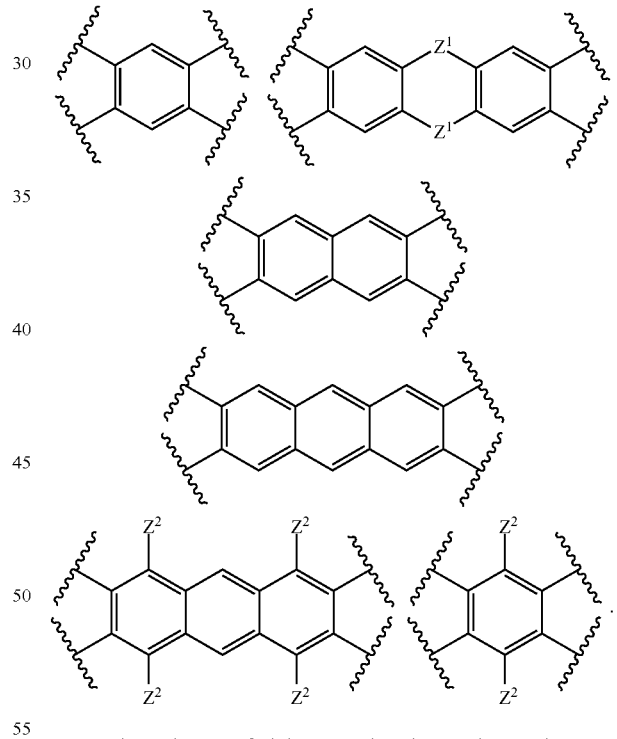

23. The polymer of claim 21, wherein I and J are the same or different and are selected from the following groups:

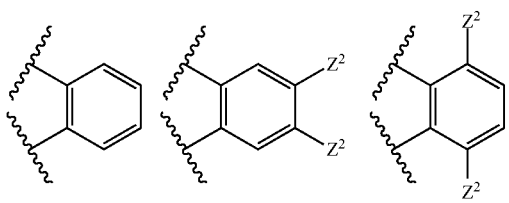

-continued

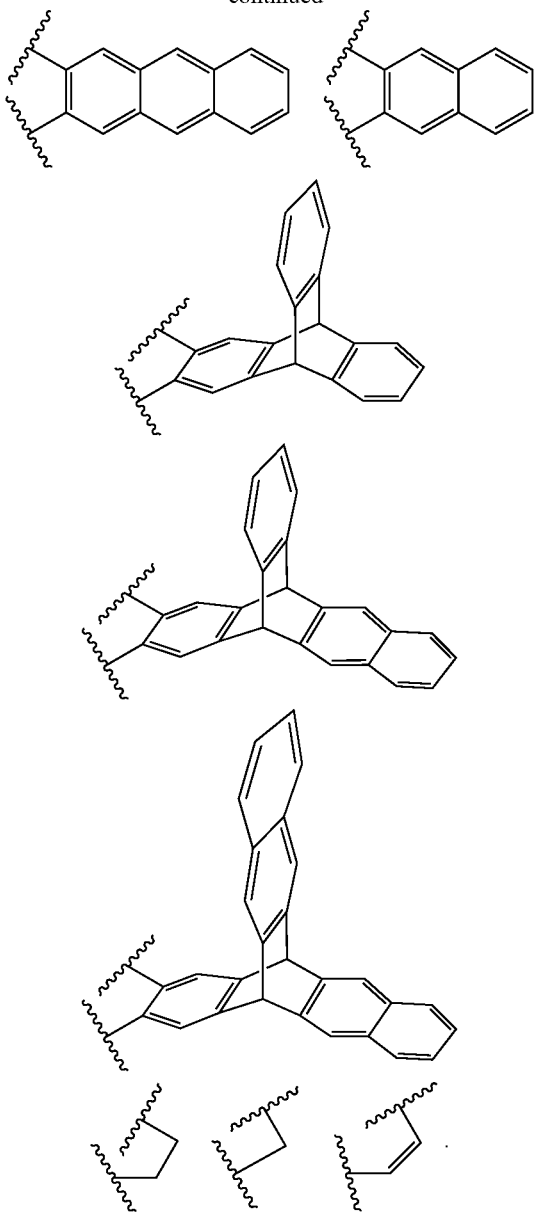

24. The polymer of claim 21, wherein any hydrogen in G, H, I, and J may be optionally substituted by one or more $R^{21}$, wherein each $R^{21}$ can be the same or different and is hydrogen, alkyl, heteroalkyl, aryl, or heteroaryl, any of which is optionally substituted with one or more fluorine atoms.

25. The polymer of claim 1, wherein the polymer comprises at least one fluoroalkyl group selected from the group consisting of —$C_2F_5$, —$CH_2CF_3$, —$C_3F_7$, —$(CH_2)_2CF_3$, —$C_4F_9$, —$(CH_2)_2(CF_2)CF_3$, —$(CH_2)_3CF_3$, —$(CH_2)_2(CHF)CF_3$, —$C_5F_{11}$, —$(CH_2)_2(CF_2)_2CF_3$, —$C_6F_{13}$, —$(CH_2)_2(CF_2)_3CF_3$, —$(CH_2)_2(CF_2)_4CF_3$, —$C_7F_{15}$, —$(CH_2)_2(CF_2)_5CF_3$, —$(CH_2)_2(CF_2)_9CF_3$, —$(CH_2)_3(CF_2)_4CF_3$, —$(CH_2)_2(CF_2)_2(CF_3CF_2CF_2)CF(CF_2)_2CF_3$, —$C_8F_{17}$, —$C_9F_{19}$, —$C_{10}F_{21}$, —$C_{11}F_{23}$, and —$C_{12}F_{25}$.

26. The polymer of claim 1, wherein the polymer comprises the group $(CH_2CH_2O)_kR^{23}$, wherein k is an integer between 1-100, or between 1-50, or between 1-20, or between 1-10, or between 1-5, and $R^{23}$ is hydrogen, alkyl, heteroalkyl, aryl, or heteroaryl, each optionally substituted.

27. An emulsion, comprising:
a non-fluorous continuous phase;
a fluorous non-continuous phase; and
a polymer of claim 1 substantially contained within the fluorous non-continuous phase.

28. An emulsion, comprising:
a non-fluorous continuous phase and a fluorous non-continuous phase, wherein a fluorous/non-fluorous interface is present between the fluorous and the non-fluorous phase; and
a polymer of claim 1 arranged at the interface.

29. A method of determining, treating, or imaging a condition and/or disease in a subject, comprising:
providing an emulsion, comprising:
a fluorous non-continuous phase;
a non-fluorous continuous phase;
at least one surfactant;
at least one surface-altering moiety; and
a polymer of claim 1, wherein the polymer and the at least one surfactant is contained with the fluorous phase;
administering the emulsion to the subject; and
imaging at least a portion of the subject.

* * * * *